(12) United States Patent
Reed et al.

(10) Patent No.: US 6,696,558 B2
(45) Date of Patent: Feb. 24, 2004

(54) BAG PROTEINS AND NUCLEIC ACID MOLECULES ENCODING THEM

(75) Inventors: John C. Reed, Rancho Santa Fe, CA (US); Shinichi Takayama, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/394,142

(22) Filed: Sep. 9, 1999

(65) Prior Publication Data

US 2003/0191054 A1 Oct. 9, 2003

Related U.S. Application Data

(60) Provisional application No. 60/155,212, filed on Sep. 9, 1998.

(51) Int. Cl.$^7$ .............................................. C07H 21/04

(52) U.S. Cl. ..................................................... 536/23.5

(58) Field of Search ........................ 536/23.5; 530/350

(56) References Cited

U.S. PATENT DOCUMENTS

| | | | |
|---|---|---|---|
| 5,539,094 A | | 7/1996 | Reed et al. ................. 536/23.5 |
| 5,650,491 A | * | 7/1997 | Reed et al. .................. 530/350 |
| 5,652,223 A | | 7/1997 | Kohn et al. .................... 514/44 |

FOREIGN PATENT DOCUMENTS

| | | | |
|---|---|---|---|
| WO | WO 95/13292 | 5/1995 | |
| WO | WO-95/13292 A1 | * 5/1995 | ........... C07K/14/47 |

OTHER PUBLICATIONS

Kozak M. EMBO J. May 1, 1997;16(9):2482–92.*
Grunert et al. EMBO J. Aug. 1, 1994;13(15):3618–30.*
Zeiner et al. Proc Natl Acad Sci USA. Dec. 5, 1995; 92 (25):11465–9.*
Search Report us—09–394–142b–2.rge, pp. 3 and 4; see result 3.*
Takayama, S, Direct Submission, Sep. 03, 1997, Database GenBank Accession No. AF022224, *Homo sapiens* Bcl–2–binding protein (BAG–1) mRNA, complete cds; see USPTO Search Report Results of US–09–394–142b–2_copy_1_85.rge (result 2).*
Takayama, S, Direct Submission, Sep. 03, 1997, Database GenBank Accession No. AF022224, *Homo sapiens* Bcl–2–binding protein (BAG–1) mRNA, complete cds; see USPTO Search Report Results of US–09–394–142b–2_copy_57_89.rge (result 2).*
Takayama, S, Direct Submission, Sep. 03, 1997, Database GenBank Accession No. AF022224, *Homo sapiens* Bcl–2–binding protein (BAG–1) mRNA, complete cds; see USPTO Search Report Results of US–09–394–142b–1_copy_272_319.rge (result 2).*
Takayama, S, Direct Submission, Sep. 03, 1997, Database GenBank Accession No. AF022224, *Homo sapiens* Bcl–2–binding protein (BAG–1) mRNA, complete cds; see USPTO Search Report Results of US–09–394–142b–1_copy_46_1291.rge (result 1).*
Zeiner, M, Direct Submission, Jul. 28, 1994, Database GenBank Accession No. Z35491, *H. sapiens* mRNA for novel glucocorticoid receptor–associated protein; see USPTO Search Report US–09–394–142b–2_copy_1_85.rge, result 4.*
Hillier, L, et al, Unpublished, 1997, Database GenBank EST Accession No. AI815738, au43g01.y1 Schneider fetal brain 00004 *Homo sapiens* cDNA clone IMAGE:2517552, 5'similar to TR:075315; see USPTO Search Report US–09–394–142b–2_copy_1_85, result 1.*
Zeiner, M, Direct Submission, Jul. 28, 1994, Database GenBank Accession No. Z35491, *H. sapiens* mRNA for novel glucocorticoid receptor–associated protein; see USPTO Search Report US–09–394–142b–2_copy_57_89.rge, result 4.*
Hillier, L, et al, Unpublished, 1997, Database GenBank EST Accession No. AI815738, au43g01.y1 Schneider fetal brain 00004 *Homo sapiens* cDNA clone IMAGE:2517552, 5' similar to TR:075315; see USPTO Search Report US–09–394–142b–2_copy_57_89, result 2.*
Zeiner, M, Direct Submission, Jul. 28, 1994, Database GenBank Accession No. Z35491, *H. sapiens* mRNA for novel glucocorticoid receptor–associated protein; see USPTO Search Report US–09–394–142b–1_copy_272_8319.rge, result 4.*
Hillier, L, et al, Unpublished, 1997, Database GenBank EST Accession No. AI815738, au43g01.y1 Schneider fetal brain 00004 *Homo sapiens* cDNA clone IMAGE:2517552, 5' similar to TR:075315; see USPTO Search Report US–09–394–142b–1_copy_272_319, result 3.*
Takayama, S, Direct Submission, Sep. 03, 1997, Database GenBank Accession No. AF022224, *Homo sapiens* Bcl–2–binding protein (BAG–1) mRNA, complete cds; see USPTO Search Report Results of US–09–394–142b–1.rge (result 1).*
Takayama, S, et al, 1996, Cloning of cDNAs encoding the human BAG1 protein and localization of the human BAG1 gene to chromosome 9p12, Genomics, vol. 35, No. 3, pp. 494–498.*
Takayama et al., "An Evolutionarily Conserved Family of Hsp70/Hsc70 Molecular Chaperone Regulators," *J. Biol. Chem.*, 274(2):781–786 (1999).

(List continued on next page.)

Primary Examiner—Anthony C. Caputa
Assistant Examiner—Stephen L. Rawlings
(74) Attorney, Agent, or Firm—McDermott, Will & Emery

(57) ABSTRACT

The present invention provides a family of BAG–1 related proteins from humans (BAG–1L, BAG–1, BAG–2, BAG–3, BAG–4 and BAG–5), the invertebrate *C. elegans* (BAG–1, BAG–2) and the fission yeast *S. pombe* (BAG–1A, BAG–1B) and the nucleic acid molecules that encode them.

2 Claims, 35 Drawing Sheets

OTHER PUBLICATIONS

Takayama et al., "Cloning of cDNAs Encoding the Human BAG1 Protein and Localization of the Human BAG1 Gene to Chromosome 9p12," *Genomics*, 35:494–498 (1996).

Takayama et al., "Expression and Location of Hsp70/Hsc–Binding Anti–Apoptotic Protein BAG–1 and Its Variants in Normal Tissues and Tumor Cell Lines," *Canc. Res.*, 58:3116–3131 (1998).

Zeiner and Gehring, "A Protein that Interacts with Members of the Nuclear Hormone Receptor Family: Identification and cDNA Cloning," *Proc. Natl. Acad. Sci.*, 92:11465–11469 (1995).

Ausubel et al., Current Protocols in Molecular Biology, John Wiley and Sons, New York, (1994).

Database, Genbank–EST, National Center for Biotech. Info., Accession No. AA363697, Hillier et al., "WashU–NCI human EST project," Dec. 16, 1997.

Database, Genbank–EST, National Center for Biotech. Info., Accession No. AA456862, NCI_CGAP, "National Cancer Institute, Cancer Genome Anatomy Project (CGAP), Tumor Gene Index," Aug. 15, 1997.

Database, Genbank–EST, National Center for Biotech. Info., Accession No. G29287, Myers, Oct. 4, 1996.

Database, Genbank–EST, National Center for Biotech. Info., Accession No. G06974, Hudson, "Whitehead Institute.MIT Center for Genome Research," Oct. 19, 1995.

Database, Genbank–EST, National Center for Biotech. Info., Accession No. V81267, Otsuka Pharm Co. Ltd., "New Bcl–2 interaction protein gene (Bis)–useful for elucidation of the molecular mechanism of apoptosis, and in diagnosis, prevention and treatment of diseases," Dec. 15, 1998.

Database, Genbank–EST, National Center for Biotech. Info., Accession No. T19051, Matsubara et al., "Identifying gene signatures in 3'–directed human cDNA library," Jun. 01, 1995.

Database, Genbank–EST, National Center for Biotech. Info., Accession No. Q90296, La Jolla Cancer Research Foundation, "Human Bcl–2 associated protein BAG–1 cDNA," May 18, 1995.

Ellis, "Molecular chaperones: Avoiding the crowd," *Curr. Biol.* 7:R531–R533 (1997).

Höfeld et al., "Hip, a novel cochaperone involved in the eukaryotic Hsc70/Hsp40 reaction cycle," *Cell* 83:589–598 (1995).

Höfeld et al., "GrpE–like regulation of the Hsc70 chaperone by the anti–apoptotic protein BAG–1," *EMBO J.* 16:6209–6216 (1997).

Huse et al., "Generation of a large combinatorial library of the immunoglobulin repertoire in phage lambda," *Science* 246:1275–1281 (1989).

Innis et al., PCR Protocols—A guide to methods and applications, Academic Press, Inc., pp. 40–41 (1990).

Matsuzawa et al., "p53–inducible human homologue of Drosophila seven in absentia (Siah) inhibits cell growth: suppression by BAG–1," *EMBO J.* 17:2736–2747 (1998).

Minami et al., "Regulation of the heat–shock protein 79 reaction cycle by the mammalian DnaJ homolog, Hsp40," *J. Biol. Chem.* 271:19617–19624 (1996).

Nielsen, P.E. et al., "Peptide nucleic acids (PNAs): Potential anti–sense and anti–gene agents," *Anticancer Drug Des.* 8:53–63 (1993).

Prapapanich et al., "Mutation of Hip's carboxy–terminal region inhibits a transitional stage of progesterone receptor assembly," *Mol. & Cell Biol.* 18:944–952 (1998).

Sambrook et al., Molecular cloning: A laboratory manual, $2^{nd}$ Edition, Cold Spring Harbor Labortory Press, (1989).

Sudol, "The WW module competes with the SH3 domain?," *TIBS* 21:161–163 (1996).

Takayama et al., "BAG–1 modulates the chaperone activity of Hsp70/Hsc70," *EMBO J.* 16:4887–4896 (1997).

Terada et al., "The human DnaJ homologue dj2 facilitates mitochondrial protein import and luciferase refolding," *J. Cell Biol.* 139:1089–1095 (1997).

Xie et al., "Acidic pH promotes dimerization of Bcl–2 family proteins," *Biochem.* 37:6410–6418 (1998).

Zeiner et al., "Mammalian protein RAP46: an interaction partner and modulator of 70 kDa heat shock proteins," *EMBO J.* 16:5483–5490 (1997).

Zeiner and Gehring, "A protein that interacts with members of the nuclear hormone receptor family: Identification and cDNA cloning," *Proc. Natl. Acad. Sci. USA* 92:11465–11469 (1995).

* cited by examiner

FIGURE 1

[Figure showing a nucleotide sequence with corresponding amino acid translation, with position numbers 90, 180, 270, 360, 450, 540, 630, 720, 810, 900, 990, 1080, 1170, 1260, 1291 marked on the right. The sequence includes annotations for BAG-1L, BAG-1, and BAG-1M start sites.]

FIGURE 2A

```
GCAGCCGCGG TGTCCGAAG TCCTCCCGGG TTGCCCCGGC GGGGTCAGAG CGGGGGCGGG GGAGGGCGGG CGCGGCGTTG GTGACGGCCA CCCTGCAGCC
CAGGGAGCGC TCCACTCGCT GCCGCCGGAG GGCCGGTGAC CTCTTGGCTA GCCCGCGTCG GAGGCTTAGA TGGCTCAGGC GAAGATCAAC      90
                                                                                   . M  A  Q  A  K  I  N             180

GCTAAAGCCA ACAGAGGGCG CTCTGCCGC  TCCTCCTCCA  TGGCTGACCG  CTCCAGCCGC  CTCCAGCCGC  CTCCTGGACC  GCCTGGAGCTC  GCTGGAGCTC    270
 A  K  A  N  R  E  G  R  F  C  R  S  S  M  A  D  R  S  S  R  L  L  E  S  L  D  Q  L  E  L                           360

AGGTTGAAG  CTTTGAAGA  AGCAGCAACT  GCTGTTGAGC  AAGAGAAAGA  AATCCTTCTG  GAATGATCC  ACAGTATCCA  AATAGCCAG                450
 R  V  E  A  L  R  E  A  A  T  A  V  E  Q  E  K  E  I  L  L  E  M  I  H  S  I  Q  N  S  Q                           540

GACATAGCGG AGATGCGTCA CGAGAAAGA  GAAGAATTAA  ATCTGACTGC  AAACCGTTTG  ATGGAAGAA  CTCTCACCGT  TGAAGTGTCA               540
 D  M  R  Q  I  S  D  G  E  R  E  E  L  N  L  T  A  N  R  L  M  Q  R  T  L  T  V  E  V  S

GTAGAAACAA TTAGAAACCC CCAGCAGCAA  GAATCCCTAA  AGCATGCCAC  AAGGATTATT  GATGAGGTGG  TCAATAAGTT  TCTGGATGAT              630
 V  E  T  I  R  N  P  Q  Q  Q  E  S  L  K  H  A  T  R  I  I  D  E  V  V  N  K  F  L  D  D

TTGGAAATG CCAAGAGTCA TTTAATGTCA  CTCTACAGTG  CATGTTCATC  AGAGACTCTG  TGAGGTGCCA  CATGGCCAG  TTGATCAGAA  GTTCAATCC    720
 L  G  N  A  K  S  H  L  M  S  L  Y  S  A  C  S  S  E  V  P  H  Q  P  V  D  Q  K  F  Q  S

ATAGTAATTC GCTGTGCTCT TGAAGACTAG  AAGAAATTAG  AGAGAGATT  AGAGAGATT  CTTAGAAATA  TTGAAACTC  TGACAGGCC                 810
 I  V  I  G  C  A  L  E  D  Q  K  K  I  K  R  R  L  E  T  L  L  R  N  I  E  N  S  D  K  A

ATCAGATTAT TAGAGCATTC TAAAGGGGCT GGTTCCAAAA  AATCTGCACA  CTCTGCACA  AATTGCTGAA  ACAGATTCA  ATTAGTCTTC  AAACCTAAGA
 I  K  L  L  E  H  S  K  G  A  G  S  K  T  L  Q  Q  N  A  E  S  R  F  N
```

FIGURE 2B

```
GCATTTACAC AATACACAAG GTGTAAAAAT GATAAAATAC TATTTTAATT GATAACTAGT TCTTTGTTAG GTATAACCAC TTAGTTGACA       900
CTGATAGTTG TTTCAGATGA GGAAATATT CCATCAAGTA TCTTCAGTTT TGTGAATAAC AAACTAGCA ATATTTAAT TATCTATCTA         990
GAGATTTTTT AGATTGAATT CTTGTCTTGT ACTAGATCT AGCATATTTC ACTATTCTGT GGATGAATAC ATAGTTTGTG GGGAAAACAA     1080
ACGTTCAGCT AGGGGCAAAA AGCATGACTG CTTTTTCCTG TCTGGCATGG AATCACGCAG TCACCTTGGG CATTTAGTTT ACTAGAAATT     1170
CTTTACTGG                                                                                            1179
```

FIGURE 3

```
GCGGAGCTCC GCATCCAACC CCGGGCCGCG GCCAACTTCT CTGGACTGGA CCAGAAGTTT CTAGCCGGCC AGTTGCTACC TCCCTTTATC     90
 A  E  L  R   I  Q  P   A  A  A   A  N  F  S   G  L  D   Q  K  F   L  A  G  Q   L  L  P   P  F  I

TCCTCCTTCC CCTCTGGCAG CAGGGAGGCT ATTTCCAGAC ACTTCCACCC CTCTCTGGCC ACGTCACCCC CGCCTTTAAT TCATAAAGGT    180
 S  S  F  P   S  G  S   E  E  R   I  S  R  H   F  H  P   S  L  A   T  S  P  P   P  L  I   H  K  G

GCCCGGCGCC GGCTTCCGGG ACACGTCGGC GGCGGAGAGG GGGCCACGGC GGCGGCCCGG CCAGAGACTC GGCGCCGGGA GCCAGCGCCC    270
 A  R  R  R   L  P  G   H  V  G   G  G  E  G   P  T  A   A  A  R   P  E  T  R   R  P  E   P  A  P

CGCACCCGCG CCCCAGCGGG CAGACCCCAA CCCAGCAGTGA GCGCCGCCAC CCACTCGCCC ATGATGCAGG TGGCGTCCGG CAACGGTGAC    360
 R  T  R  A   P  A  G   R  P  Q   P  S  H  S   A  A  T   H  S  P   H  H  Q  V   A  S  G   N  G  D

CGGGACCCTT TGCCCCCCGG ATGGGAGATC AAGATCGACC CGCAGACCGG CTGGCCCTTC TTCGTGGACC ACAACAGCCG CACCACTACG    450
 R  D  P  L   P  P  G   H  E  I   K  I  D  P   Q  T  G   W  P  F   F  V  D  H   N  S  R   T  T  T

TGGAACGACC CGCGCGTGCC CTCTGAGGGC CCCAAGGAGA CTCCATCCTC TGCCAATGGC CCTTCCGGG AGGGCTCTAG GCTGCCGCCT    540
 W  N  D  P   R  V  P   S  E  G   P  K  E  T   P  S  S   A  N  G   P  S  R  E   G  S  R   L  P  P

GCTAGGGAAG GCCACCCTGT GTACCCCCAG CTCCGACCAG GCTACATTCC CATTCCTGTG CTCCATGAAG GCGCTGAAGA CCGGCAGGTG    630
 A  R  E  G   H  P  V   Y  P  Q   L  R  P  G   Y  I  P   I  P  V   L  H  E  G   A  E  D   R  Q  V

CACCCTTTCC ATGTCTATCC CCAGCCTGGG ATGCAGCGAT TCCGAACTGA GGCGGCAGCA GCGGCTCCTC AGAGGTCCCA GTCACCTCTG    720
 H  P  F  H   V  Y  P   Q  P  G   M  Q  R  F   R  T  E   A  A  A   A  P  Q  R   S  Q  S   P  L

CGGGGCATGC CAGAAACCAC TCAGCCAGAT AAACAGTGTG GACAGGTGGC AGCGGGGGCG GCAGCCCAGC CCCAGCCTC CCACGGACCT    810
 R  G  M  P   E  T  T   Q  P  D   K  Q  C  G   Q  V  A   A  A  A   A  Q  P  R   S  Q  P   H  G  P

GAGCGGTCCC AGTCTCCAGC TGCCTCTGAC TGCTCATCCT CATCCTCCTC GGCCAGCCTG CCTTCCTCCG GCAGGAGCAG CCTGGGCAGT    900
 E  R  S  Q   S  P  A   A  S  D   C  S  S  S   S  S  S   A  S  L   P  S  S  G   R  S  S   L  G  S

CACCAGCTCC CGCGGGGGTA CATCTCCATT CCGGTGATAC ACGAGCAGAA CGTTACCCGG CCAGCAGCCC AGCCCTCCTT CCACAAAGCC    990
 H  Q  L  P   R  G  Y   I  S  I   P  V  I  H   E  Q  N   V  T  R   P  A  A  Q   P  S  F   H  K  A

CAGAAGACGC ACTACCCAGC GCAGAGGGGT GAGTACCAGA CCCACCAGCC TGTGTACCAC AAGATCCAGG GGGATGACTG GGAGCCCCGG   1080
 Q  K  T  H   Y  P  A   Q  R  G   E  Y  Q  T   H  Q  P   V  Y  H   K  I  Q  G   D  D  W   E  P  R

CCCCTGCGGG CGGCATCCCC GTTCAGGTCA TCTGTCCAGG GTGCATCGAG CCGGGAGGGC TCACCAGCCA GGAGCAGCAC GCCACTCCAC   1170
 P  L  R  A   A  S  P   F  R  S   S  V  Q  G   A  S  S   R  E  G   S  P  A  R   R  S  S   T  P  L  H

TCCCCCTGCG CCATCCGTGT GCACACCGTG GTCGACAGGC CTCAGCAGCC CATGACCCAT CGAGAAACTG CACCTGTTTC CCAGCCTGAA   1260
 S  P  S  P   I  R  V   H  T  V   V  D  R  P   Q  Q  P   H  T  H   R  E  T  A   P  V  S   Q  P  E

AACAAACCAG AAAGTAAGCC AGGCCCAGTT GGACCAGAAC TCCCTCCTGG ACACATCCCA ATTCAAGTGA TCCGCAAAGA GGTGGATTCT   1350
 N  K  P  E   S  K  P   G  P  V   G  P  E  L   P  P  G   H  I  P   I  Q  V  I   R  K  E   V  D  S

AAACCTGTTT CCCAGAAGCC CCCACCTCCC TCTGAGAAGG TAGAGGTGAA AGTTCCCCCT GCTCCAGTTC CTTGTCCTCC TCCCAGCCCT   1440
 K  P  V  S   Q  K  P   P  P  P   S  E  K  V   E  V  K   V  P  P   A  P  V  P   C  P  P   P  S  P
```

```
GGCCCTTCTG CTGTCCCCTC TTCCCCCAAG AGTGTGGCTA CAGAAGAGAG GGCAGCCCCC AGCACTGCCC CTGCAGAAGC TACACCTCCA   1530
 G  P  S  A   V  P  S   S  P  K   S  V  A  T   E  E  R   A  A  P   S  T  A  P   A  E  A   T  P  P

AAACCAGGAG AAGCCGAGGC TCCCCCAAAA CATCCAGGAG TGCTGAAAGT GGAAGCCATC CTGGAGAAGG TGCAGGGCT GGAGCAGGCT   1620
 K  P  G  E   A  E  A   P  P  K   H  P  G  V   L  K  V   E  A  I   L  E  K  V   Q  G  L   E  Q  A

GTAGACAACT TTGAAGGCAA GAAGACTGAC AAAAAGTACC TGATGATCGA AGAGTATTTG ACCAAAGAGC TGCTGGCCCT GGATTCAGTG   1710
 V  D  N  F   E  G  K   K  T  D   K  K  Y  L   M  I  E   E  Y  L   T  K  E  L   L  A  L   D  S  V

GACCCCGAGG GACGAGCCGA TGTGCGTCAG GCCAGGAGAG ACGGTGTCAG GAAGGTTCAG ACCATCTTGG AAAAACTTGA ACAGAAAGCC   1800
 D  P  E  G   R  A  D   V  R  Q   A  R  R  D   G  V  R   K  V  Q   T  I  L  E   K  L  E   Q  K  A

ATTGATGTCC CAGGTCAAGT CCAGGTCTAT GAACTCCAGC CCAGCAACCT TGAAGCAGAT CAGCCACTGC AGGCAATCAT GGAGATGGGT   1890
 I  D  V  P   G  Q  V   Q  V  Y   E  L  Q  P   S  H  L   E  A  D   Q  P  L  Q   A  I  H   E  H  G

GCCGTGGCAG CAGACAGGG CAAGAAAAAT GCTGGAAATG CAGAAGATCC CCACACAGAA ACCAGCAGC CAGAAGCCAC AGCAGCAGCG   1980
 A  V  A  A   D  K  G   K  K  N   A  G  N  A   E  D  P   H  T  E   T  Q  Q  P   E  A  T   A  A  A

ACTTCAAACC CCAGCAGCAT GACAGACACC CCTGGTAACC CAGCAGCCAC GTAGCCTCTG CCCTGTAAAA GTCAGACTCG GAACCGATGT   2070
 T  S  H  P   S  S  H   T  D  T   P  G  N  P   A  A  P

GTGCTTTAGG GATTTTAGTT GCATGCATTT CAGAGACTTT AGGTCAGTTG GTTTTGATTA GCTGCTTGGT ATGCAGTACT TGGGTGAGGC   2160
AAACACTATA AAGGCTAAA AGGGAAAATG ATGCTTTTCT TCAATATTCT TACTCTTGTA CAATTAAAGA AGTTGCTTGT TGTTTGAGAA   2250
GTTTAACCCC GTTGCTTGTT CTGCAGCCCT GTCAACTTGG GCACCCCCAC CACCTGTTAG CTGTGGTTGT GCACTGTCTT TTGTAGCTCT   2340
GGACTGGAAG GGTAAGATGG GAGTCAATTA CCAATGACAT AAAATGAAA CATTTATCAG AAATATTGCC ATTTTAATGA GATGATTTTC   2430
TTCATCTCAT AATTAAAATA CCTGACTTTA GAGAGAGTAA AATGTGCCAG GAGCCATAGG AATATCTGTA TGTTGGATGA CTTTAATGCT   2520
ACATTTTH                                                                                           2528
```

FIGURE 4

```
ACGATATCCT GTAAGACCAA GAATTGCAAG GCCAGAGTTT GAATTCTTAT ACAAATGGAG CGTATGGTCC ACAATACCCC CCAGGCCCTG   90
GGGCAATAC  TGCCTCATAC TCAGGGGCTT ATTATGCACC TGGTTATACT CAGACCAGTT ACTCCACAGA AGTTCCAAGT ACTTACCGTT  180
CATCTGGCAA CAGCCCAACT CCAGTCTCTC CCAGTCTA   TCCCCAGACA GACTGTCAAG ACTGAAGCAC CCCCTCTTAA GGGGCAGGTT  270
CCAGATATC  CCCCTTCACA GAACCCTGGA ATGACCCTGC CCCATTATCC TTATGGAGAT GGTATCGTA  GTGTTCCACA ATCAGGGCCA  360
                                                                 M  E  M  V  I  V  F  H  N  Q  R
ACTGTACGAC CACAAGAAAG ATGCGTGGGC TTCTCCTGGT GCTTATGGAA TGGGTGGCCG TTATCCCTGG CCTTCATCAG CGCCCTCAGC  450
 L  Y  D  H  K  K  D  A  W  A  S  P  G  A  Y  G  M  G  G  R  Y  P  W  P  S  S  A  P  S  A
ACCACCCGGC AATTCTACA  TGACTGAAAG TACTTCACCA TGGCTAGCA  TGGCTAGCA  CCAGTCCAGT GTGGCTCTCC CCAGTCACCC  540
 P  P  G  N  S  T  W  L  Y  M  T  E  S  T  S  P  W  L  A  S  G  S  P  Q  S  P  P  V  Q  Q
GCCAAGGAT  TCTTCATACC CCTATAGCCA ATCAATCAA  GGCACAACTT CCTTGGAGTT ACAGATTCAA CCAGGATGTA AGGATCCTC   630
 A  K  D  S  S  Y  P  Y  S  Q  S  S  N  Q  G  T  T  S  L  E  L  Q  I  Q  P  G  C  S  D  P
GGGGACAGTG AACATCAGATC TTTCGATTCT CAGTCCAGT  ATATGCTGA  CAGTCCAGTA CCTTCAGATG AACTACTCCT CGGAGTATTA AAAAATTCAT  720
 G  D  S  E  H  Q  I  F  R  F  Q  V  Q  Y  M  L  T  V  Q  Y  L  Q  M  N  Y  S  S  E  Y
CCATCCCAAC AATCAGATC  AAATAGCAG   TCTTCCTGAA GATGTGTAC  CTTCAGATGA GACAGAACAA AGATACTGGC CGGAGTATGG CAAAAATCAT  810
 H  P  N  N  Q  I  K  S  S  L  P  E  D  V  Y  L  Q  M  R  Q  N  K  D  T  G  R  S  M  A  K  I
ACATGTGCTG GAGAGGGTAA AGTCTTGAA  ACAAGAGTA  ACAGGAGTTG AAGAGATTG  TGGGAAAAA  GACATACTGG CTTCTGGAGA TTCTGGAAGA  900
 Y  M  C  W  R  G  K  V  L  E  T  R  V  T  G  V  E  E  I  W  K  K  D  I  L  A  S  G  D  S  G  R
AATGCTACC AGGAGACTTT TGGAAGTAGA TTCAGTTGAA ACTGGGGCC  AGGACTCTGT AGGACTGGCC AGAAAAGAGG CTGTTTGTAA   990
 M  L  T  K  E  L  L  E  L  D  S  V  E  T  G  Q  D  S  V  R  Q  A  R  K  E  A  V  C  K
GATTCAGGCC ATATTGGAAA                                                                             1010
 I  Q  A  I  L  E
```

FIGURE 5

```
GAGAATAAA AAATGAACTT CTCCAAGCAC AAAACCCTTC TGAATTGTAC CTGAGCTCCA AAACAGAATT GCAGGGTTTA ATTGGACAGT        90
 E  I  K  N  E  L  L  Q  A  Q  N  P  S  E  L  Y  L  S  S  K  T  E  L  Q  Q  L  I  G  Q  L

TGGATGAGGT AAGTNTTGAA AAAACCCCT GCATCCGGGA AGCCAGGAGA AGAGCAGTGA TCGAGGTGCA AACTCTGATC ACATATATTG       180
 D  E  V  S  X  E  K  N  P  C  I  R  E  A  R  R  A  V  I  E  V  Q  T  L  I  Y  I  D

ACTTGAAGGA GGCCCTTGAG AAAGAAAGC TGTTTGCTTG TGAGGAGCAC CCATCCCATA AAGCCGTCTG GAAGCTCCTT GGAAACTTGT       270
 L  K  E  A  L  E  K  R  K  L  F  A  C  E  E  H  P  S  H  K  A  V  W  N  L  G  N  L  S

CTGAGATCCA GGGAGAGGTT CTTTCATTTG ATGGAAATCG AACCGATAAG AACTACATCC GGCTGGAAGA GCTGCTCACC AAGCAGCTGC       360
 L  E  I  Q  G  E  V  L  S  F  D  G  N  R  T  D  K  N  Y  I  R  L  E  E  L  L  T  K  Q  L  L

TAGCCCTGGA TGCTGTTGAT CCGCAGGGAG AAGAGAAGTG TAAGGCTGCC AGGAAACAAG CTGTGAGGCT ACTTTTGATA ATTCTCAGCT       450
 A  L  D  A  V  D  P  Q  G  E  E  K  C  K  A  A  R  K  Q  A  V  R  L  L  L  I  I  L  S  Y

ATCTCAGCT GAATCTGAT GAATGGAAGT ACTGAAATAC CAGAGATCTC ACTTTTGATA CTGTTTTGCA CTTCATATGT GCTTCATATGT       540
 L  D  L  K  S  D  E  W  E  Y

ATAGAGAGCT TTCAGTTCAT TGATTTATAC GTGCATATTT CAGTCTCAGT ATTATGATT GAAGCAAATT CTATTCAGTA TCTGCTGCTT       630

TTGATGTTGC AAGACAAATA TCATTACAGC ACGTTAACTT TTCCATTCGG ATCAAAAAA                                        689
```

FIGURE 6A

ATGTCTTTCCGCCTCTTCGTTGAAATATTTCACTTTCTTTTCCAGCTTTTTCCCCATCTCGACCT
GCTTTGGTTTTT
CGAGAAAACCACGTTCCAAATCAGCGACATCTCTCAAATTGAGATCATAGGCTTTTTGAAGATTG
CTCAAATTATG
CTTCTCATATTGCATGAGCATTTTGAAGCCCGCGTCATCAACCAAAGCATTTTTTCCACCCATCA
CAATGATTTTAT CATTTTCTTTAAAATT

FIGURE 6B

| | | | | | |
|---|---|---|---|---|---|
| MKVNVSCSSV | QTTIDILEEN | QGEDESILTL | GQLRDRIATD | NDVDVETMKL | 50 |
| LHRGKFLQGA | DDVSLSTLNF | KENDKIIVMG | GKNALVDDAG | FKMLMQYEKH | 100 |
| NLSNLQKAYD | LNLRDVADLE | RGFLEKPKQV | EMGKKLEKKV | KYFNEEAERH | 150 |
| LETLDGMNII | TETTPENQAK | RNREKRKTLV | NGIQTLLNQN | DALLRRLQEY | 200 |
| QSVLNGDIPE | | | | | 210 |

FIGURE 7A

```
ATGCCAGTCG TGAACATACC AATCAAAATA CTTGGTCAGA ATCAATCACA    50
TAGTCGAAGT AACTCCTCGT CTTCTGTTGA CAACGATCGA AATCAACCAC   100
CACAGCAGCC ACCTCAACCG CAACCACAAC AGCAATCTCA GCAACAATAC   150
CAGCAGGCTC CAAACGTGAA TACCAATATG CATCATTCCA ACGGATTCTC   200
ACCTAACTTC CCATCTCGTA GTCCTATTCC GGACTTTCCC AGTTTTTCAT   250
CTGGGTTCCC AAACGATTCT GAATGGTCTT CGAATTTCCC GTCGTTTCCA   300
AATTTCCCAA GTGGATTCTC AAATGGAAGT TCTAATTTCC CTGATTTTCC   350
AAGATTCGGA AGAGATGGAG GACTATCGCC AAACCCACCG ATGCAAGGAT   400
ACAGGAGAAG TCCAACACCA ACATCAACTC AATCTCCAAC TTCTACATTA   450
AGACGCAACT CTCAGCAGAA TCAAGCTCCT CCACAATATT CTCAGCAACA   500
ACCACAACAA GCTCAACAAC GTCAGACAAC TCCTCCGTCA ACAAAAGCTT   550
CATCTCGACC ACCATCTCGT ACTCGTGAAC CAAAGGAACC TGAGGTACCC   600
GAGAGACCAG CAGTTATTCC ATTGCCATAT GAGAAGAAGG AGAAACCACT   650
GGAGAAGAAA GGTAGTCGTG ATTCTGGAAA GGGTGATGAG AACCTTGAAG   700
AGAACATTGC CAAGATCACG ATCGGAAAGA ATAATTGCGA GTTATGTCCG   750
GAACAAGAAA CGGACGGCGA CCCATCTCCA CTAACCTCCC CAATCACCGA   800
AGGAAAGCCA AAGAGAGGAA AGAAACTTCA ACGTAATCAA AGTGTTGTTG   850
ATTTCAATGC CAAGACAATT GTTACTTTGG ATAAAATTGA ATTACAAGTT   900
GAGCAGTTGA GAAAAAAAGC TGCTGAACTC GAAATGGAAA AAGAGCAAAT   950
TCTTCGTTCT CTAGGAGAAA TCAGTGTTCA TAACTGCATG TTCAAACTGG  1000
AAGAATGTGA TCGTGAAGAG ATTGAAGCAA TCACTGACCG ATTGACAAAA  1050
AGAACAAAGA CAGTTCAAGT TGTTGTCGAA ACTCCACGAA ATGAAGAACA  1100
GAAAAAAGCA CTGGAAGATG CAACTTTGAT GATCGATGAA GTCGGAGAAA  1150
TGATGCATTC GAATATTGAA AAGGCTAAGC TGTGCCTACA AACCTACATG  1200
AACGCCTGTT CGTACGAAGA AACTGCTGGA GCCACCTGCC AAAACTTCTT  1250
GAAGATCATA ATTCAGTGCG CTGCTGATGA TCAGAAACGC ATCAAGCGTC  1300
GTCTGGAAAA TCTGATGTCT CAAATTGAGA ATGCTGAGAG AACGAAAGCA  1350
GATTTGATGG ATGATCAAAG CGAATAG                           1377
```

FIGURE 7B

```
MPVVNIPIKI LGQNQSHSRS NSSSSVDNDR NQPPQQPPQP QPQQQSQQQY        50
QQAPNVNTNM HHSNGFSPNF PSRSPIPDFP SFSSGFPNDS EWSSNFPSFP       100
NFPSGFSNGS SNFPDFPRFG RDGGLSPNPP MQGYRRSPTP TSTQSPTSTL       150
RRNSQQNQAP PQYSQQQPQQ AQQRQTTPPS TKASSRPPSR TREPKEPEVP       200
ERPAVIPLPY EKKEKPLEKK GSRDSGKGDE NLEENIAKIT IGKNNCELCP       250
EQETDGDPSP LTSPITEGKP KRGKKLQRNQ SVVDFNAKTI VTLDKIELQV       300
EQLRKKAAEL EMEKEQILRS LGEISVHNCM FKLEECDREE.IEAITDRLTK       350
RTKTVQVVVE TPRNEEQKKA LEDATLMIDE VGEMMHSNIE KAKLCLQTYM       400
NACSYEETAG ATCQNFLKII IQCAADDQKR IKRRLENLMS QIENAERTKA       450
DLMDDQSE                                                     458
```

FIGURE 8A

```
ATGTCAGAAA AGACTAGCAC AGTTACAATA CACTATGGAA ATCAGCGATT    50
TCCGGTAGCA GTCAATCTAA ATGAGACGTT AAGTGAACTG ATTGATGATT   100
TACTTGAAAC GACTGAGATT TCTGAGAAGA AAGTCAAGCT TTTTTACGCT   150
GGCAAGCGTT TAAAAGACAA AAAAGCCTCG TTATCAAAAT TGGGTTTAAA   200
AAATCATAGT AAAATTCTAT GTATAAGACC ACATAAGCAA CAACGAGGTT   250
CCAAGGAAAA AGACACGGTT GAGCCCGCTC CGAAAGCGGA AGCGGAGAAT   300
CCTGTATTTT CGCGTATTTC TGGAGAAATA AAAGCCATCG ATCAGTATGT   350
TGACAAAGAA CTTTCCCCCA TGTACGACAA TTACGTAAAT AAACCGTCGA   400
ACGATCCAAA GCAGAAAAAC AAACAGAAAC TAATGATAAG TGAACTACTT   450
TTACAACAGC TTTTAAAATT GGATGGAGTT GACGTACTGG GCAGCGAGAA   500
ATTGCGTTTT GAACGGAAGC AACTTGTTTC TAAGATCCAA AAAATGTTGG   550
ATCACGTTGA CCAAACAAGC CAAGAAGTGG CCGCATAG               588
```

FIGURE 8B

```
MSEKTSTVTI HYGNQRFPVA VNLNETLSEL IDDLLETTEI SEKKVKLFYA       50
GKRLKDKKAS LSKLGLKNHS KILCIRPHKQ QRGSKEKDTV EPAPKAEAEN      100
PVFSRISGEI KAIDQYVDKE LSPMYDNYVN KPSNDPKQKN KQKLMISELL      150
LQQLLKLDGV DVLGSEKLRF ERKQLVSKIQ KMLDHVDQTS QEVAA           195
```

FIGURE 9A

```
ATGTCTTTTT TTACCCAGTT GTGTTCTATG GATAAAAAAT ATTGGATCTC      50
TCTAGCTGTA TTGTCAGTTA CTGTTTTGAT TAGCGCATTA TTGAAAAAGA     100
GAGCTACTGA AACCGAAGAT ATTGTCGTTG TTCATTACGA TGGCGAAAAG     150
TTGAATTTTG TGTTGCGACA ACCAAGGCTG AATATGGTTT CTTACACTAG     200
TTTTCTTCGT CGCGTGTGCA ACGCATTTTC AGTAATGCCC GACAAAGCGT     250
CTCTCAAGTT AAACGGGTG ACCCTCAAGG ATGGTTCACT TTCCGACCAA      300
AATGTGCAAA ATGGAAGTGA ATTAGAGCTC GAATTACCCA AACTGAGCCC     350
GGCAATGCAA CAAATTGAAG CATATATAGA TGAGCTTCAA CAGGATCTCG     400
TCCCTAAAAT TGAAGCCTTC TGCCAATCGT CTCCCGCTTC GGCACAAGAT     450
GTTCAAGATT TGCATACACG CCTTAGTGAA ACATTGTTGG CTAGGATGAT     500
AAAATTAGAT GCTGTTAATG TTGAAGACGA CCCAGAAGCT CGTCTTAAAA     550
GAAAAGAAGC TATTCGTTTA TCTCAACAAT ATTTGAGTAA ACTAGATTCC     600
ACCAAGAATC AAAACAAATG A                                    621
```

FIGURE 9B

```
MSFFTQLCSM DKKYWISLAV LSVTVLISAL LKKRATETED IVVVHYDGEK     50
LNFVLRQPRL NMVSYTSFLR RVCNAFSVMP DKASLKLNGV TLKDGSLSDQ    100
NVQNGSELEL ELPKLSPAMQ QIEAYIDELQ QDLVPKIEAF CQSSPASAQD    150
VQDLHTRLSE TLLARMIKLD AVNVEDDPEA RLKRKEAIRL SQQYLSKLDS    200
TKNQNK                                                    206
```

| | |
|---|---|
| GCGGAGCTCC GCATCCAACC CGGGGCCGCG GCCAACTTCT CTGGACTGGA | 50 |
| CCAGAAGTTT CTAGCCGGCC AGTTGCTACC TCCCTTATC TCCTCCTTCC | 100 |
| CCTCTGGCAG CGAGGAGGCT ATTTCCAGAC ACTTCCACCC CTCTCTGGCC | 150 |
| ACGTCACCCC CGCCTTTAAT TCATAAAGGT GCCCGGCGCC GGCTTCCCGG | 200 |
| ACACGTCCGG GCGGAGAGG GGCCCACGGC GGCGGCCGG CCAGAGACTC | 250 |
| GGCGCCCGGA GCCAGCCGCC CGCACCGGCG CCCAGCGGG CAGACCCCAA | 300 |
| CCCAGCATGA GCGCCGCCAC CCACTCGCCC ATGATGCAGG TGGCGTCCGG | 350 |
| CAACGGTGAC CGCGACCCTT TGCCCCCCGG ATGGGAGATC AAGATCGACC | 400 |
| CGCAGACCGG CTGCCCCTC TTCGTGGACC ACAACAGCCG CACCACTACG | 450 |
| TGGAACGACC CGCGCGTGCC CTCTGAGGGC CCCAAGGAGA CTCCATCCTC | 500 |
| TGCCAATGGC CCTTCCCGGG AGGGCTCTAG GCTGCCGCCT GCTAGGGAAG | 550 |
| GCCACCCTGT GTACCCCCAG CTCCGACCAG GCTACATTCC CATTCCTGTG | 600 |
| CTCCATGAAG GCGCTGAGAA CCGGCAGGTG CACCCTTCC ATGTCTATCC | 650 |
| CCAGCCTGGG ATGCAGCGAT TCCGAACTGA GGCGGCAGCA GCGGCTCCTC | 700 |
| AGAGGTCCCA GTCACCTCTG CGGGCATGC CAGAAACCAC TCAGCCAGAT | 750 |
| AAACAGTGTG GACAGGTGGC AGCGGGGGCG GCAGCCCAGC CCCAGCCTC | 800 |
| CCACGGACCT GAGCGGTCCC AGTCTCCAGC TGCCTCTGAC TGCTCATCCT | 850 |
| CATCCTCCTG GGCCAGCCTG CCTTCCTCCG GCAGGAGCAG CCTGGGCAGT | 900 |
| CACCAGGTCC CGCGGGGGTA CATCTCCATT CCGGTGATAC ACGAGCAGAA | 950 |
| CGTTACCCGG CCAGCAGCC AGCCCTCCTT CCACAAAGCC CAGAAGACGC | 1000 |
| ACTACCCAGC GCAGAGGGT GAGTACCAGA CCCACCAGCC TGTGTACCAC | 1050 |
| AAGATCCAGG GGGATGACTG GAAGCCCCGG CCCTGCGGG CGGCATCCCC | 1100 |
| GTTCAGGTCA TCTGTCCAGG GTGCATGGAG CGGGAGGGC TCACCAGCCA | 1150 |
| GGAGCAGCAC GCCACTCCAC TCCCCTCGC CCATGACCCAT GCACACCGTG | 1200 |
| GTCGACAGGC CTCAGCAGCC CATGACCCAT CGAGAAACTG CACCTGTTTC | 1250 |
| CCAGCCTGAA AACAAACCAG AAAGTAAGCC AGGCCCAGTT GGACCAGAAC | 1300 |
| TCCCTCCTGG ACACATCCCA ATTCAAGTGA TCCGCAAAGA GGTGGATTCT | 1350 |

FIGURE 15A

```
AAACCTGTTT CCCAGAAGCC CCCACCTCCC TCTGAGAAGG TAGAGGTGAA      1400
AGTTCCCCCT GCTCCAGTTC CTTGTCCTCC TCCCAGCCCT GGCCCTTCTG      1450
CTGTCCCCTC TTCCCCCAAG AGTGTGGCTA CAGAAGAGAG GGCAGCCCCC      1500
AGCACTGCCC CTGCAGAAGC TACACCTCCA AAACCAGGAG AAGCCGAGGC      1550
TCCCCAAAA CATCCAGGAG TGCTGAAAGT GGAAGCCATC CTGGAGAAGG       1600
TGCAGGGGCT GGAGCAGGCT GTAGACAACT TTGAAGGCAA GAAGACTGAC      1650
AAAAAGTACC TGATGATCGA AGAGTATTTG ACCAAAGAGC TGCTGGCCCT      1700
GGATTCAGTG GACCCGAGG GACGAGCCGA TGTGCGTCAG GCCAGGAGAG       1750
ACGGTGTCAG GAAGGTTCAG ACCATCTTGG AAAAACTTGA ACAGAAAGCC      1800
ATTGATGTCC CAGGTCAAGT CCAGGTCTAT GAACTCCAGC CCAGCAACCT      1850
TGAAGCAGAT CAGCCACTGC AGGCAATGCT GGTGAAATG CAGAAGATCC       1900
CAGACAAGG CAAGAAAAAT GCTGGAAATG CAGAAGATCA CCACACAGAA       1950
ACCCAGCAGC CAGAAGCCAC AGCAGCACC ACTTCAAACC CCAGCAGCAT       2000
GACAGACACC CCTGGTAACC CAGCAGCACC GTAGCCTCTG CCCTGTAAAA      2050
ATCAGACTCG GAACCGATGT GTGCTTAAGG GAATTTTAAG TTGCATGCAT      2100
TTCAGAGACT TTAAGTCAGT TGGTTTTTAT TAGCTGCTTG GTATGCAGTA      2150
ACTTGGGTGG AGGCAAAACA CTAATAAAAG GGCTAAAAAG GAAAATGATG      2200
CTTTTCTTCT ATATTCTTAC TCTGTACAAA TAAAGAAGTT GCTTGTTGTT      2250
TGAGAAGTTT AACCCCGTTG CTTGTTCTGC AGCCCTGTCT ACTTGGGCAC      2300
CCCCACCACC TGTTAGCTGT GGTTGTGCAC TGTCTTTTGT AGCTCTGGAC      2350
TGGAGGGGTA GATGGGGAGT CAATTACCCA TCACATAAAT ATGAAACATT      2400
TATCAGAAAT GTTGCCATTT TAATGAGATG ATTTTCTTCA TCTCATAATT     2450
AAAATACCTG ACTTTAGAGA GAGTAAAATG TGCCAGGAGC CATAGGAATA      2500
TCTGTATGTT AATGCTACTT TTTC                                 2534
```

FIGURE 15B

```
MSAATHSPMM QVASGNGDRD PLPPGWEIKI DPQTGWPFFV DHNSRTTTWN    50
DPRVPSEGPK ETPSSANGPS REGSRLPPAR EGHPVYPQLR PGYIPIPVLH   100
EGAENRQVHP FHVYPQPGMQ RFRTEAAAAA PQRSQSPLRG MPETTQPDKQ   150
CGQVAAAAAA QPPASHGPER SQSPAASDCS SSSSSASLPS SGRSSLGSHQ   200
LPRGYISIPV IHEQNVTRPA AQPSFHKAQK THYPAQRGEY QTHQPVYHKI   250
QGDDWEPRPL RAASPFRSSV QGASSREGSP ARSSTPLHSP SPIRVHTVVD   300
RPQQPMTHRE TAPVSQPENK PESKPGPVGP ELPPGHIPIQ VIRKEVDSKP   350
VSQKPPPPSE KVEVKVPPAP VPCPPPSPGP SAVPSSPKSV ATEERAAPST   400
APAEATPPKP GEAEAPPKHP GVLKVEAILE KVQGLEQAVD NFEGKKTDKK   450
YLMIEEYLTK ELLALDSVDP EGRADVRQAR RDGVRKVQTI LEKLEQKAID   500
VPGQVQVYEL QPSNLEADQP LQAIMEMGAV AADKGKKNAG NAEDPHTETQ   550
QPEATAAATS NPSSMTDTPG NPAAP                             575
```

| | |
|---|---|
| CGGTGGGAGC GGGGCGGGAA GCGCTTCAGG GCAGCGGATC CCATGTCGGC | 50 |
| CCTGAGCGCT TCGGGCTACG GCCCAGTGA CGGTCCGTCC TACGGCCGCT | 100 |
| ACTACGGGCC TGGGGGTGGA GATGTGCCGG TACACCCACC TCCACCCTTA | 150 |
| TATCCTCTTC GCCCTGAACC TCCCCAGCCT CCCATTTCCT GGCGGGTGCG | 200 |
| CGGGCGGCGC CCGGCGGAGA CCAACTGGCT GGGAGAAGGC GGAGGAGGCG | 250 |
| ATGGCTACTA TCCCTCGGGA GGCGCCTGGC CAGAGCCTGG TCGAGCCGGA | 300 |
| GGAAGCCACC AGGAGCAGCC ACCATATCCT AGTACAATT CTAACTATTG | 350 |
| GAATTCTACT GCGAGATCTA GGGTCCTTA CCCAAGTACA TATCCTGTAA | 400 |
| GACCAGAATT GCAAGGCCAG AGTTTGAATT CTTATACAAA TGGAGCGTAT | 450 |
| GGTCCAACAT ACCCCCCAGG CCCTGGGGCA AATACTGCCT CATACTCAGG | 500 |
| GGCTTATTAT GCACCTGGTT ATACTCAGAC CAGTACTCC ACAGAAGTTC | 550 |
| CAAGTACTTA CCGTTCATCT GGCAACAGCC CAACTCCAGT CTCTCGTTGG | 600 |
| ATCTATCCCC AGCAGGACTG TCAGACTGAA GCACCCCTC TTAGGGGCA | 650 |
| GGTTCCAGGA TATCCGCCTT CACAGAACCC TGGAATGACC CTGCCCCATT | 700 |
| ATCCTTATGG AGATGGTAAT CGTAGTGTTC CACAATCAGG ACGACTGTA | 750 |
| CGACCACAAG AAGATGCGTG GGCTTCTCCT GGTGCTTATG GAATGGGTGG | 800 |
| CCGTTATCCC TGGCCTTCAT CAGCGCCCTC AGCACCACC GGCAATCTCT | 850 |
| ACATGACTGA AAGTACTTCA CCATGGCCTA GCAGTGGCTC TCCCAGTCA | 900 |
| CCCCCTTCAC CCCAGTCCA GCAGCCCAAG GATTCTTCAT ACCCCTATAG | 950 |
| CCAATCAGAT CAAAGCATGA ACCGGCACAA CTTTCCTTGC AGTGTCCATC | 1000 |
| AGTACGAATC CTCGGGACA GTGATCAATG AAGATTCAGA TCTTTTGGAT | 1050 |
| TCCCAGTCC AGTATAGTGC TGAGCCTCAG CTGTATGGTA ATGCCACCAG | 1100 |
| TGACCATCCC AACAATCAAG ATCAAAGTAG CAGTCTTCCT GAAGAATGTG | 1150 |
| TACCTTCAGA TGAAAGTACT CCTCCGAGTA TTAAAAAAAT CATACATGTG | 1200 |
| CTGGAGAAGG TCCAGTATCT TGAACAAGAA GTAGAAGAAT TTGTAGGAAA | 1250 |
| AAAGACAGAC AAAGCATACT GGCTTCTGGA AGAAATGCTA ACCAAGGAAC | 1300 |

FIGURE 16A

```
TTTTGGAACT GGATTCAGTT GAAACTGGGG GCCAGGACTC TGTACGGCAG    1350
GCCAGAAAAG AGGCTGTTTG TAAGATTCAG GCCATACTGG AAAAATTAGA    1400
AAAAAAGGA TTATGAAAGG ATTAGAACA AAGTGGAAGC CTGTTACTAA      1450
CTTGACCAAA GAACACTTGA TTAGGTTAAT TACCCTCTTT TTGAAATGCC    1500
TGTTGATGAC AAGAAGCAAT ACATTCCAGC TTTTCCTTTG ATTTTATACT    1550
TGAAAACTG GCAAAGGAAT GGAAGAATAT TTTAGTCATG AAGTTGTTTT     1600
CAGTTTTCAGA CGAATGAATG TAATAGGAAA CTATGGAGTT ACCAATATTG   1650
CCAAGTAGAC TCACTCCTTA AAAATTTAT GGATATCTAC AAGCTGCTTA     1700
TTACCAGCAG GAGGAAACA CACTCCACAC AACAGGCTTA TCAGAAACCT     1750
ACCAGATGAA ACTGGATATA ATTTGAGACA AACAGGATGT GTTTTTTAA     1800
ACATCTGGAT ATCTTGTCAC ATTTTGTAC ATTGTGACTG CTTTCAACAT     1850
ATACTTCATG TGTAATTATA GCTAGACTT TAGCCTTCTT GGACTTCTGT     1900
TTGTTTTGT TATTTGCAGT TTACAAATAT AGTATTATTC TCTAAAAA       1950
AAAAAAAAA  AAAAAA                                         1966
```

FIGURE 16B

MSALRRSGGYGPSDGPSYGRYYGPGGGDVPVHPPPPLYPLRPEPPQPPISWRVRGGGPAETTVLGEGGGGDGYYPSGGAWP
EPGRAGGSHQEQPPYPSYNSNYVVNSTARSRAPYPSTYVRPELQGQSLNSYTNGAYGPTYPPGPGANTASYSGAYYAPGY
TQTSYSTEVPSTYRSSGNSPTPVSRWVYPQQDCQTEAPPLRGQVPGYPPSQNPGMTLPHYPYGDGNRSVPQSGPTVRPQE
DAWASPGAYGMGGRYPWPSSAPSAPPGNLYMTESTSPWPSSGSPQSPPSPPVQQPKDSSYPYSQSDQSMNRHNFPCSVHQ
YESSGTVINEDSDLLDSQVQYSAEPQLYGNATSDHPNNQDQSSSLPEECVPSDESTPPSIKKIIHVLEKVQYLEQEVEEF
VGKKTDKAYWLLEEMLTKELLELDSVETGGQDSVRQARKEAVCKIQAILEKLEKKGL

| | |
|---|---|
| CCCCCCCCCC CCCCCCCCCC CCNGAAGACG CCCGGAGCGG CTGCTGCAGC | 50 |
| CAGTAGCGGC CCCTTCACCG GCTGCCCGC TCAGACCTAG TCGGGAGGGG | 100 |
| TGCGAGGCAT GCAGCTGGGG GCCCAGCTCC GGTGCCGCAC CCCGTAAAGG | 150 |
| GCTGATCTTC CACCTCGCCA CCTCAGCCAC GGGACGCCAA GACCGCATCC | 200 |
| AATTCAGACT TCTTTGGTG CTTGTGAAAC TGAACACAAC AAAAGTATGG | 250 |
| ATATGGGAAA CCAACATCCT TCTATTAGTA GGCTTCAGGA AATCCAAAAG | 300 |
| GAAGTAAAAA GTGTAGAACA GCAAGTTATC GGCTTCAGTG GTCTGTCAGA | 350 |
| TGACAAGAAT TACAAGAAAC TGGAGAGGAT TCTAACAAAA CAGCTTTTG | 400 |
| AAATAGACTC TGTAGATACT GAAGGAAAAG GAGATATTCA GCAAGCTAGG | 450 |
| AAGCGGGCAG CACAGGAGAC AGAACGTCTT CTCAAAGAGT TGGAGCAGAA | 500 |
| TGCAAACCAC CCACACCGGA TTGAAATACA GAACATTTT GAGGAAGCCC | 550 |
| AGTCCCTCGT GAGAGAGAAA ATTGTGCCAT TTTATAATGG AGGCAACTGC | 600 |
| GTAACTGATG AGTTTGAAGA AGGCATCCAA GATATCATTC TGAGGCTGAC | 650 |
| ACATGTTAAA ACTGGAGGAA AAATCTCCTT GCGGAAAGCA AGGTATCACA | 700 |
| CTTAACCAA AATCTGTGCG GTGCAAGAGA TAATGGAAGA CTGCATGAAA | 750 |
| AAGCAGCCTT CCCTGCCGCT TCCGAGGAT GCACATCCT CCGTTGCCAA | 800 |
| AATCAACTTC GTGATGTGTG AGGTGAACAA GGCCCGAGGG GTCCTGATTG | 850 |
| CACTTCTGAT GGGTGTGAAC AACAATGAGA CCTGCAGGCA CTTATCCTGT | 900 |
| GTGCTCTCGG GGCTGATCGC TGACCTGGAT GCTCTAGAGG TGTGCGCCG | 950 |
| GACAGAAATC AGAAATTATC GGAGGGAGGT AGTAGAAGAT ATCAACAAAT | 1000 |
| TATTGAAATA TCTGGATTTG GAAGAGGAAG CAGACACAAC TAAAGCATTT | 1050 |
| GACCTGAGAC AGAATCATTC CATTTAAAA ATAGAAAAGG TCCTCAAGAG | 1100 |
| AATGAGAGAA ATAAAAAATG AACTTCTCCA AGCACAAAAC CCTTCTGAAT | 1150 |
| TGTACCTGAG CTCCAAAACA GAATTGCAGG GTTAATTGG ACAGTTGGAT | 1200 |
| GAGGTAAGTC TTGAAAAAAA CCCCTGCATC CGGAAGCCA GGAGAAGAGC | 1250 |
| AGTGATCGAG GTGCAAACTC TGATCACATA TATTGACTTG AAGGAGCCC | 1300 |

FIGURE 17A

```
TTGAGAAAAG AAAGCTGTTT GCTTGTGAGG AGCACCCATC CCATAAAGCC    1350
GTCTGGAACG TCCTTGGAAA CTTGTCTGAG ATCCAGGGAG AAGTTCTTTC    1400
ATTTGATGGA AATCGAACCG ATAAGAACTA CATCCGGCTG GAAGAGCTGC    1450
TCACCAAGCA GCTGCTAGCC CTGGATGCTG TTGATCCGCA GGGAGAAGAG    1500
AAGTGTAAGG CTGCCAGGAA ACAAGCTGTG AGGCTTGCGC AGAATATTCT    1550
CAGCTATCTC GACCTGAAAT CTGATGAATG GGAGTACTGA AATACCAGAG    1600
ATCTCACTTT TGATACTGTT TGCACTCA TATGTGCTC TATGTATAGA       1650
GAGCTTTCAG TTCATTGATT TATACGTGCA TATTTCAGTC TCAGTATTTA    1700
TGATTGAAGC AAATTCTATT CAGTATCTGC TGCTTTGAT GTTGCAAGAC     1750
AAATATCATT ACAGCACGTT AACTTTTCCA TTCGGATCAT TATCTGTATG    1800
ATGTGGTGTG GTTTGTTTGG TTTGTCCTTT TTTTGCGTT TTTAATCAGA     1850
AAACAAAATA GAGGCAGCTT TTGTAGATTT TAAATGGGT GTGCAAGCAT     1900
TAAAATGCAG GTCTTTCAGA ATCTAGAACT AGGCATAACC TTACATAATA    1950
CTAGGAAAAT TATGAGAAAG GGGAAATTTT TGGTTAAATA AGAGTAAGGT    2000
TCAAACACAA GCAGTACATG TTCTGTTTCA TTATGCTCGA TAGAAGGCTT    2050
TTTTTTCACT TATAAGGCCT GATTGGTCCT ACCCAGCTTA ACGGGGTGGG    2100
GTTTTTTGT TTGTTCAGAC AGTCTGTTCT TTTGTAAACA TTTTTAGTTG    2150
GAAAAACAGC ATCTGCATTT TCCCCATCCT CTACGTTTTA GAGAGGAATC    2200
TTGTTTTGT GTGCAACATA AGAAAATTAT GAAAACTAAT AGCCAAAAAA     2250
CCTTTGAGAT TGCATTAAAG AGAAGGGATA AAGGACCAGC AATAATACCT    2300
TGTAAGTTGC TTTTGTTTGT AAAATCTGAG CTTATAGTTT TCCTTAGTGA    2350
GTAAATTCAT AAGGATGGGA ACATTTAAAT TAAGTTAATG GGCCTTTAAA    2400
AAAAAAAAG GAAACACTCA TACCTGTAGT TGGAGGATGA ATACTGGAGA     2450
CGGGTTACCA ATGTCAGGTT ATACTAAAAC TAAATCAGAA AGTCTGAATG    2500
TAGCACATAA TGGTTCTCTT CTGTTGTCCA AGGCTGTAAA ATGGACAGCC    2550
TTGTCACACC TCCCGGTGC TGTTTTACAA CGTGAGGGTA GACGCTGTCA     2600
```

FIGURE 17A

```
GTAACCCAGA GGGACCAGGC CTTCCTAGGT TTTCTAGGCA GTCAGCTGTT    2650
AACCACTCAC TTAGTAAATG TCATAACTAC ACCTGCTCCA GGACCAATCA    2700
GTGAAACCTG CTCGGAATTA AAGGCTTCCT CTGGGTGCCT GCTGAACAAC    2750
TGAGCTCATG TCATGGGCAT GTGGTGGTTT CTCTGTTGCC TGAAAGAGCC    2800
ATTAAAGTCA GTCGTGCGTG AAGCATGTCT CTTCTAAAGG ATGTGTATTT    2850
CCATAAATGC TTTCTGAGGA TCCGGTACAA AATGATTTCC CAAAGTTCTG    2900
AAGTGCCTTG AGAACATGTG GGTCCGAGTG TTATAACAGA CTCCTCCCCC    2950
GGGTCACCTT TGCCTGGTC ATCCTGTTAG AGTACATCTT TGGAAATCCA     3000
GGGTAATATT CTCTTTCAGA GATGCTCATT GTGTAACTCT GTGTAGGGAG    3050
ATAGTCACTT TAAACAGCTC AAAGTAGCTA GCTAAAGGAG TAGCCTTAAA    3100
TACCTAAAAG ATGACAGAAG CATAGCCCTT AACAAATCTT CAGCTTGTCT    3150
CTCAGTATTT CCCAATCATG AAAATCCCT GCTATGTCTT TCCTACTAGA     3200
AATGTTCTAG AATCGCTGAA CGGTGGGGTC AGAGGGCAGT CGGTATTTAG    3250
GCCGTGAGCT TCCCATACTA CTGCAGGTCC AACTCCTGGC AACCGCGGGC    3300
TCAAGGCAGG TCATTGGAAT CCACGTTTTG GCCACAGTAG TTGTAGGATT    3350
GCTTTTCTGT ATCATAATTT TAGAATGCTC TTAAAATCTT GAGGAAGAGT    3400
TTTATTTT TATTTATTTT TGAGATGGAG TCTCTGTTGC CCAGGCTGCA      3450
GTGCAGTGGT GCCATCTCAG CTCACTGCAA CCTCCACCTC CCAGGTTCAA    3500
GCGATTCTCC TGCCTCAGCC ACCTGAGTAG CTGGGAGTAC AGGCATGTGG    3550
CACCACGCCT GGCTAATTTT TGTATTTTTA ATAGAGTTGA GATTTCACCA    3600
TGATGGTCAG GCTGGTCTCG AACTCCTGAC CTCGTGATCC GCCCGCCTCG    3650
GCCCCCAAA GTGCTGGGAT TAACGGGTGT GAGCCACGGC GCCAGCCCA      3700
GGAAGAGTTT TTAAATTAGA GCTCTGTTTA ATTATACCAC TGGGAAATCA    3750
TGGTTACGCT TCAGGCATAT TCTTCCCCAG AGTACTACTT ACATTTTAAA    3800
TTTCATTTTG TAAAGTTAAA TGTCAGCATT CCCTTAAAA GTGTCCATTG     3850
TTCTTTGAAA GTAGACGTTT CAGTCATTCT TTCAAACAA GTGTTTGTGT     3900
```

FIGURE 17A

```
ACCTTTTGCC AAGCTGTGGG CATCGTGTGT GAGTACAGGG TGCTCAGCTC    3950
TTCCACCGTC ATTTGAATT GTTCACATGG GTAATTGGTC ATGGAAATGA     4000
TCAGATTGAC CTTGATTGAC TGTCAGGCAT GGCTTTGTTT CTAGTTTCAA    4050
TCTGTTCTCG TTCCTTGTAC CGGATTATTC TACTCCTGCA ATGAACCCTG    4100
TTGACACCGG ATTTAGCTCT TGTCGGCCTT CGTGGGGAGC TGTTTGTGTT    4150
AATATGAGCT ACTGCATGTA ATTCTTAAAC TGGGCTTGTC ACATTGTATT    4200
GTATTTTTGT GATCTGTAAT GAAAAGAATC TGTACTGCAA GTAAAACCTA    4250
CTCCCCAAAA ATGTGTGGCT TTGGGTCTGC ATTAAACGCT GTAGTCCATG    4300
TTCATGCC                                                   4308
```

FIGURE 17B

```
MDMGNQHPSI SRLQEIQKEV KSVEQQVIGF SGLSDDKNYK KLERILTKQL    50
FEIDSVDTEG KGDIQQARKR AAQETERLLK ELEQNANHPH RIEIQNIFEE   100
AQSLVREKIV PFYNGGNCVT DEFEEGIQDI ILRLTHVKTG GKISLRKARY   150
HTLTKICAVQ EIIEDCMKKQ PSLPLSEDAH PSVAKINFVM CEVNKARGVL   200
IALLMGVNNN ETCRHLSCVL SGLIADLDAL DVCGRTEIRN YRREVVEDIN   250
KLLKYLDLEE EADTTKAFDL RQNHSILKIE KVLKRMREIK NELLQAQNPS   300
ELYLSSKTEL QGLIGQLDEV SLEKNPCIRE ARRRAVIEVQ TLITYIDLKE   350
ALEKRKLFAC EEHPSHKAVW NVLGNLSEIQ GEVLSFDGNR TDKNYIRLEE   400
LLTKQLLALD AVDPQGEEKC KAARKQAVRL AQNILSYLDL KSDEWEY     447
```

FIGURE 17C

[Figure showing DNA/protein sequence data - text too degraded/low-resolution to reliably transcribe]

BAG PROTEINS AND NUCLEIC ACID MOLECULES ENCODING THEM

This application claims the benefit of U.S. Provisional Application No. 60/155,212, filed Sep. 9, 1998, which was converted from U.S. Ser. No. 09/150,489, and now is abandoned, and which is incorporated herein by reference.

This invention was made with government support under grant number CA-67329 awarded by the National Institutes of Health and grant number DAMD17-99-1-9094 awarded by the United States Army. The United States Government has certain rights in this invention.

BACKGROUND OF THE INVENTION

1. Field of the Invention

This invention relates generally to the fields of molecular biology and molecular medicine and more specifically to a novel family of proteins that can regulate protein folding. The functions of these proteins are potentially diverse, including promoting tumor cell growth and metastasis.

2. Background Information

The Hsc70/Hsp70-family of molecular chaperones participate in protein folding reactions, controlling protein bioactivity, degradation, complex assembly/disassembly, and translocation across membranes. These proteins interact with hydrophobic regions within target proteins via a carboxyl (C)-terminal peptide binding domain, with substrate binding and release being controlled by the N-terminal ATP-binding domain of Hsc70/Hsp70. Hsc70/Hsp70-assisted folding reactions are accomplished by repeated cycles of peptide binding, refolding, and release, which are coupled to ATP hydrolysis by the ATP-binding domain (ATPase) of Hsc70/Hsp70 and by subsequent nucleotide exchange. The chaperone activity of mammalian Hsc70/Hsp70 is regulated by partner proteins that either modulate the peptide binding cycle or that target the actions of these chaperones to specific proteins and subcellular compartments. DnaJ-family proteins (Hdj-1/Hsp40; Hdj-2; Hdj-3) stimulate the ATPase activity of Hsc70/Hsp70, resulting in the ADP-bound state which binds tightly to peptide substrates. The Hip protein collaborates with Hsc70/Hsp70 and DnaJ homologues in stimulating ATP hydrolysis, and thus also stabilize Hsc70/Hsp70 complexes with substrate polypeptides, whereas the Hop protein may provide co-chaperone functions through interactions with the C-terminal peptide binding domain.

The Bcl-2 associated athanogene-1 (bag-1) is named from the Greek word athanos, which refers to anti-cell death. BAG-1 was previously referred to as Bcl-2-associated protein-1 (BAP-1) in U.S. Pat. No. 5,539,094 issued Jul. 23, 1996, which is incorporated herein by reference. In this earlier patent, BAG-1 is described as a portion of the human BAG-1 protein, absent the N-terminal amino acids 1 to 85. In addition, a human protein essentially identical to human BAG-1 was described by Zeiner and Gehring, (Proc. Natl. Acad. Sci., USA 92:11465–11469 (1995)). Subsequent to the issuance of U.S. Pat. No. 5,539,094 the N-terminal amino acid sequence from 1 to 85 of human BAG-1 was reported.

BAG-1 and its longer isoforms BAG-1M (Rap46) and BAG-1L are recently described Hsc70/Hsp70-regulating proteins. BAG-1 competes with Hip for binding to the Hsc70/Hsp70 ATPase domain and promotes substrate release. BAG-1 also reportedly stimulates Hsc70-mediated ATP hydrolysis by accelerating ADP/ATP exchange, analogous to the prokaryotic GrpE nucleotide exchange protein of the bacterial Hsc70 homologue, DnaK. Gene transfection studies indicate that BAG-1 proteins can influence a wide variety of cellular phenotypes through their interactions with Hsc70/Hsp70, including increasing resistance to apoptosis, promoting cell proliferation, enhancing tumor cell migration and metastasis, and altering transcriptional activity of steroid hormone receptors.

Despite the notable progress in the art, there remains an unmet need for the further identification and isolation of additional homologous BAG protein species, and the nucleic acid molecules and/or nucleotide sequences that encode them. Such species would provide additional means by which the identity and composition of the BAG domain, that is, the portion of the protein that is influencing or modulating protein folding, could be identified. In addition, such species would be useful for identifying agents that modulate apoptosis as candidates for therapeutic agents, in particular, anticancer agents. The present invention satisfies these need, as well as providing substantial related advantages.

SUMMARY OF THE INVENTION

The present invention provides a family of BAG-1 related proteins from humans [BAG-1L (SEQ ID NO:2), BAG-1 (beginning at residue 116 of SEQ ID NO:2), BAG-2 (SEQ ID NO: 4), BAG-3 (SEQ ID NO:6) and (SEQ ID NO:20), BAG-4 (SEQ ID NO:8) and (SEQ ID NO:22) and BAG-5 (SEQ ID NO:10) and (SEQ ID NO:24)], the invertebrate C. elegans [BAG-1 (SEQ ID NO:12), BAG-2 (SEQ ID NO:14)] and the fission yeast S. pombe [BAG-1A (SEQ ID NO:16), BAG-1B (SEQ ID NO:18)] and the nucleic acid molecules that encode them.

Another aspect of the present invention provides an amino acid sequence present in the family of BAG-1 related proteins, that modulates Hsc70/Hsp70 chaperone activity, that is, the BAG domain.

Another aspect of the present invention provides novel polypeptide and nucleic acid compositions and methods useful in modulating Hsc70/Hsp70 chaperone activity.

Another aspect of the present invention is directed to methods for detecting agents that modulate the binding of the BAG family of proteins, such as BAG-1 (beginning at residue 116 of SEQ ID NO:2), and related proteins with the Hsc70/Hsp70 Family of proteins or with other proteins that may interact with the BAG-Family proteins.

Still another aspect of the present invention is directed to methods for detecting agents that induce the dissociation of a bound complex formed by the association of BAG-Family proteins with Hsc70/Hsp70 Family molecule chaperones or other proteins.

BRIEF DESCRIPTION OF THE DRAWINGS

FIG. 1 shows the full length cDNA sequence for human BAG-1 (SEQ ID NO:1) protein with the corresponding amino acid sequence (SEQ ID NO:2). Within the full length sequence are included the overlapping sub-sequences of BAG-1 (beginning at nucleotide 391), BAG-1M [beginning at nucleotide 260 of (SEQ ID NO:1)], and BAG-1L [beginning at nucleotide 46 of (SEQ ID NO:1)].

FIGS. 2A and 2B combined shows the full length cDNA sequence (SEQ ID NO:3) aligned with the corresponding amino acid residues for human BAG-2 protein (SEQ ID NO:4).

FIG. 3 shows a cDNA sequence (SEQ ID NO:5) aligned with the corresponding amino acid residues for human BAG-3 protein (SEQ ID NO:6).

FIG. 4 shows the a cDNA sequence (SEQ ID NO:7) aligned with the corresponding amino acid residues for human BAG-4 protein (SEQ ID NO:8).

FIG. 5 shows a cDNA sequence (SEQ ID NO:9) aligned with the corresponding amino acid residues for human BAG-5 protein (SEQ ID NO:10).

FIG. 6A shows the full length cDNA sequence for C. elegans BAG-1 protein (SEQ ID NO:11).

FIG. 6B shows the 210 amino acid sequence for C. elegans BAG-1 protein (SEQ ID NO:12).

FIG. 7A shows the full length cDNA sequence for C. elegans BAG-2 protein (SEQ ID NO:13).

FIG. 7B shows the 458 amino acid sequence for C. elegans BAG-2 protein (SEQ ID NO:14).

FIG. 8A shows the full length cDNA sequence for S. pombe BAG-1A protein (SEQ ID NO:15).

FIG. 8B shows the 195 amino acid sequence for S. pombe BAG-1A protein (SEQ ID NO:16).

FIG. 9A shows the full length cDNA sequence for S. pombe BAG-1B protein (SEQ ID NO:17).

FIG. 9B shows the 206 amino acid sequence for S. pombe BAG-1B protein (SEQ ID NO:18).

FIG. 15A shows an expanded cDNA sequence for human BAG-3 protein (SEQ ID NO:19).

FIG. 15B shows the corresponding amino acid residues for the human BAG-3 protein (SEQ ID NO:20) of FIG. 15A.

FIG. 15C shows the expanded cDNA sequence (SEQ ID NO:19) aligned with the corresponding amino acid residues for human BAG-3 protein of FIG. 15A (SEQ ID NO:20).

FIG. 16A shows an expanded cDNA sequence for human BAG-4 protein (SEQ ID NO:21).

FIG. 16B shows the corresponding amino acid residues for the human BAG-4 protein of FIG. 16A (SEQ ID NO:22).

FIG. 16C shows the expanded cDNA sequence (SEQ ID NO:21) aligned with the corresponding amino acid residues for human BAG-4 protein of FIG. 16A (SEQ ID NO:22).

FIG. 17A shows an expanded cDNA sequence for human BAG-5 protein (SEQ ID NO:23).

FIG. 17B shows the corresponding amino acid residues for the human BAG-5 protein of FIG. 17A (SEQ ID NO:24).

FIG. 17C shows the expanded cDNA sequence (SEQ ID NO:23) aligned with the corresponding amino acid residues for human BAG-5 protein of FIG. 17A (SEQ ID NO:24).

DEFINITIONS

Figure 10A:
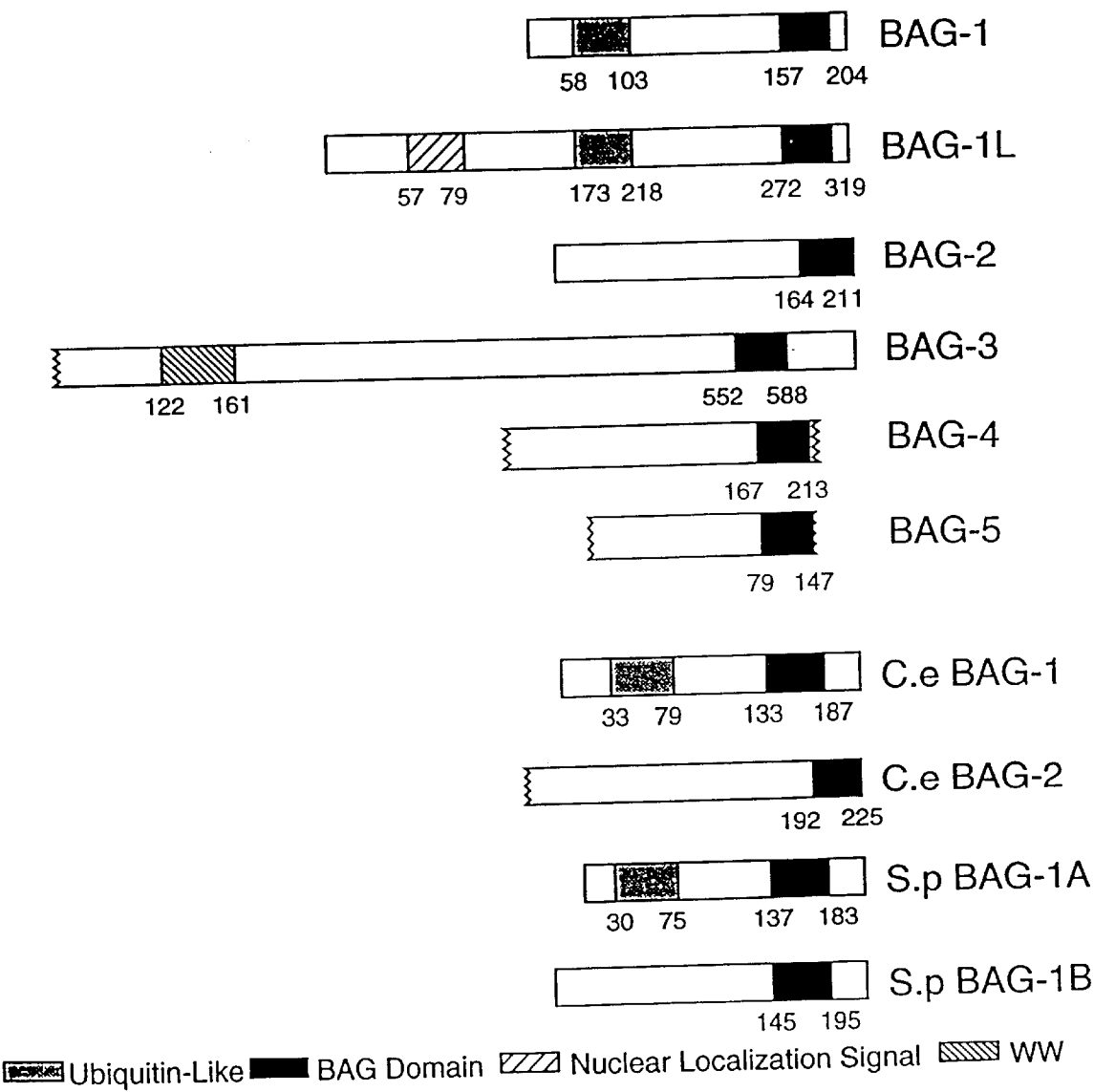
FIG. 10 shows the topologies of the BAG-family proteins; human BAG proteins, BAG-1 (SEQ ID NO:2), BAG-2 (SEQ ID NO:4), BAG-3 (SEQ ID NO:6), BAG-4 (SEQ ID NO:8), BAG-5 (SEQ ID NO:10); S. pombe BAG-1A (SEQ ID NO:16)and BAG-1B (SEQ ID NO:18); and C. elegans BAG-1 (SEQ ID NO:12)and BAG-2 (SEQ ID NO:14). (A) The relative positions of the BAG domains are shown in black, ubiquitin-like regions are represented in gray, WW domain are represented in strips. Nucleoplasmin-like nuclear localization sequence are also shown. (B) The amino acid sequences of the BAG domain for human BAG-1 (SEQ ID NO:2), BAG-2 (SEQ ID NO:4), BAG-3 (SEQ ID NO:6), BAG-4 (SEQ ID NO:8), BAG-5 (SEQ ID NO:10), S. pombe BAG-1A (SEQ ID NO:16)and BAG-1B (SEQ ID NO:18), and C. elegans BAG-1 (SEQ ID NO:12)and BAG-2 (SEQ ID NO:14) are aligned demonstrating their homology. Black and gray shading represent identical and similar amino acids, respectively.

The term "apoptosis", as used herein, refers to the process of programmed cell death, although not all programmed cell deaths occur through apoptosis, as used herein, "apoptosis" and "programmed cell death" are used interchangeably.

The term "tumor cell proliferation", as used herein refers to the ability of tumor cells to grow and thus expand a tumor mass.

The term "cell migration", as used herein refers to the role cell motility plays in the invasion and potentially metastasis by tumor cells.

The term "metastasis", as used herein, refers to the spread of a disease process from one part of the body to another, as in the appearance of neoplasms in parts of the body remote from the site of the primary tumor; results in dissemination of tumor cells by the lymphatics or blood vessels or by direct extension through serious cavitites or subarachnoid or other spaces.

The term "steroid hormone receptor function", as used herein refers to physiological, cellular and molecular functioning of receptors sites that bind with steroid hormones.

The term "substantially purified", as used herein, refers to nucleic acid or amino acid sequence that are removed from their natural environment, isolated or separated, and are at least 60% free, preferably 75% free, and most preferably 90% free from other components with which they are naturally associated.

"Nucleic acid molecule" as used herein refers to an oligonucleotide, nucleotide, or polynucleotide, and fragments or portions thereof, and to DNA or RNA of genomic or synthetic origin which may be single or double stranded, and represent the sense or antisense strand.

"Hybridization", as used herein, refers to any process by which a strand of nucleic acid binds with a complementary strand through base pairing.

The terms "complementary" or "complementarity", as used herein, refer to the natural binding of polynucleotides under permissive salt and temperature conditions by base-pairing. For example, the sequence "A-G-T binds to the complementary sequence "T-C-A".

The term "homology", as used herein, refers to a degree of complementarity. There may be partial homology or complete homology (i.e., identity). A partially complementary sequence is one that at least partially inhibits an identical sequence from hybridizing to a target nucleic acid and is referred to using the functional term "substantially homologous." The inhibition of hybridization of the completely complementary sequence to the target sequence may be examined using a hybridzation assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense, and "positive" is sometimes used in reference to the sense strand.

"Amino acid sequence" as used herein refers to an oligopeptide, peptide, polypeptide, or protein sequence, and fragments or portions thereof, and to naturally occurring or synthetic molecules. Where "amino acid sequence" is recited herein this term excludes an amino acid sequence of a naturally occurring protein. "Amino acid sequence", "polypeptide" or "protein" are not meant to limit the amino acid sequence to the complete, native amino acid sequence associated with the recited protein molecule.

The term "functional fragments" or "fragments", as used herein, with regard to a protein refers to portions of that protein that are capable of exhibiting or carrying out the activity exhibited by the protein as a whole. The portions may range in size from three amino acid residues to the entire amino acid sequence minus one amino acid. For example, a protein "comprising at least a functional fragment of the amino acid sequence of SEQ ID NO:1", encompasses the full-length of the protein of SEQ ID NO:1 and portions thereof.

A "derivative" of a BAG protein, as used herein, refers to an amino acid sequence that is altered by one or more amino acids. The derivative may have "conservative" changes, wherein a substituted amino acid has similar structural or chemical properties, e.g., substitution of an apolar amino acid with another apolar amino acid (such as replacement of leucine with isoleucine). The derivative may also have "nonconservative" changes, wherein a substituted amino acid has different but sufficiently similar structural or chemical properties that permits such a substitution without adversely effecting the desired biological activity, e.g., replacement of an amino acid with an uncharged polar R group with an amino acid with an apolar R group (such as replacement of glycine with tryptophan), or alternatively replacement of an amino acid with a charged R group with an amino acid with an uncharged Polar R group (such as replacement of lysine with asparagine).

Amino Acids - Apolar R Groups

| Amino Acid | Radical | 3-Letter | 1-Letter |
|---|---|---|---|
| | | Abbreviations | |
| alanine | methyl | ala | A |
| valine | 2-propyl | aal | V |
| leucine | 2-methylpropyl | leu | L |
| isoleucine | 2-butyl | ile | I |
| proline | propyl* - cyclized | pro | P |
| phenylalanine | benzyl | phe | F |
| trytophan | 3-indolylmethl | tyr | W |
| methionine | methylthioethyl | met | M |

Amino Acids - Uncharged Polar R Groups

| Amino Acid | Radical | 3-Letter | 1-Letter |
|---|---|---|---|
| | | Abbreviations | |
| glycine | H | gly | G |
| serine | hydroxymethyl | ser | S |
| threonine | 1-hydroxyethyl | thr | T |
| cysteine | thiolmethyl | cys | C |
| tyrosine | 4-hydroxyphenylmethyl | tyr | Y |
| asparagine | aminocarbonylmethyl | asn | N |
| glutamine | aminocarbonylethyl | gln | Q |

Amino Acids - Charged R Groups

| Amino Acid | Radical | 3-Letter | 1-Letter |
|---|---|---|---|
| | | Abbreviations | |
| aspartic acid | carboxymethyl | asp | D |
| glutamic acid | carboxyethyl | glu | E |
| lysine | 4-aminobutyl | lys | K |
| arginine | 3-guanylpropyl | arg | R |
| histidine | 4-imidazoylmethyl | his | H |

Similar minor modifications may also include amino acids deletions or insertions or both. Guidance in determining which amino acid residues may be modified as indicated above without abolishing the desired biological functionality may be determined using computer programs well known in the art, for example, DNASTAR software. In addition, the derivative may also result from chemical modifications to the encoded polypeptide, including but not limited to the following, replacement of hydrogen by an alkyl, acyl, or amino group; esterification of a carboxyl group with a suitable alkyl or aryl moiety; alkylation of a hydroxyl group to form an ether derivative. Further a derivative may also result from the substitution of a L-configuration amino acid with its corresponding D-configuration counterpart.

The term "mimetic", as used herein, refers to a molecule, the structure of which is developed from knowledge of the structure of a protein/polypeptide or portions thereof (such as BAG-1) and, as such, is able to effect some or all of the actions of BAG-1 protein.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al., *Anticancer Drug Des.* 8:53–63 (1993)).

DETAILED DESCRIPTION OF THE INVENTION

The present invention provides a family of BAG-1 related proteins from humans [BAG-1L (SEQ ID NO:2), BAG-1S beginning at residue 116 of SEQ ID NO:2, BAG-2 (SEQ ID NO:4), BAG-3 (SEQ ID NO:6) and (SEQ ID NO:20), BAG-4 (SEQ ID NO: 8) and (SEQ ID NO:22) and BAG-5 (SEQ ID NO:10) and (SEQ ID NO:24)], the invertebrate *C. elegans* [BAG-1 (SEQ ID NO:12), BAG-2 (SEQ ID NO:14)] and the fission yeast *S. pombe* [BAG-1A (SEQ ID NO:16), BAG-1B (SEQ ID NO:18)], specifically the full length amino acid sequences comprising human BAG-1L (SEQ ID NO:2), BAG-1 (beginning at residue 116 of SEQ ID NO:2), and BAG-2 (SEQ ID NO:4) *C. elegans* BAG-1 (SEQ ID NO:12), and BAG-2 (SEQ ID NO:14), and *S. pombe* BAG-1A (SEQ ID NO:16) and BAG-LB (SEQ ID NO:18); and partial sequences comprising human BAG-3 (SEQ ID NO: 6) and (SEQ ID NO:20), BAG-4 (SEQ ID NO:8) and (SEQ ID NO:22), and BAG-5 (SEQ ID NO:10) and (SEQ ID NO:24) and functional fragments thereof. In particular, the invention provides the amino acid sequences comprising human BAG-2 (SEQ ID NO:4), BAG-3 (SEQ ID NO:6) and (SEQ ID NO:20), BAG-4 (SEQ ID NO:8) and (SEQ ID NO:22), and BAG-5 (SEQ ID NO:10) and (SEQ ID NO:24) proteins.

Another aspect of the present invention provides the nucleic molecule and nucleotide sequences that encode the family of BAG-1 related proteins from humans [BAG-1 (SEQ ID NO:1), BAG-2 (SEQ ID NO:3), BAG-3 (SEQ ID NO:5) and (SEQ ID NO:19), BAG-4 (SEQ ID NO:7) and (SEQ ID NO:21) and BAG-5 (SEQ ID NO:9) and (SEQ ID NO:23)], the invertebrate *C. elegans* [BAG-1 (SEQ ID NO:11), BAG-2(SEQ ID NO:13)] and the fission yeast *S. pombe* [BAG-1A (SEQ ID NO:15), BAG-LB (SEQ ID NO:17)].

BAG-1L (SEQ ID NO:2) is a multifunctional protein that blocks apoptosis, promotes tumor cell metastasis, and contributes to factor-independent and p53-resistant cell growth. BAG-1L (SEQ ID NO:2) interacts with several types of proteins, including Bcl-2, some tyrosine kinase growth factor receptors, steroid hormone receptors, and the p53-induced cell cycle regulator Siah-1A.

BAG-1 is a regulator of Hsc70/Hsp70 family molecular chaperones. A carboxyl-terminal domain in this protein binds tightly to the ATPase domains of Hsc70 and Hsp70 ($K_D$=1 nM) (Zeiner, M., Gebauer, M., and Gehring, U., *EMBO J.* 16: 5483–5490, (1997)). BAG-1 modulates the activity of these molecular chaperones, acting as an apparent functional antagonist of the Hsp70/Hsc70-associated protein Hip (3–5)(Höhfeld, J. and Jentsch, S., *EMBO J.* 16: 6209–6216, (1997); Takayama, S., Bimston, D. N., Matsuzawa, S., Freeman, B. C., Aime-Sempe, C., Xie, Z., Morimoto, R. J., and Reed, J. C., *EMBO J.* 16: 4887–96, (1997); Zeiner, M., Gebauer, M., and Gehring, U., *EMBO J.* 16: 5483–5490, (1997)). In general, protein refolding is accomplished by Hsp70/Hsc70 through repeated cycles of target peptide binding and release, coupled to ATP hydrolysis (Ellis, R., *Curr Biol.* 7: R531-R533, (1997)). BAG-1 appears to promote substrate release, whereas Hip stabilizes Hsp70/Hsc70 complex formation with target peptides (H öhfeld, J., Minami, Y., and Hartl, F.-U., *Cell.* 83: 589–598, (1995)). Since each substrate interaction with Hsc70/Hsp70 is unique in terms of the optimal length of time the protein target should remain complexed with Hsc70/Hsp70 for achieving new conformations, the net effect of BAG-1 can be either enhancement or inhibition of the refolding reaction.

The 70 kd heat shock family proteins (Hsp70/Hsc70) are essential to a variety of cellular processes and have been implicated in cancer, yet it is unclear how these proteins are regulated in vivo. A variety of co-chaperones have been identified which may target Hsp70/Hsc70 to different subcellular compartments or promote their interactions with specific protein or protein complexes. BAG-1 appears to represent a novel Hsp70/Hsc70 regulator which differs functionally from all other mammalian co-chaperones identified to date, such as members of the DnaJ-, Hip-, Hop-, and cyclophilin-families of proteins.

Another aspect of the present invention provides the amino acid sequence of a binding domain of about 40 to 55 amino acids that bind the a Hsc70/Hsp70 ATPase domain. The BAG domain is situated near the C-terminus, and the ubiquitin-like domains are situated near the N-terminus.

The BAG family of proteins of the present invention contain a common conserved C-terminal domain (the "BAG" domain) that facilitates binding to the ATPase domain of Hsp70/Hsc70. The carboxyl-terminal domain of BAG-1 binds to the ATPase domain of Hsc70/Hsp70 and regulates its chaperone function by acting as a ADP-ATP exchange factor. Other domains of BAG-1 mediate interactions with proteins such as Bcl-2 and retinoic acid receptors (RARs), allowing BAG-1 to target Hsc70/Hsp70 to other proteins, presumably modulating their function by changing their conformations.

Human BAG-1 was previously shown to inhibit Hsc70/Hsp70 dependent refolding of denatured protein substrates in vitro (S. Takayama, et al., *EMBO J* 16, 4887-96 (1997); M. Zeiner, M. Gebauer, U. Gehring, *EMBO J.* 16, 5483–5490 (1997); and J. Höhfeld, S. Jentsch, *EMBO J.* 16, 6209–6216 (1997)). In Example III, Part A the effects of recombinant human BAG-1, BAG-2 (SEQ ID NO:4) and BAG-3 (SEQ ID NO:6) were compared using in vitro protein refolding assays similar to those employed previously for assessing BAG-1. The study showed that addition of equimolar amounts of each of the recombinant proteins to Hsc70 resulted in significant inhibition of luciferase refolding, with BAG-2 (SEQ ID NO:4) and BAG-3 (SEQ ID NO:6) showing somewhat greater inhibitor activity than BAG-1 (FIG. 4A). In a separate luciferase folding study BAG-1, BAG-2 (SEQ ID NO:4) and BAG-3 (SEQ ID NO:6) once again displayed inhibition of luciferase refolding, however in this study varying amounts of BAG-1, BAG-2 (SEQ ID NO:4) and BAG-3 (SEQ ID NO:6) were added relative to Hsc70 which resulting in concentration-dependent inhibition of Hsc70 chaperone activity, i.e., luciferase folding (Example III Part A). Additional follow on studies using the same experimental protocols as the previous studies, as taught in Example IIA, have shown that BAG-4 (SEQ ID NO:22) also undergoes association with Hsc70/ATPase.

Yet another aspect of the present invention provides a nucleotide sequence having at least about 15 nucleotides and, generally, about 25 nucleotides, preferably about 35 nucleotides, more preferably about 45 nucleotides, and most preferably about 55 nucleotides that can hybridize or is complementary under relatively stringent conditions to a portion of the nucleic acid sequences shown in FIGS. 1–9 and FIGS. 15–17, in particular the BAG domain as shown in in FIG. 1B, e.g., nucleotides 552–593 of human BAG-3, or nucleotides 167–221 of human BAG-4.

Yet another aspect of the present invention provides a compound of the formula,

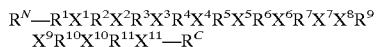

wherein, $R^N$ is a group of 1 to 552 independently selected amino acids;

$R^1$ is a group of 3 independently selected amino acids;

$X^1$ is an amino acid with a charged or uncharged R group, such as aspartic acid, glutamic acid, asparagine, or glutamine;

$R^2$ is a group of 7 independently selected amino acids;

$X^2$ is an amino acid with a charged R group, such as glutamic acid;

$R^3$ is a group of 5 independently selected amino acids;

$X^3$ is an amino acid with an apolar R group, such as leucine, methionine, or isoleucine;

$R^4$ is a group of 3 independently selected amino acids;

$X^4$ is an amino acid with charged R group, such as aspartic acid or glutamine acid;

$R^5$ is a single independently selected amino acid;

$X^5$ is an amino acid with apolar or uncharged R group, such as leucine, valine, methionine, alanine or threonine;

$R^6$ is a group of 15 independently selected amino acids;

$X^6$ is an amino acid with a charged or uncharged R group, such as arginine, lysine, glutamine or aspartic acid;

$R^7$ is a group of 2 independently selected amino acids;

$X^7$ is an amino acid with a charged R group, such as arginine;

$X^8$ is an amino acid with a charged R group, such as arginine or lysine;

$R^9$ is a group of 2 independently selected amino acids;

$X^9$ is an amino acid with an apolar R group, such as valine;

$R^{10}$ is a group of 3 independently selected amino acids;

$X^{10}$ is an amino acid with an uncharged R group, such as glutamine;

$R^{11}$ is a group of 2 independently selected amino acids;

$X^{11}$ is an amino acid with an apolar R group, such as leucine; and $R^C$ is a group of 1 to 100 independently selected amino acids.

A nucleotide sequence of at least about 15 nucleotides and, generally, about 25 nucleotides, preferably about 35 nucleotides, more preferably about 45 nucleotides, and most preferably about 55 nucleotides can be useful, for example, as a primer for the polymerase chain reaction (PCR) or other similar reaction mediated by a polymerase such as a DNA or RNA polymerase (see PCR Protocols: A guide to methods and applications, ed. Innis et al. (Academic Press, Inc., 1990), which is incorporated herein by reference; see, for example, pages 40–41). In addition, such a nucleotide sequence of the invention can be useful as a probe in a hybridization reaction such as Southern or northern blot analysis or in a binding assay such as a gel shift assay.

A nucleotide sequence of the invention can be particularly useful as an antisense molecule, which can be DNA or RNA and can be targeted to all or a portion of the 5'-untranslated region or of the 5'-translated region of a bag-1 nucleic acid sequence in a cell. For example, an antisense molecule can be directed to at least a portion of the sequence shown as the BAG domain in FIG. 1A, e.g., nucleotides 272–319 of human BAG-1L (SEQ ID NO:1), or nucleotides 79–147 of human BAG-5 (SEQ ID NO:9). Since the 5'-region of a nucleic acid contains elements involved in the control of expression of an encoded protein, an antisense molecule directed to the 5'-region of a nucleic acid molecule can affect the levels of protein expressed in a cell.

A nucleotide sequence of the invention also can be useful as a probe to identify a genetic defect due a mutation of a gene encoding a BAG protein in a cell. Such a genetic defect can lead to aberrant expression of a BAG protein in the cell or to expression of an aberrant BAG protein, which does not properly associate with a Bcl-2-related protein or Hsc70/Hsp70 protein in the cell. As a result, a genetic defect in a gene encoding, for example, human BAG-1 can result in a pathology characterized by increased or decreased levels in protein folding.

Further a nucleotide compound or composition as taught in the present invention can be synthesized using routine methods or can be purchased from a commercial source. In addition, a population of such nucleotide sequences can be prepared by restriction endonuclease or mild DNAse digestion of a nucleic acid molecule that contains nucleotides as shown in the nucleotide sequences shown in FIGS. 1–9 and FIGS. 15–17 that encodes the amino acids sequences also shown in FIGS. 1–9 and FIGS. 15–17. Methods for preparing and using such nucleotide sequences, for example, as hybridization probes to screen a library for homologous nucleic acid molecules are well known in the art (see, for example, Sambrook et al., *Molecular Cloning: A laboratory manual* (Cold Spring Harbor Laboratory Press 1989); Ausubel et al., *Current Protocols in Molecular Biology* (Green Publ., NY 1989), each of which is incorporated herein by reference).

A particular nucleotide sequence can be designed based, for example, on a comparison of the nucleic acid molecules encoding any one of the BAG family proteins, as shown in FIGS. 1–9 and FIGS. 15–17, with another in the family. Such a comparison allows, for example, the preparation of a nucleotide sequence that will hybridize to a conserved region present in both nucleic acid molecules, thus providing a means to identify homologous nucleic acid molecules present in other cell types or other organisms. In addition, such a comparison allows the preparation of a nucleotide sequence that will hybridize to a unique region of any of the BAG family nucleotide sequences, such as those corresponding to the BAG domain, thus allowing identification of other proteins sharing this motif. In this regard, it is recognized that, while the human BAG-3 proteins shown as FIGS. 3 and 20, and human BAG-5 proteins shown as FIGS. 5 and 24, are only partial sequences, a variant human BAG-3 or BAG-5 produced, for example, by alternative splicing can exist and can be identified using an appropriately designed nucleotide sequence of the invention as a probe. Such useful probes readily can be identified by inspection of the sequences shown in the disclosed Figures by a comparison of the encoding nucleotide sequences.

If desired, a nucleotide sequence of the invention can incorporate a detectable moiety such as a radiolabel, a fluorochrome, a ferromagnetic substance, a luminescent tag or a detectable binding agent such as biotin. These and other detectable moieties and methods of incorporating such moieties into a nucleotide sequence are well known in the art and are commercially available. A population of labelled nucleotide sequences can be prepared, for example, by nick translation of a nucleic acid molecule of the invention (Sambrook et al., supra, 1989; Ausubel et al., supra, 1989).

One skilled in the art would know that a method involving hybridization of a nucleotide sequence of the invention can require that hybridization be performed under relatively stringent conditions such that nonspecific background hybridization is minimized. Such hybridization conditions can be determined empirically or can be estimated based, for example, on the relative GC content of a sequence and the number of mismatches, if known, between the probe and the target sequence (see, for example, Sambrook et al., supra, 1989).

The invention further provides antibodies specific for human BAG family protein. As used herein, the term "antibody" includes polyclonal and monoclonal antibodies, as well as polypeptide fragments of antibodies that retain a specific binding activity for human BAG-1 of at least about $1 \times 10^5$ $M^{-1}$. One skilled in the art would know that anti-BAG-1 antibody fragments such as Fab, $F(ab')_2$ and Fv fragments can retain specific binding activity for human BAG-1 (beginning at residue 116 of SEQ ID NO:2) and, thus, are included within the definition of an antibody. In addition, the term "antibody" as used herein includes naturally occurring antibodies as well as non-naturally occurring antibodies and fragments that retain binding activity such as chimeric antibodies or humanized antibodies. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

One skilled in the art would know that purified BAG family protein, which can be prepared from natural sources or synthesized chemically or produced recombinantly, or portions of a BAG family protein, including a portion of human BAG family protein such as a synthetic peptide as described above, can be used as an immunogen. Such peptides useful for raising an antibody include, for example, peptide portions of the N-terminal 85 amino acids or the BAG domain of any of the human BAG proteins (see FIG. 1B). A particularly advantageous use of such a protein is for the immunostaining, wherein the methods provides a process to contrast the immunostaining of BAG-family proteins in carcinoma cells with adjacent non-neoplastic prostatic epithelial and basal cells which are generally present in the same tissue sections. These results would be correlated with a Gleason grade to determine whether any of the BAG-family proteins tend to be expressed at higher or lower levels in histologically advanced tumors. From this process a determination can be made as to degree at which the disease is progressing in a given patient, i.e., a prognosis can be made.

Non-immunogenic fragments or synthetic peptides of BAG proteins can be made immunogenic by coupling the hapten to a carrier molecule such bovine serum albumin (BSA) or keyhole limpet hemocyanin (KLH), as described in Example IV, below. In addition, various other carrier molecules and methods for coupling a hapten to a carrier molecule are well known in the art and described, for example, by Harlow and Lane, *Antibodies: A laboratory manual* (Cold Spring Harbor Laboratory Press, 1988), which is incorporated herein by reference.

EXAMPLES

The following examples are given to enable those skilled in the art to more clearly understand and to practice the present invention. They should not be considered as limiting the scope of the invention, but merely as being illustrative and representative thereof.

Example I

Isolation and Characterization of BAG-family cDNA Sequences

This example describes methods for isolating and characterizing of BAG-family cDNA sequences from human, nematode and yeast.

A. Cloning of Human BAG cDNA Sequences

Yeast two-hybrid library screening of a human Jurkat cell cDNA library was performed as described by Takayama et al., *EMBO J.*, 16:4887–96 (1997); Matsuzawa et al., *EMBO J.*, 17:2736–2747 (1998), which are incorporated herein by reference) using EGY48 strain yeast transformed with pGilda-Hsc70/ATPase (67–377 amino acids) and the lacZ reporter plasmid pSH18–34. Of the resulting ~5×10⁶ transformants, 112 Leu⁺ colonies were obtained after 1 week incubation at 30° C. Assay of β-galactosidase (β-gal) activity of these colonies resulted in 96 clones. Mating tests were then performed using RFY206 yeast strain transformed with pGilda, pGilda mBAG-1 (1–219), or pGilda Hsc70/ATPase. Of these, 66 displayed specific interactions with Hsc70/ATPase. The pJG4–5 cDNAs were recovered using KC8 *E. coli* strain which is auxotrophic for tryptophan (Trp). DNA sequencing revealed 3 partially overlapping human BAG-1, 4 identical and one overlapping cDNAs encoding BAG-2, and 2 partially overlapping BAG-3 clones.

Using the above described yeast two-hybrid screen with the ATPase domain of Hsc70 as "bait", several human cDNAs were cloned which encode portions of BAG-1 or of two other BAG-1-like proteins which are termed BAG-2 (SEQ ID NO:4) and BAG-3 (SEQ ID NO:6). The longest of the cDNAs for BAG-2 (SEQ ID NO:3) and BAG-3 (SEQ ID NO:5) contained open reading frames (ORFs) of 207 and 162 amino acids, respectively, followed by stop codons. All BAG-1 (SEQ ID NO:1), BAG-2 (SEQ ID NO:3) and BAG-3 (SEQ ID NO:5) cDNAs obtained by two-hybrid library screening with Hsc70/ATPase contained a conserved domain of about 40–50 amino acids which are termed the "BAG" domain and are shown in FIG. 10. These results demonstrate that a family of BAG-1-related proteins all contain a conserved ~45 amino acid region near their C-terminus that binds Hsc70/Hsp70.

B. Identification of Additional BAG-family Proteins

A search of the translated Genbank database using the bBLAST and FASTA search programs also identified human ESTs that provided sequences for further investigation of BAG-family proteins. The putative BAG-4 (SEQ ID NO:8) and BAG-5 (SEQ ID NO:10) proteins contain BAG-domains that share the greatest sequence similarity with the BAG-domain of BAG-3 (SEQ ID NO:6). These were designated BAG-4 (Accession number AA693697, N74588) and BAG-5 (Accession number AA456862, N34101). BAG-4 has 62% identity and ~81% similarity to BAG-3, and BAG-5 has 51% identity and ~75% similarity to BAG-3.

Additional BAG-family orthologues or homologues were also identified using computer-based searches and resulted in BAG-family homologue in the nematode C. elegans and the fission yeast S. pombe. The C. elegans genome encodes two apparent BAG-family proteins, which are most similar in their overall sequences to the human BAG-1 (Afo39713, gi:2773211) (SEQ ID NO:12) and BAG-2 (SEQ ID NO:14) (Afo68719, gi:318927). The S. pombe contains two BAG-family proteins that share the greatest overall sequence similarity with human BAG-1 (Alo23S54,gi/3133105 and Alo23634, gi/3150250). The human and C. elegans BAG-1 proteins as well as S. pombe BAG-1A all have ubiquitin-like domains near their N-termini (see FIG. 10A) of unknown function.

The overall predicted amino acid sequences of the C. elegans BAG-1 (SEQ ID NO:12) and S. pombe BAG-1A (SEQ ID NO:16) proteins are ~18% identical (~61% similar) and ~17% identical (~64% similar), respectively, to human BAG-1, implying origin from a common ancestral gene. The C. elegans BAG-1 protein (SEQ ID NO:12), however, contains a 5 to 7 amino acid insert in its BAG-domain as compared to the human, murine, and yeast BAG-1 homologues (see FIG. 10B), and is more similar to BAG-2 (SEQ ID NO:4) in regard to its BAG-domain. C. elegans and human BAG-2 also may be derived from a common ancestor as the C-terminal 225 amino acid region which encompasses both the BAG domain and upstream region of both C. elegans and human BAG-2 share ~34% amino acid sequence identity and ~70% similarity. The human BAG-2 protein (SEQ ID NO:4), however, contains a 9 amino acid insert in its BAG-domain compared to it C. elegans counterpart (see FIG. 10B). Evolutionary-tree prediction algorithms suggest that human and C. elegans BAG-2 represent a distinct branch of the BAG-family that is more evolutionarily distant from the other BAG-family proteins. None of the predicted BAG-family proteins contain recognizable regions analogous to those found in other Hsc70 regulatory proteins, such as the J-domains and G/F-domains of DnaJ family proteins and the Tetratricopeptide Repeat (TR) domains of Hip/Hop family proteins.

C. Yeast Two-hybrid Assay of BAG Binding to Hsc70/ATPase

Figure 11:
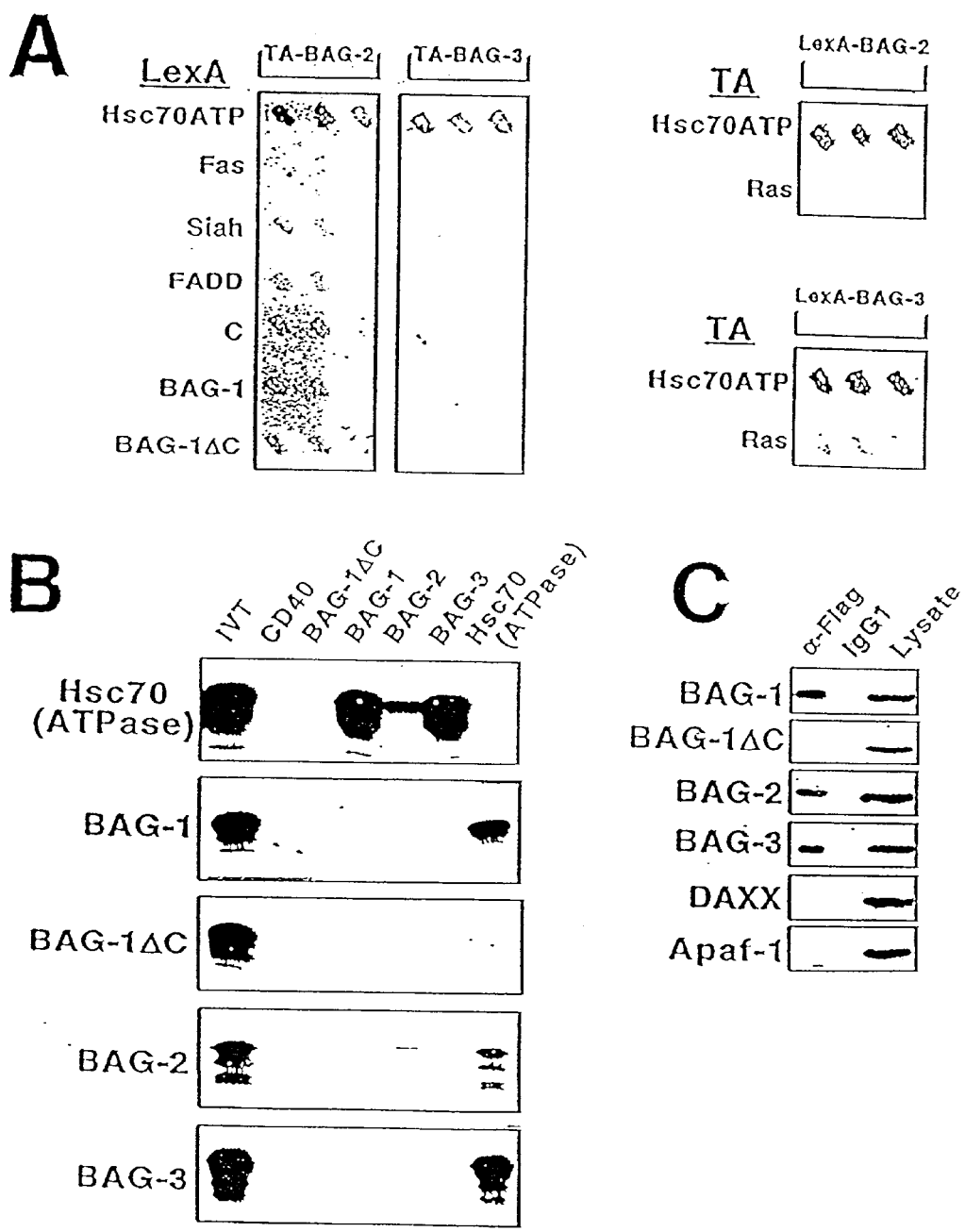
FIG. 11 shows assays demonstrating the interaction of BAG-family proteins with Hsc70/ATPase. (A) Two-hybrid assays using yeast expressing the indicated fusion proteins. Blue color indicates a positive interaction, resulting in activation of the lacZ reporter gene. (B) In vitro protein assays using GST-fusion proteins and $^{35}$S-labeled in vitro translated proteins. (C) Co-immunoprecipitation assays using anti-Flag or IgG1 control antibodies and lysates from 293T cells expressing Flag-tagged BAG-1 (beginning at residue 116 of SEQ ID NO:2), BAG-2 (SEQ ID NO:4), BAG-3 (SEQ ID NO:6), Daxx, or Apaf-1.

The longest of the cDNAs obtained for the BAG-2 and BAG-3 proteins were expressed with N-terminal transactivation (TA) domains in yeast and tested by yeast two-hybrid assay for interactions with fusion proteins consisting of Hsp70/ATPase or a variety of unrelated proteins (Fas, Siah, Fadd) containing N-terminal LexA DNA-binding domains. TA-BAG-2 and TA-BAG-3 demonstrated positive interactions with LexA-Hsc70/ATPase, resulting in transactivation of a lacZ reporter gene that was under the control of LexA operators (FIG. 11A). No interactions with LexA-Fas (cytosolic domain), LexA-Siah, LexA-Fadd, or LexA were detected (see FIG. 11A) demonstrating that the BAG-2 and BAG-3 proteins interact specifically with Hsc70/ATPase. Specific two-hybrid interactions between Hsc70/ATPase and either BAG-2 or BAG-3 were also observed when BAG-2 and BAG-3 were expressed as LexA DNA-binding domain fusion proteins and Hsc70/ATPase was fused with a TA domain (see FIG. 11A; right panel). These results demonstrate that similarly to BAG-1, BAG-2 and BAG-3 specifically interact with Hsc70/ATPase.

In order to determine whether the BAG proteins are capable of forming heterodimers, coexpression of BAG-2 and BAG-3 in the yeast two-hybrid assay was also performed. Coexpression of BAG-2 and BAG-3 failed to show interaction with BAG-1 or a deletion mutant of BAG-1 (ΔC) which is missing part of its C-terminal domain required for Hsp70/Hsc70 binding suggest that these proteins do not form heterdimers.

D. Isolation and Characterization of the Complete Open Reading Frame Sequences of BAG-2 and BAG-3

In order to deduce the complete ORFs of BAG-2 and BAG-3, a λ-phage cDNA library was screened as follows, using hybridization probes derived from the two-hybrid screening. A human jurkat T-cell λ-ZapII library cDNA library (Stratagene) was screened by hybridization using $^{32}$P-labeled purified insert DNA from the longest of the human BAG-2 (clone #11) and human BAG-3 (clone #28) cDNA clones. From about one million clones screened, 38 BAG-2 and 23 BAG-3 clones were identified, cloned, and their cDNA inserts recovered as pSKII plasmids using a helper phage method (Stratagene). DNA sequencing of λ-phage derived human BAG-2 cDNA clones revealed an ORF encoding a predicted 211 amino acid protein, preceded by an in-frame stop codon. The longest human BAG-3 λ-phage cDNA clone contains a continuous ORF of 682 amino acids followed by a stop codon, but without an identifiable start codon (see FIG. 10A).

Although BAG-1L (SEQ ID NO:2), BAG-1 (beginning at residue 116 of SEQ ID NO:2), BAG-2 (SEQ ID NO:4), and BAG-3 (SEQ ID NO:6) all contain a homologous BAG domain near their C-terminus, the N-terminal regions of these proteins are dissimilar. Using a combination of search tools (Prosite Search: PP search, using the Prosite pattern database, BCM Search Launcher, Baylor College of Medicine, and Blocks Search), it was determined that the BAG-2 N-terminal region contains potential kinase phosphorylation sites but otherwise shares no apparent similarity with other proteins or known functional domains.

Figure 10B:
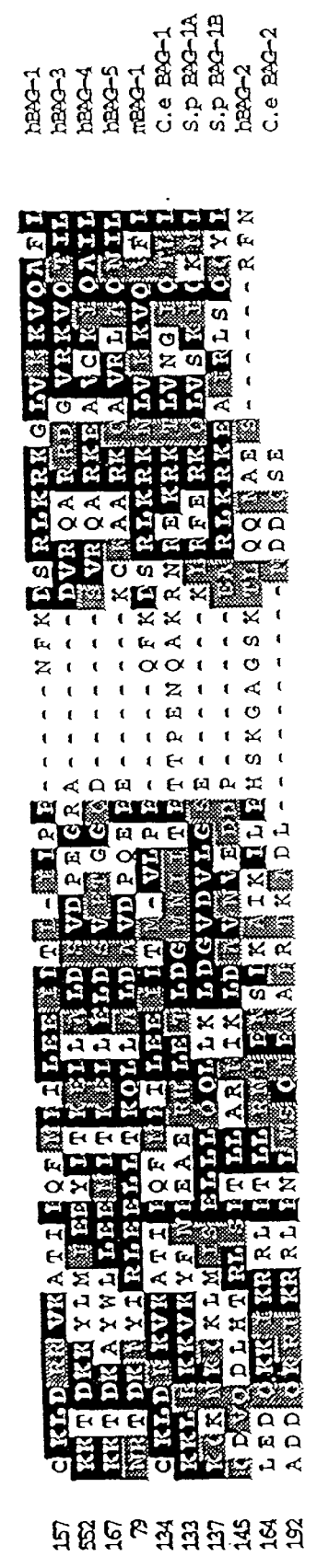

In contrast, the predicted N-terminal region BAG-3 contains a WW domain as shown in FIG. 10A. WW domains have been identified in a wide variety of signaling proteins, including a Yes kinase adaptor protein (YAP), the $Na^+$-channel regulator Nedd4, formin-binding proteins, dystrophin, and the peptidyl prolyl cis-trans-isomerase Pin-1. These roughly 40 amino acid domains mediate protein interactions and bind the preferred peptide ligand sequence xPPxY (Sudol., *TIBS*, 21: 161–163, 1996, which is incorporated herein by reference).

Example II

In vitro Association of BAG Proteins and Hsc70/ATPase

This example demonstrates that BAG-2 (SEQ ID NO:4) and BAG-3 (SEQ ID NO:6) bind Hsc70/ATPase in various in vitro assays.

A. Solution Binding Assay of BAG-2 and BAG-3 to Hsc70/ATPase

Association of BAG-2 (SEQ ID NO:4) and BAG-3 (SEQ ID NO:6) with Hsc70/ATPase was determine by an in vitro protein binding assay where Hsc70/ATPase or BAG-family proteins were expressed in bacteria as Glutathione S-Transferase (GST) fusion proteins. Purified cDNA sequences encoding residues 5 to 211 of human BAG-2 (clone #11) and the C-terminal 135 amino acids of human BAG-3 (clone #28) (see FIG. 10A) were subcloned into the EcoRI/Xho I sites of pGEX4T-1 prokaryotic expression plasmid (Pharmacia; Piscataway, N.J.). These plasmids as well as pGEX4T-1-BAG-1, pGEX-4T-1-BAG-1 (ΔC), and pGEX-4T-1-XL which have been described previously (Takayama et al., supra (1997); Xie et al., *Biochemistry*, 37:6410–6418, (1998), which are incorporated herein by reference), were expressed in XL-1 blue strain *E. Coli* (Stratagene, Inc., La Jolla, Calif.). Briefly, a single colony was inoculated into 1L of LB media containing 50 μg/ml ampicillin and grown at 37° C. overnight. The culture was then diluted by half with fresh LB/ampicillin and cooled to room temperature for 1 hr, before inducing with 0.4 mM IPTG for 6 h at 25° C.

Cells were recovered and incubated with 0.5 mg/ml lysozyme in 50 mM Tris (pH 8.0), 150 mM NaCl, 1 Tween-20, 0.1% 2-mercaptoethanol, 5 mM EDTA, 1 mM PMSF and a mixture of other protease inhibitors obtained from Boehringer Mannheim (1697498) at room temperature for 0.5 h, followed by sonication. Cellular debris were pelleted by centrifugation at 27,500 g for 10 min and the resulting supernatants were incubated with 30 ml of glutathionine-Sepharose (Pharmacia) at 4° C. overnight. The resin was then washed with 20 mM Tris (pH 8.0), 150 mM NaCl, 0.1% Tween-20, and 0.1% 2-mercaptoethanol until the OD 280 nm reached <0.01. For removal of GST, the resin with immobilized GST-fusion protein was incubated with 10U of thrombin (Boehringer, Inc.) at 4° C. in 20 mM Tris (pH 8.0), 150 mM NaCl, 0.1% Tween-20, 0.1% 2-Mercaptoethanol, and 2.5 mM CaCl2 overnight. Released proteins were then purified on Mono Q (HR10/10, Pharmacia) by FPLC using a linear gradient of 0.5M NaCl at pH 8.0 and dialyzed into chaperone assay buffer.

The ability of BAG-2 (SEQ ID NO:4) or BAG-3 (SEQ ID NO:6) to bind Hsc70/ATPase in solution was then examined. GST control or GST-BAG proteins were immobilized on glutathione-Sepharose and tested for binding to 35S-labeled in vitro translated (IVT) proteins. Immunoprecipitation and in vitro GST-protein binding assays were performed as described by Takayama et al., supra (1997), using pCI-Neo flag or pcDNA3-HA into which human Bag-2 (clone #11) or human BAG-3 (clone #28) had been subcloned for in vitro translation of 35S-L-methionine labeled proteins or expression in 293T cells. As shown in FIG. 11B, $^{35}$S-Hsc70/ATPase bound in vitro to GST-BAG-1, GST-BAG-2, and GST-BAG-3 but not to GST-BAG-1(ΔC) or several other control proteins. BAG-1 (beginning at residue 116 of SEQ ID NO:2), BAG-2 (SEQ ID NO:4), and BAG-3 (SEQ ID NO:6) also exhibited little or no binding to themselves or to each other, demonstrating that these proteins do not strongly homo- or hetero-dimerize or oligomerize. It should be noted, however, that BAG-2 (SEQ ID NO:4) displayed weak interactions with itself in binding assays and produced a positive result in yeast two-hybrid experiments, demonstrating that it can have the ability to self-associate.

B. Binding of BAG Proteins to Hsc70 In vivo

The ability of BAG-2 (SEQ ID NO:4) and BAG-3 (SEQ ID NO:6) proteins to interact in cells with Hsc70 was tested by expressing these proteins with N-terminal Flag epitope tags in 293T human epithelial cells using co-immunoprecipitation assays as described previously (Takayama et al., supra (1997)). cDNAs encoding the λ-phage cloned regions of BAG-2 and BAG-3 were subcloned in-frame into pcDNA3-Flag. Anti-Flag immune complexes prepared from 293T cells after transfection with plasmids encoding Flag-BAG-1, Flag-BAG-2, or Flag-BAG-3 were analyzed by SDS-PAGE/immunoblot assay. As shown in FIG. 10C, antiserum specific to Hsc70 detected the presence of BAG proteins associated with Hsc70, whereas control immune-complexes prepared with IgG1 as well as anti-Flag immune complexes prepared from cells transfected with Flag-tagged control proteins, Daxx and Apaf-1, did not contain Hsc70 associated protein. These results further demonstrate that BAG-family proteins specifically bind to Hsc70.

C. BIAcore Assay of BAG Protein Binding to the ATPase Domain of Hsc70

BAG-1 (beginning at residue 116 of SEQ ID NO:2) is known to bind tightly to the ATPase domain of Hsc70 (Stuart et al., *J. Biol. Chem.*, In Press (1998)). BAG-2 (SEQ ID NO:4) and BAG-3 (SEQ ID NO:6) proteins were therefore, examined for their ability to bind to Hsc70/ATPase. The affinity and binding kinetics of BAG-2 (SEQ ID NO:4) and BAG-3 (SEQ ID NO:6) to Hsc70/ATPase was also compared to that of BAG-1 (beginning at residue 116 of SEQ ID NO:2) for Hsc70/ATPase, using a surface plasmon resonance technique (BIAcore) which has been described previously (Stuart et al., supra, (1998) which is incorporated herein by reference).

Figure 12:
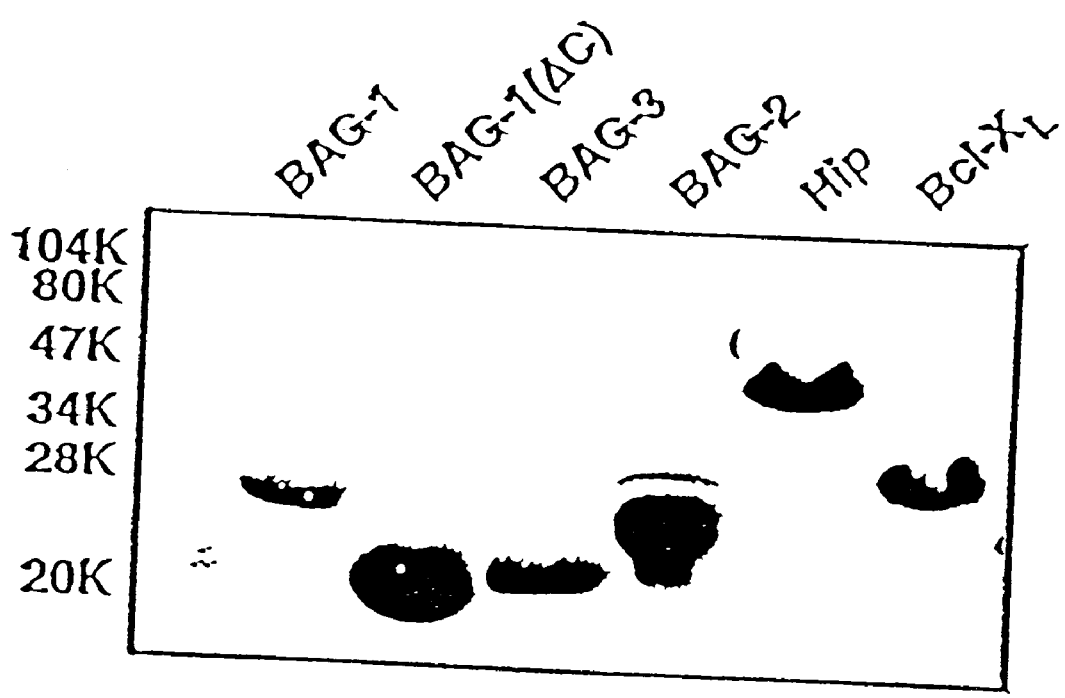
FIG. 12 shows surface plasmon resonance analysis of BAG-family protein interactions with Hsc70/ATPase. (A) SDS-PAGE analysis of purified recombinant proteins. (B) Representative SPR results of biosensor chips containing immobilized BAG proteins with and without maximally bound Hsc70/ATPase.
Figure 13:
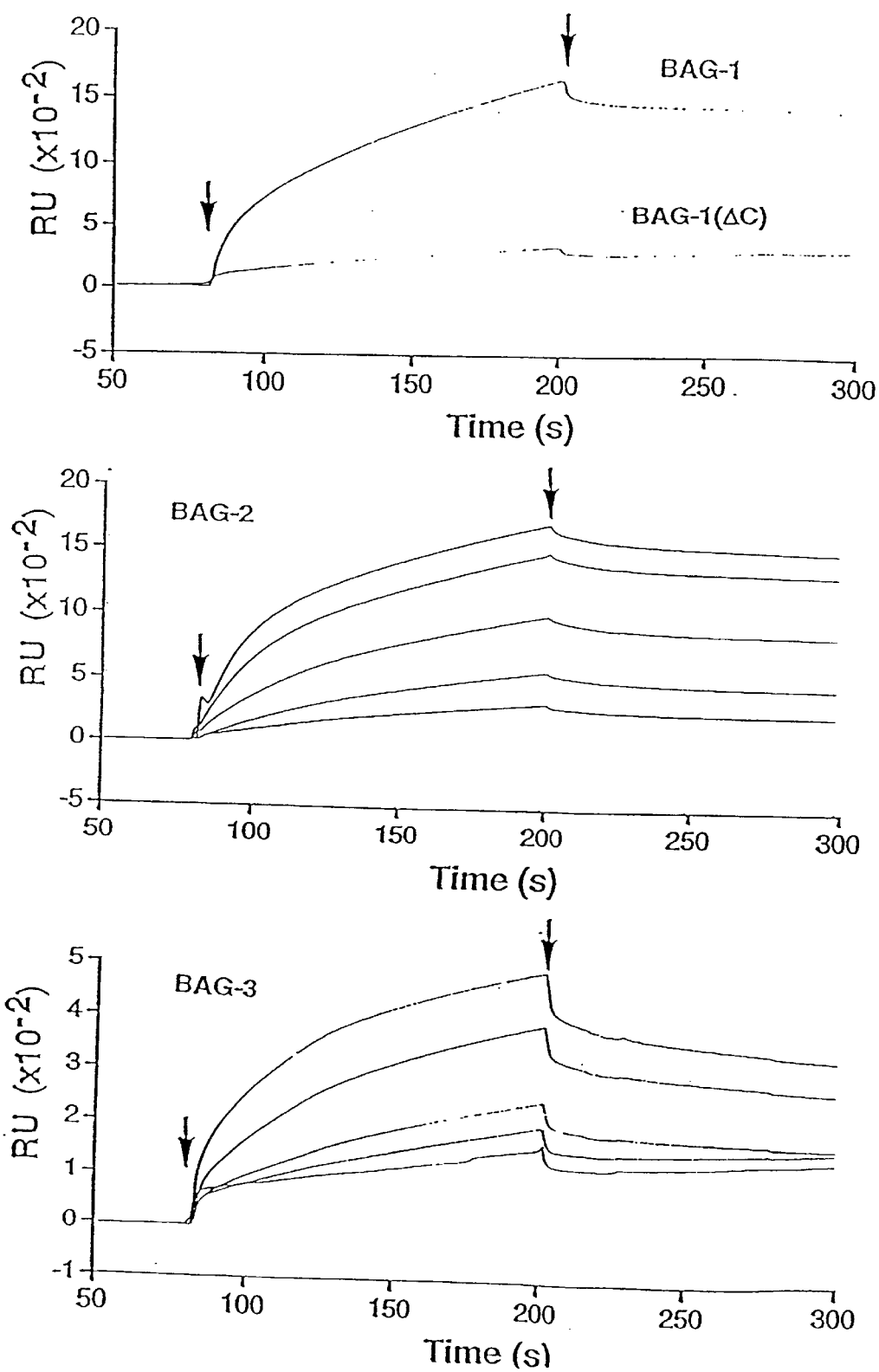
FIG. 13 shows representative SPR results for biosensor chips containing immobilized BAG-1 (beginning at residue 116 at SEQ ID NO:2), BAG-1(ΔC), BAG-2 (SEQ ID NO:4), or BAG-3 (SEQ ID NO:6) proteins. Hsc70/ATPase was flowed over the chips (arrow/left) until maximal binding was reached (response units), then flow was continued without Hsc70/ATPase (arrow/right). For BAG-2 (SEQ ID NO:4) and BAG-3 (SEQ ID NO:6), Hsc70 was injected at 0.0175, 0.035, 0.07, 0.14, and 0.28 μM.
Figure 14:
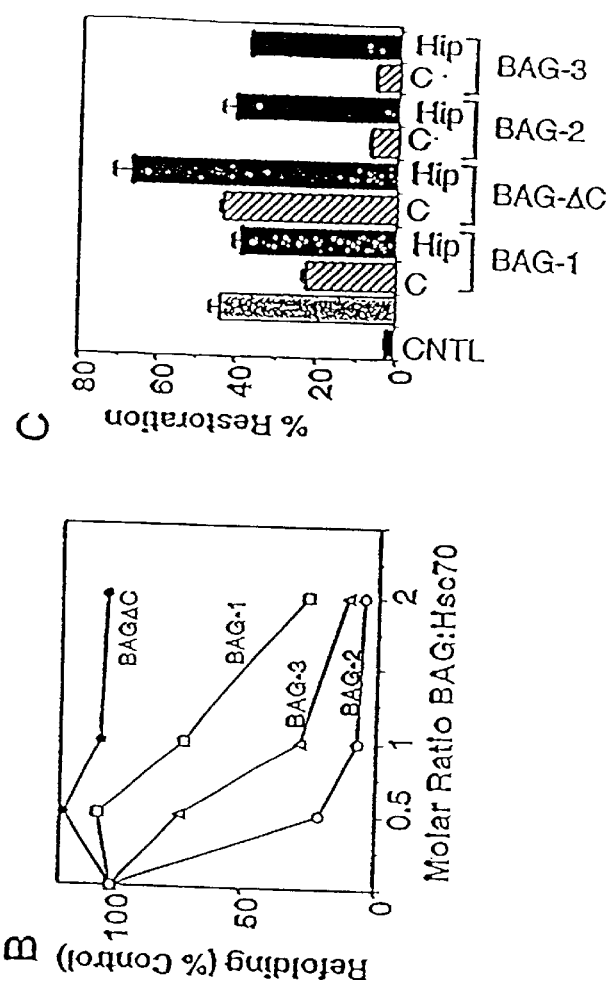
FIG. 14 shows BAG-family protein modulation of Hsc70 chaperone activity. (A) Protein refolding assay of chemically-denatured luciferase by Hsc70 plus DnaJ in the absence or presence of BAG and BAG-mutant proteins. (B) Concentration-dependent inhibition of Hsc70-mediated protein refolding by BAG-family proteins [BAG-1 (beginning at residue 116 of SEQ ID NO:2), BAG-2 (SEQ ID NO:4), BAG-3 (SEQ ID NO:6)] but not by BAG-mutant (BAG-1 (ΔC). (C) Hsc70/Hsp40-mediated refolding of heat-denatured luciferase was assayed in the presence of (black bars) or absence of (striped bars) of 1.8 μM Hip, with (lanes 3–10) or without (lanes 1,2) various BAG-family proteins (1.8 μM) as indicated (mean±SE; n=3). A control (CNTL) is shown (lane 1) in which Hsc70 was replaced with an equivalent amount of BSA.
Figure 18:
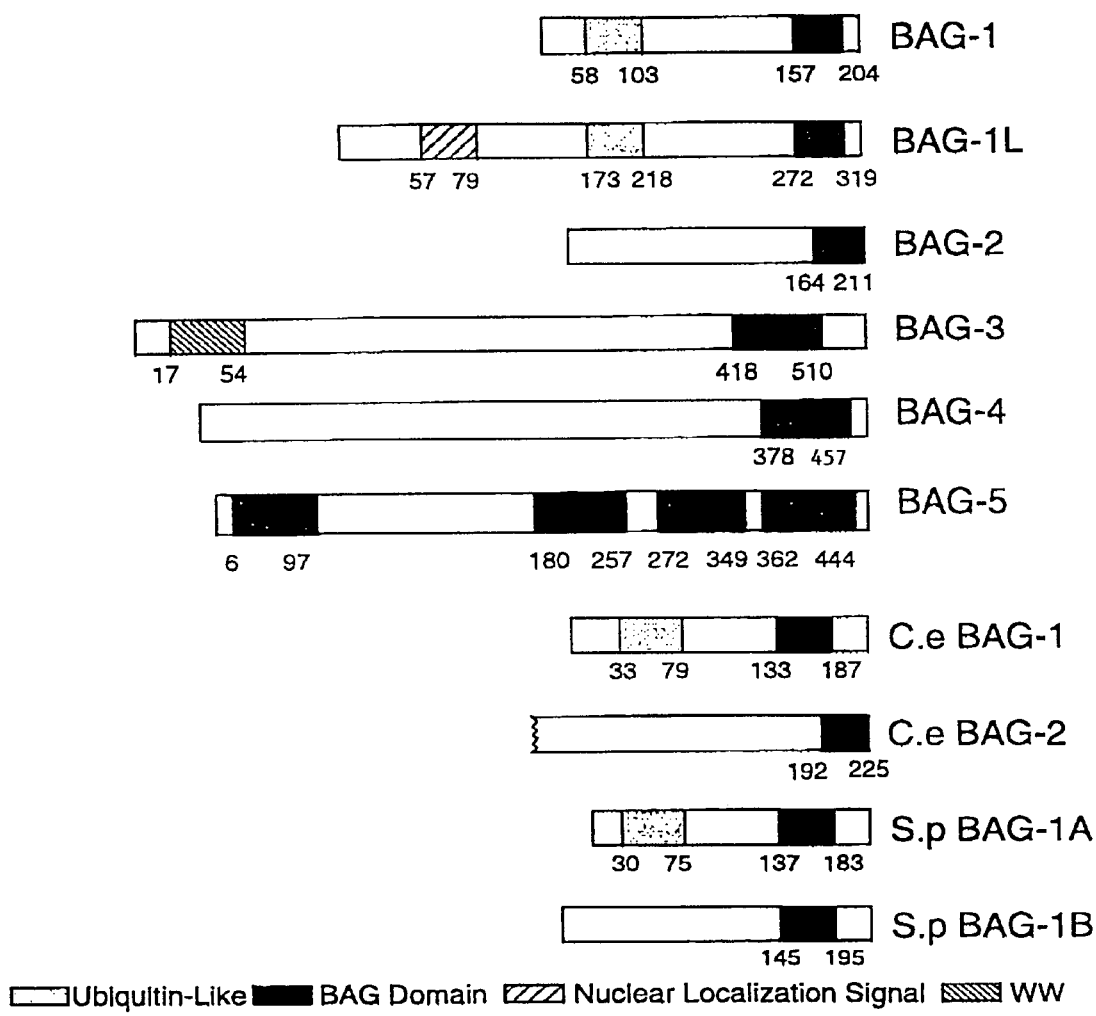
FIG. 18 shows the topologies of the BAG-family proteins; human BAG proteins, BAG-1 (SEQ ID NO:2), BAG-2 (SEQ ID NO:4), expanded BAG-3 (SEQ ID NO:20), expanded BAG-4 (SEQ ID NO:22), expanded BAG-5 (SEQ ID NO:24); S. pombe BAG-1A (SEQ ID NO:16)and BAG-1B (SEQ ID NO:18); and C. elegans BAG-1 (SEQ ID NO:12)and BAG-2 (SEQ ID NO:14). The relative positions of the BAG domains are shown in black, ubiquitin-like regions are represented in gray, WW domain are represented in strips. Nucleoplasmin-like nuclear localization sequence are also shown.

BAG-family proteins were produced in bacteria and purified to near homogeneity as shown in FIG. 12A and described above in Example I. The purified BAG-1 (beginning at residue 116 of SEQ ID NO:2), -2 (SEQ ID NO:4), and -3 (SEQ ID NO:6) proteins were then immobilized on biosensor chips and tested for their interactions with Hsc70 in the soluble phase. Kinetic measurements were performed using a BIAcore-II instrument with CM5 sensor chip and Amine Coupling Kit (Pharmacia Biosensor AB, Sweden). Briefly, for immobilization of proteins, the sensor chip was equilibrated with HK buffer (10 mM Hepes (pH 7.4), 150 mM KCL) at 5 μl/min, then activated by injecting 17 μl of 0.2M N-ethyl-N'-(3-diethylaminopropyl) carbodiimide and 0.05M N-hydroxysuccinimide (NHS/EDC) followed by 35 μl of the protein of interest, in 10 mM acetate, pH 3.5–4.5. Excess NHS-ester on the surface was deactivated with 17 μl 1M ethanolamine-HCL (pH 8.5). After immobilization, 5 μl of regeneration buffer (50 mM phosphate (pH 6.8) and 4M GuHCl) was injected. For binding assays, Hsp70 (Sigma, H8778) was dissolved in HK buffer, and injected at 10 μl/min across the prepared surface at various concentrations. The surface was regenerated after each injection with 5 μl of regeneration buffer. The rate constants $K_{ass}$ and $K_{diss}$ were generated with BIAevaluation softward 3.01 (Pharmacia Biosensor AB). Addition of Hsc70 to chips containing BAG-1 (beginning at residue 116 of SEQ ID NO:2), BAG-2 (SEQ ID NO:4) or BAG-3 (SEQ ID NO:6) resulted in concentration-dependent binding, as reflected by an increase in the Response Units (RU) measured at the chip surface (shown in FIG. 3B). In contrast, Hsc70 failed to display interactions in BIAcore assays with a variety of control proteins as well as a mutant of BAG-1 lacking a C-terminal portion of the BAG domain which is required for Hsc70-binding (FIG. 3B). Furthermore, flowing of various control proteins such as GST, BSA and Bcl-XL over the BAG-1 (beginning at residue 116 of SEQ ID NO:2), BAG-2 (SEQ ID NO:4), or BAG-3 (SEQ ID NO:6) chips resulted in negligible interaction. These results further demonstrate the specificity with which BAG-family proteins interact with and bind to Hsc70.

The rates of Hsc70 binding to BAG-1 (beginning at residue 116 of SEQ ID NO:2), BAG-2 (SEQ ID NO:4), and BAG-3 (SEQ ID NO:6) proteins were similar, following pseudo first-order kinetics with estimated association rate constants ($K_a$) of 2.1, 2.1 and $2.4 \times 10^5$ $M^{-1}$ $sec^{-1}$, respectively. After allowing binding of Hsc70 to immobilized BAG-1 (beginning at residue 116 of SEQ ID NO:2), BAG-2 (SEQ ID NO:4), or BAG-3 (SEQ ID NO:6) to reach plateau levels, the chaperone was removed from the flow solution and the dissociation rate was monitored. BAG-1 (beginning at residue 116 at SEQ ID NO:2) and BAG-2 (SEQ ID NO:4) exhibited similar dissociation rates, with relatively slow loss of Hsc70 from the chip surface, resulting in estimated dissociation rate constants ($K_d$) of 3.0 and $5.0 \times 10^{-4}$ $sec^{-1}$, respectively (see FIG. 3B). In contrast, Hsc70 dissociated more rapidly from biosensor chips containing BAG-3 (see FIG. 3B), yielding an estimated $K_d$ of $1.7 \times 10^{-3}$ $sec^{-1}$. From the kinetic data, the apparent affinities ($K_D = K_d/K_a$) were calculated for binding of Hsc70 to BAG-1 (beginning at residue 116 of SEQ ID NO:2), BAG-2 (SEQ ID NO:4), and BAG-3 (SEQ ID NO:6) and were estimated to equal about $K_D = 1.4$ nM, $K_D = 2.4$ nM, and $K_D = 7.4$ nM, respectively. These results demonstrate that the interactions of BAG-family proteins with Hsc70 occur with apparent affinities sufficient for physiological relevance.

Example III
BAG-family Proteins Inhibit Hsp70/Hsc70-dependent Protein Folding

This example demonstrates that BAG-2 (SEQ ID NO:4) and BAG-3 (SEQ ID NO:6) proteins inhibit Hsp70/Hsc70-dependent refolding of denatured proteins similarly to a BAG-1 (beginning at residue 116 of SEQ ID NO:2) protein.

The effects of BAG-2 (SEQ ID NO:4) and BAG-3 (SEQ ID NO:6) protein on Hsp70/Hsc70-dependent protein refolding was determined using in vitro protein refolding assays similar to those described previously by Takayama et al., supra, 1998; Terada et al., *J. Cell Biol.*, 139:1089–1095, 1997, which are incorporated herein by reference. Briefly, luciferase (20 μM) was denatured in 25 mM Hepes-KOH, pH 7.2, 50 mM potassium acetate, 5 mM DTT, 6M guanidine hydrochloride at ~25° C. for 1 h. Denatured luciferase was diluted 1:40 into 25 mM Hepes-KOH, pH 7.2, 50 mM potassium acetate, 5 mM DTT. Hsc70 (1.8 μM), DnaJ (StressGen, Inc.) (0.9 μM), and various purified recombinant proteins as indicated were added to refolding buffer (30 mM Hepes-KOH, pH 7.6, 120 mM potassium acetate, 3 mM magnesium acetate, 2 mM DTT, 2.5 mM ATP) with 0.2 volume of diluted denatured luciferase to a final concentration of 0.1 μM. Luciferase activity was measured after 1.5 hr incubation at 35° C.

The combination of Hsc70 and DnaJ resulted in ATP-dependent refolding of chemically denatured firefly luciferase, with function of over half the denatured enzyme restored in a 90 minute reaction, as monitored by a chemiluminescence assay. In contrast, neither Hsc70 nor DnaJ alone were able to induce substantial refolding of denatured luciferase. Furthermore, little spontaneous restoration of luciferase activity was observed with control proteins, BSA, GST or Bcl-XL (see FIG. 4A).

Addition of recombinant purified BAG-1 (beginning at residue 116 of SEQ ID NO:2), BAG-2 (SEQ ID NO:4), or BAG-3 (SEQ ID NO:6) to the above assays in amounts equimolar to Hsc70 (1.8 μM) resulted in striking inhibition of luciferase refolding. BAG-2 (SEQ ID NO:4) and BAG-3 (SEQ ID NO:6) displayed somewhat greater inhibitory activity than BAG-1 (beginning at residue 116 of SEQ ID NO:2) as shown in FIG. 4A. In contrast, the BAG-1 (ΔC) protein, which fails to bind Hsc70 as well as several other control proteins, had no effect on luciferase refolding.

In an additional refolding assay, described previously by Minami et al., *J Biol. Chem.* 271:19617–24, 1996), purified Hsc70 and human DnaJ homolog Hdj-1 (Hsp 40) were used with additional cofactors provided in reticulocyte lysates (5% v:v) to produce a system capable of refolding denatured luciferase. Briefly, additional cofactors included, recombinant Luciferase (Promega: QuantiLum TM), that had been heat denatured at 42° C. for 10 min, 1.8 μM Hsc70 (Sigma; purified from bovine brain), 0.9 μM Hsp40, and various recombinant purified proteins. Luciferase activity was measured (Promega luciferase assay kit) using a luminometer (EG&G Berthold, MicroLumat luminometer, Model #LB96P). All results were normalized relative to non-denatured luciferase that had been subjected to the same conditions. Control reactions lacking ATP, Hsc70, or Hsp40 resulted in negligible luciferase refolding.

Various amounts of purified BAG-1 (beginning at residue 116 of SEQ ID NO:2), BAG-2 (SEQ ID NO:4), or BAG-3 (SEQ ID NO:6), relative to amounts of Hsc70 were used in the above-described protein refolding assay. Addition of BAG-family proteins resulted in a concentration-dependent inhibition of Hsc70 chaperone activity. Furthermore, the BAG-2 (SEQ ID NO:4) and BAG-3 (SEQ ID NO:6) inhibition of Hsc70 chaperone activity was demonstrated to be as potent as that observed for BAG-1 (beginning at residue 116 of SEQ ID NO:2). In contrast, the BAG-1 (ΔC) mutant as well as other control proteins did not suppress Hsc70-mediated refolding of denatured luciferase. These results indicate that BAG-2 (SEQ ID NO:4) and BAG-3 (SEQ ID NO:6) can inhibit Hsc70/Hsp70 dependent protein refolding activity to the same extent as BAG-1 (beginning at residue 116 of SEQ ID NO:2).

B. BAG Competes with Hip for Binding to Hsc70.

It is known that BAG-1 competes with Hip for binding to Hsc70, with these proteins exerting opposite effects on Hsc70-mediated protein refolding (Hohfeld, J., and Jentsch, S., *Embo J.*, 16:6209–6216, 1997, which is incorporated herein by reference). In order to determine whether BAG-2 (SEQ ID NO:4) and BAG-3 (SEQ ID NO:6) also compete with Hip for binding to Hsc70, refolding assays were performed as described above in the presence of Hip protein.

Hip was purified as $His_6$-protein. The fusion protein was induced from pET28-Hip (V. Prapapanich et al., *Mol Cell Biol.*, 18:944–952, 1998, which is incorporated herein by reference) with 0.1 mM IPTG at 25° C. for 6 h in BL21 cells. Cells from 1L of culture were resuspended into 50 ml of 50 mM Phosphate buffer (pH 6.8), 150 mM NaCl, and 1% (v/v) Tween-20 and then incubated with 0.5 mg/ml lysozyme at 25° C. for 0.5 h, followed by sonication. After centrifugation at 27,500 g for 10 min, the resulting supernatant was mixed with 15 ml nickel resin (Qiagen, Inc.) at 4° C. for 3 h with 25 mM imidazol. The resin was then washed with 50 mM phosphate buffer (pH 6.8), 25 mM imidazol, 150 mM NaCl and 0.1% Tween-20 until the OD280 nm reached a value of <0.01. $His_6$-Hip protein was eluted with 250 mM imidazol in washing buffer (Qiagene, Inc.) and purified on Mono Q (HR10/10 Pharmacia) by FPLC using a linear gradient of 0.5M NaCl at pH 8.0, followed by dialysis in chaperone assay buffer.

In the refolding assay reactions, addition of purified Hip at equimolar concentrations relative to BAG-1 (beginning at residue 116 of SEQ ID NO:2), BAG-2 (SEQ ID NO:4), or BAG-3 (SEQ ID NO:6) (1.8 μM) completely negated the inhibitory effects of the BAG-family proteins on refolding of denatured luciferase (see FIG. 4C). These results demonstrate that the suppression of Hsc70 chaperone activity by BAG-family proteins is reversible, and that Hip antagonizes the effects of not only BAG-1 (beginning at residue 116 of SEQ ID NO:2), but also of BAG-2 (SEQ ID NO:4) and BAG-3 (SEQ ID NO:6).

In summary, these results demonstrate that BAG-family proteins all contain a conserved BAG domain near their C-terminus that binds Hsc70/Hsp70, and that human BAG-family proteins can bind with high affinity to the ATPase domain of Hsc70 and inhibit its chaperone activity through a Hip-repressable mechanism.

Example IV
Expanded Nucleic Acid and Amino Acid Sequences for Human BAG-3, BAG-4 and BAG-5

Figure 15C:
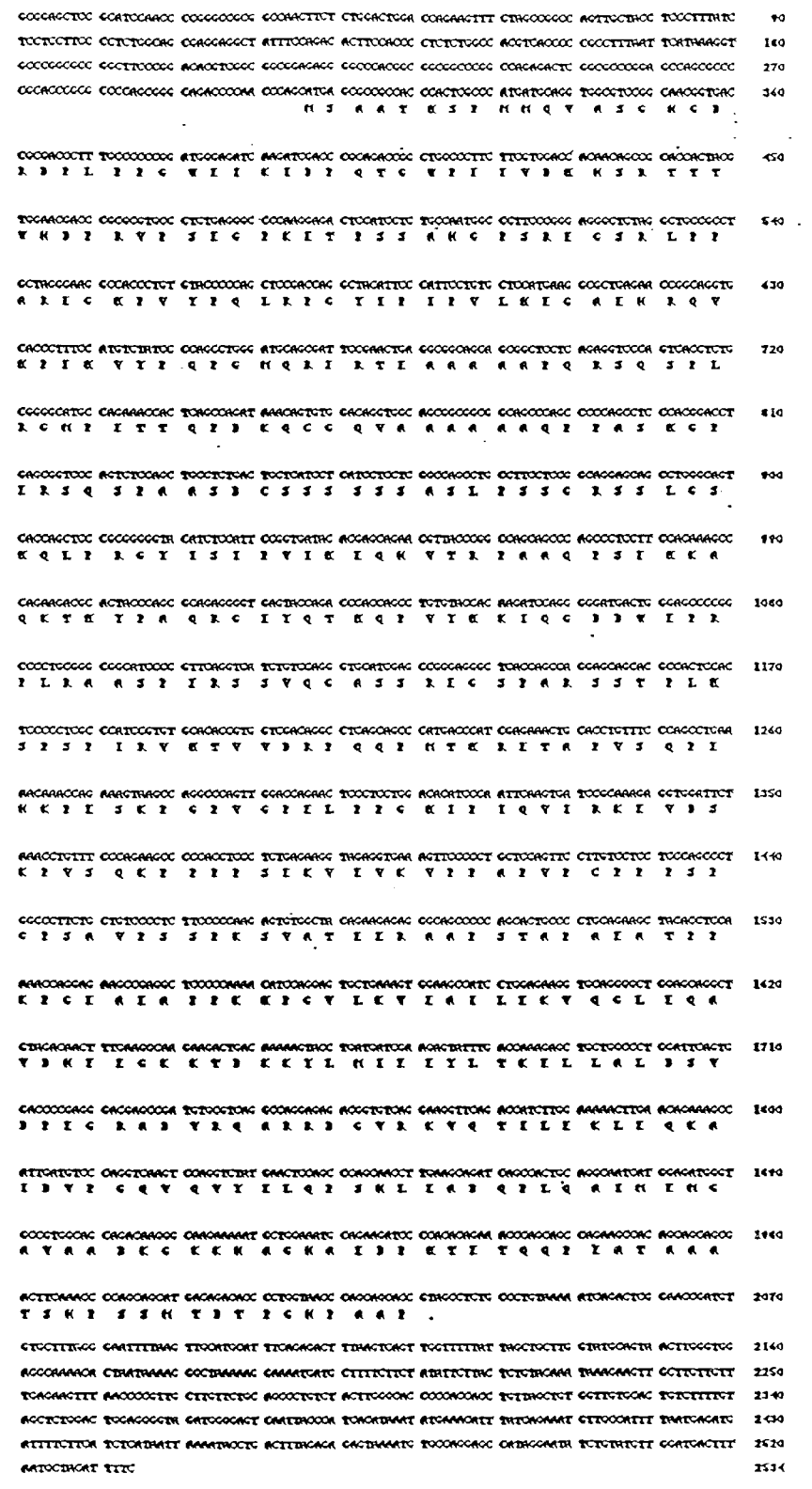
Figure 16C:
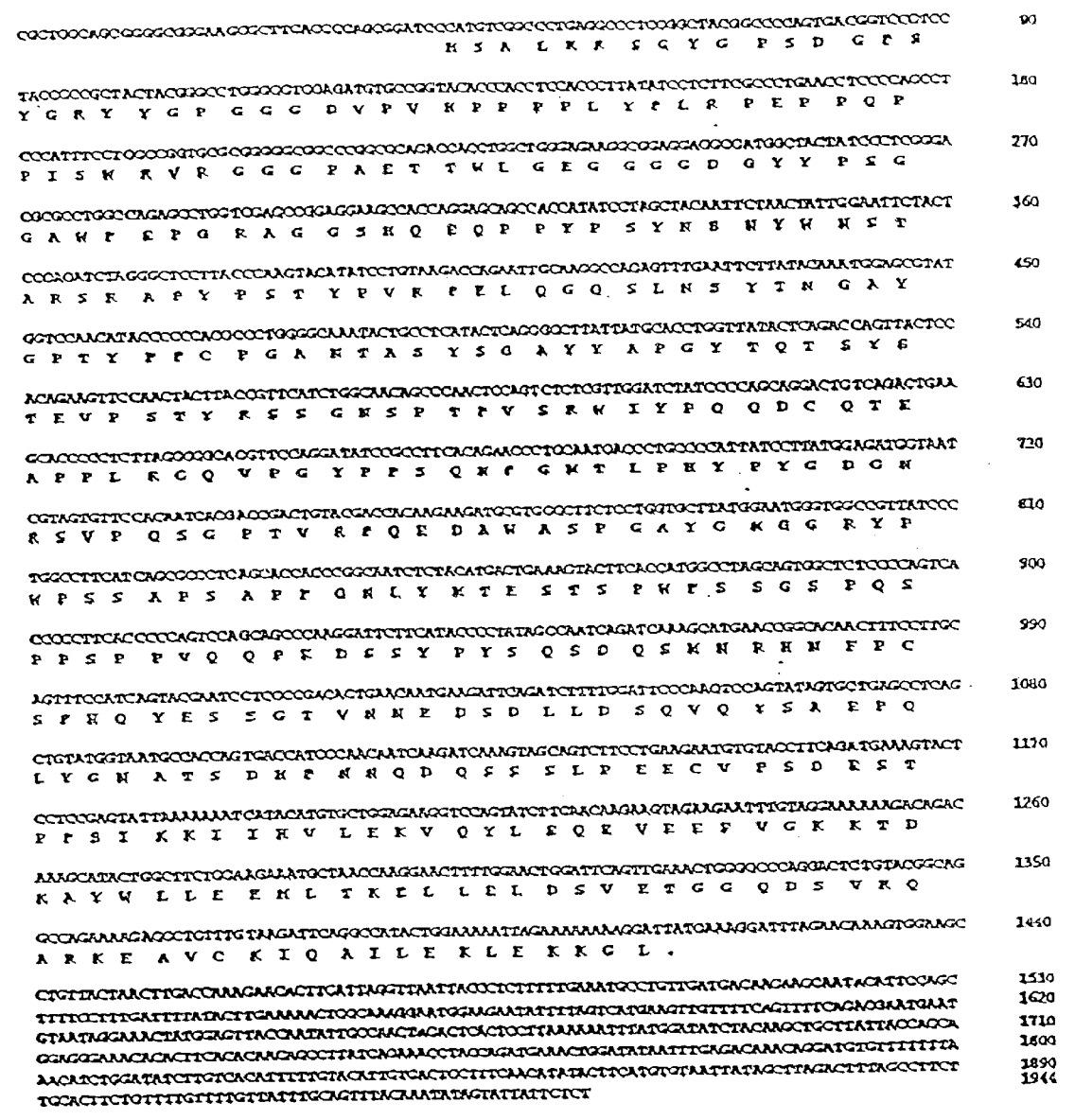

Following the procedures disclosed herein, the nucleic acid and amino acids sequences to human BAG-3, BAG-4 and BAG-5 were further expanded. The expanded sequences for BAG-3, BAG-4 and BAG-5 are shown in FIGS. 15, 16 and 17, respectively, with their respective sequence identification numbers, "SEQ ID NO"s.

We claim:

1. A substantially purified and isolated nucleic acid molecule, having the nucleotide sequence set forth in SEQ ID NO:1.

2. A substantially purified and isolated nucleic acid molecule, having a nucleotide sequence comprising 46–1291 of the sequence set forth in SEQ ID NO:1.

* * * * *

SEQUENCE LISTING

<160> NUMBER OF SEQ ID NOS: 24

<210> SEQ ID NO 1
<211> LENGTH: 1291
<212> TYPE: DNA
<213> ORGANISM: Homo sapiens
<220> FEATURE:
<221> NAME/KEY: CDS
<222> LOCATION: (46)..(1080)

<400> SEQUENCE: 1

```
        acgccgcgct cagcttccat cgctgggcgg tcaacaagtg cgggc ctg gct cag cgc    57
                                                         Leu Ala Gln Arg
                                                           1
ggg ggg gcg cgg aga ccg cga ggc gac cgg gag cgg ctg ggt tcc cgg      105
Gly Gly Ala Arg Arg Pro Arg Gly Asp Arg Glu Arg Leu Gly Ser Arg
  5                  10                  15                  20
ctg cgc gcc ctt cgg cca ggc cgg gag ccg cgc cag tcg gag ccc ccg      153
Leu Arg Ala Leu Arg Pro Gly Arg Glu Pro Arg Gln Ser Glu Pro Pro
                 25                  30                  35
gcc cag cgt ggt ccg cct ccc tct cgg cgt cca cct gcc cgg agt act      201
Ala Gln Arg Gly Pro Pro Pro Ser Arg Arg Pro Pro Ala Arg Ser Thr
             40                  45                  50
gcc agc ggg cat gac cga ccc acc agg ggc gcc gcc gcc ggc gct cgc      249
Ala Ser Gly His Asp Arg Pro Thr Arg Gly Ala Ala Ala Gly Ala Arg
         55                  60                  65
agg ccg cgg atg aag aag aaa acc cgg cgc cgc tcg acc cgg agc gag      297
Arg Pro Arg Met Lys Lys Lys Thr Arg Arg Arg Ser Thr Arg Ser Glu
     70                  75                  80
gag ttg acc cgg agc gag gag ttg acc ctg agt gag gaa gcg acc tgg      345
Glu Leu Thr Arg Ser Glu Glu Leu Thr Leu Ser Glu Glu Ala Thr Trp
 85                  90                  95                 100
agt gaa gag gcg acc cag agt gag gag gcg acc cag ggc gaa gag atg      393
Ser Glu Glu Ala Thr Gln Ser Glu Glu Ala Thr Gln Gly Glu Glu Met
                105                 110                 115
aat cgg agc cag gag gtg acc cgg gac gag gag tcg acc cgg agc gag      441
Asn Arg Ser Gln Glu Val Thr Arg Asp Glu Glu Ser Thr Arg Ser Glu
            120                 125                 130
gag gtg acc agg gag gaa atg gcg gca gct ggg ctc acc gtg act gtc      489
Glu Val Thr Arg Glu Glu Met Ala Ala Ala Gly Leu Thr Val Thr Val
        135                 140                 145
acc cac agc aat gag aag cac gac ctt cat gtt acc tcc cag cag ggc      537
Thr His Ser Asn Glu Lys His Asp Leu His Val Thr Ser Gln Gln Gly
    150                 155                 160
agc agt gaa cca gtt gtc caa gac ctg gcc cag gtt gtt gaa gag gtc      585
Ser Ser Glu Pro Val Val Gln Asp Leu Ala Gln Val Val Glu Glu Val
165                 170                 175                 180
ata ggg gtt cca cag tct ttt cag aaa ctc ata ttt aag gga aaa tct      633
Ile Gly Val Pro Gln Ser Phe Gln Lys Leu Ile Phe Lys Gly Lys Ser
                185                 190                 195
ctg aag gaa atg gaa aca ccg ttg tca gca ctt gga ata caa gat ggt      681
Leu Lys Glu Met Glu Thr Pro Leu Ser Ala Leu Gly Ile Gln Asp Gly
            200                 205                 210
tgc cgg gtc atg tta att ggg aaa aag aac agt cca cag gaa gag gtt      729
Cys Arg Val Met Leu Ile Gly Lys Lys Asn Ser Pro Gln Glu Glu Val
        215                 220                 225
gaa cta aag aag ttg aaa cat ttg gag aag tct gtg gag aag ata gct      777
Glu Leu Lys Lys Leu Lys His Leu Glu Lys Ser Val Glu Lys Ile Ala
    230                 235                 240
gac cag ctg gaa gag ttg aat aaa gag ctt act gga atc cag cag ggt      825
Asp Gln Leu Glu Glu Leu Asn Lys Glu Leu Thr Gly Ile Gln Gln Gly
245                 250                 255                 260
ttt ctg ccc aag gat ttg caa gct gaa gct ctc tgc aaa ctt gat agg      873
```

-continued

```
        Phe Leu Pro Lys Asp Leu Gln Ala Glu Ala Leu Cys Lys Leu Asp Arg
                        265                 270                 275
        aga gta aaa gcc aca ata gag cag ttt atg aag atc ttg gag gag att    921
        Arg Val Lys Ala Thr Ile Glu Gln Phe Met Lys Ile Leu Glu Glu Ile
                    280                 285                 290
        gac aca ctg atc ctg cca gaa aat ttc aaa gac agt aga ttg aaa agg    969
        Asp Thr Leu Ile Leu Pro Glu Asn Phe Lys Asp Ser Arg Leu Lys Arg
                295                 300                 305
        aaa ggc ttg gta aaa aag gtt cag gca ttc cta gcc gag tgt gac aca   1017
        Lys Gly Leu Val Lys Lys Val Gln Ala Phe Leu Ala Glu Cys Asp Thr
            310                 315                 320
        gtg gag cag aac atc tgc cag gag act gag cgg ctg cag tct aca aac   1065
        Val Glu Gln Asn Ile Cys Gln Glu Thr Glu Arg Leu Gln Ser Thr Asn
        325                 330                 335                 340
        ttt gcc ctg gcc gag tgaggtgtag cagaaaaagg ctgtgctgcc ctgaagaatg   1120
        Phe Ala Leu Ala Glu
                        345
        gcgccaccag ctctgccgtc tctggatcgg aatttacctg atttcttcag ggctgctggg 1180
        ggcaactggc catttgccaa ttttcctact ctcacactgg ttctcaatga aaaatagtgt 1240
        ctttgtgatt tgagtaaagc tcctattctg tttttcacaa aaaaaaaaa a           1291

<210> SEQ ID NO 2
<211> LENGTH: 345
<212> TYPE: PRT
<213> ORGANISM: Homo sapiens

<400> SEQUENCE: 2

Leu Ala Gln Arg Gly Gly Ala Arg Arg Pro Arg Gly Asp Arg Glu Arg
        1               5                   10                  15
        Leu Gly Ser Arg Leu Arg Ala Leu Arg Pro Gly Arg Glu Pro Arg Gln
                    20                  25                  30
        Ser Glu Pro Pro Ala Gln Arg Gly Pro Pro Ser Arg Arg Pro Pro
                35                  40                  45
        Ala Arg Ser Thr Ala Ser Gly His Asp Arg Pro Thr Arg Gly Ala Ala
            50                  55                  60
        Ala Gly Ala Arg Arg Pro Arg Met Lys Lys Thr Arg Arg Arg Ser
        65                  70                  75                  80
        Thr Arg Ser Glu Glu Leu Thr Arg Ser Glu Glu Leu Thr Leu Ser Glu
                        85                  90                  95
        Glu Ala Thr Trp Ser Glu Glu Ala Thr Gln Ser Glu Glu Ala Thr Gln
                    100                 105                 110
        Gly Glu Glu Met Asn Arg Ser Gln Glu Val Thr Arg Asp Glu Glu Ser
                115                 120                 125
        Thr Arg Ser Glu Glu Val Thr Arg Glu Glu Met Ala Ala Ala Gly Leu
            130                 135                 140
        Thr Val Thr Val Thr His Ser Asn Glu Lys His Asp Leu His Val Thr
        145                 150                 155                 160
        Ser Gln Gln Gly Ser Ser Glu Pro Val Val Gln Asp Leu Ala Gln Val
                        165                 170                 175
        Val Glu Glu Val Ile Gly Val Pro Gln Ser Phe Gln Lys Leu Ile Phe
                    180                 185                 190
        Lys Gly Lys Ser Leu Lys Glu Met Glu Thr Pro Leu Ser Ala Leu Gly
                195                 200                 205
        Ile Gln Asp Gly Cys Arg Val Met Leu Ile Gly Lys Lys Asn Ser Pro
            210                 215                 220
        Gln Glu Glu Val Glu Leu Lys Lys Leu Lys His Leu Glu Lys Ser Val
        225                 230                 235                 240
        Glu Lys Ile Ala Asp Gln Leu Glu Glu Leu Asn Lys Glu Leu Thr Gly
                        245                 250                 255
        Ile Gln Gln Gly Phe Leu Pro Lys Asp Leu Gln Ala Glu Ala Leu Cys
                    260                 265                 270
        Lys Leu Asp Arg Arg Val Lys Ala Thr Ile Glu Gln Phe Met Lys Ile
                275                 280                 285
        Leu Glu Glu Ile Asp Thr Leu Ile Leu Pro Glu Asn Phe Lys Asp Ser
            290                 295                 300
        Arg Leu Lys Arg Lys Gly Leu Val Lys Lys Val Gln Ala Phe Leu Ala
        305                 310                 315                 320
        Glu Cys Asp Thr Val Glu Gln Asn Ile Cys Gln Glu Thr Glu Arg Leu
                        325                 330                 335
        Gln Ser Thr Asn Phe Ala Leu Ala Glu
                    340                 345

<210> SEQ ID NO 3
<211> LENGTH: 1179
<212> TYPE: DNA
<213> ORGANISM: Homo sapiens
```

```
<220> FEATURE:
<221> NAME/KEY: CDS
<222> LOCATION: (160)..(792)

<400> SEQUENCE: 3
gcagccgcgg tgtcgcgaag tcctcccggg ttgccccgc ggcgtcagag ggagggcggg    60
        cgccgcgttg gtgacggcga ccctgcagcc caaggagcgc tccactcgct gccgccggag   120
        ggccggtgac ctcttggcta ccccgcgtcg gaggcttag atg gct cag gcg aag       174
                                                   Met Ala Gln Ala Lys
                                                     1               5
        atc aac gct aaa gcc aac gag ggg cgc ttc tgc cgc tcc tcc tcc atg     222
        Ile Asn Ala Lys Ala Asn Glu Gly Arg Phe Cys Arg Ser Ser Ser Met
                     10                  15                  20
        gct gac cgc tcc agc cgc ctg ctg gag agc ctg gac cag ctg gag ctc     270
        Ala Asp Arg Ser Ser Arg Leu Leu Glu Ser Leu Asp Gln Leu Glu Leu
                 25                  30                  35
        agg gtt gaa gct ttg aga gaa gca gca act gct gtt gag caa gag aaa     318
        Arg Val Glu Ala Leu Arg Glu Ala Ala Thr Ala Val Glu Gln Glu Lys
             40                  45                  50
        gaa atc ctt ctg gaa atg atc cac agt atc caa aat agc cag gac atg     366
        Glu Ile Leu Leu Glu Met Ile His Ser Ile Gln Asn Ser Gln Asp Met
         55                  60                  65
        agg cag atc agt gac gga gaa aga gaa gaa tta aat ctg act gca aac     414
        Arg Gln Ile Ser Asp Gly Glu Arg Glu Glu Leu Asn Leu Thr Ala Asn
         70                  75                  80                  85
        cgt ttg atg gga aga act ctc acc gtt gaa gtg tca gta gaa aca att     462
        Arg Leu Met Gly Arg Thr Leu Thr Val Glu Val Ser Val Glu Thr Ile
                     90                  95                 100
        aga aac ccc cag cag caa gaa tcc cta aag cat gcc aca agg att att     510
        Arg Asn Pro Gln Gln Gln Glu Ser Leu Lys His Ala Thr Arg Ile Ile
                    105                 110                 115
        gat gag gtg gtc aat aag ttt ctg gat gat ttg gga aat gcc aag agt     558
        Asp Glu Val Val Asn Lys Phe Leu Asp Asp Leu Gly Asn Ala Lys Ser
                120                 125                 130
        cat tta atg tcg ctc tac agt gca tgt tca tct gag gtg cca cat ggg     606
        His Leu Met Ser Leu Tyr Ser Ala Cys Ser Ser Glu Val Pro His Gly
            135                 140                 145
        cca gtt gat cag aag ttt caa tcc ata gta att ggc tgt gct ctt gaa     654
        Pro Val Asp Gln Lys Phe Gln Ser Ile Val Ile Gly Cys Ala Leu Glu
        150                 155                 160                 165
        gat cag aag aaa att aag aga aga tta gag act ctg ctt aga aat att     702
        Asp Gln Lys Lys Ile Lys Arg Arg Leu Glu Thr Leu Leu Arg Asn Ile
                        170                 175                 180
        gaa aac tct gac aag gcc atc aag cta tta gag cat tct aaa gga gct     750
        Glu Asn Ser Asp Lys Ala Ile Lys Leu Leu Glu His Ser Lys Gly Ala
                    185                 190                 195
        ggt tcc aaa act ctg caa caa aat gct gaa agc aga ttc aat                 792
        Gly Ser Lys Thr Leu Gln Gln Asn Ala Glu Ser Arg Phe Asn
                200                 205                 210
        tagtcttcaa acctaagagc atttacacaa tacacaaggt gtaaaaatga taaatacta    852
        tttaattga taactagttc tttgttaggt ataaccactt agttgacact gatagttgtt    912
        tcagatgagg aaaatattcc atcaagtatc ttcagtttg tgaataacaa aactagcaat    972
        atttaatta tctatctaga gattttttag attgaattct tgtcttgtac taggatctag   1032
        catatttcac tattctgtgg atgaatacat agtttgtggg gaaaacaaac gttcagctag   1092
        gggcaaaaag catgactgct ttttcctgtc tggcatggaa tcacgcagtc accttgggca   1152
        tttagtttac tagaaattct ttactgg                                       1179

<210> SEQ ID NO 4
<211> LENGTH: 211
<212> TYPE: PRT
<213> ORGANISM: Homo sapiens

<400> SEQUENCE: 4

Met Ala Gln Ala Lys Ile Asn Ala Lys Ala Asn Glu Gly Arg Phe Cys
          1               5                  10                  15
        Arg Ser Ser Ser Met Ala Asp Arg Ser Ser Arg Leu Leu Glu Ser Leu
                         20                  25                  30
        Asp Gln Leu Glu Leu Arg Val Glu Ala Leu Arg Glu Ala Ala Thr Ala
                     35                  40                  45
        Val Glu Gln Glu Lys Glu Ile Leu Leu Glu Met Ile His Ser Ile Gln
                 50                  55                  60
        Asn Ser Gln Asp Met Arg Gln Ile Ser Asp Gly Glu Arg Glu Glu Leu
             65                  70                  75                  80
        Asn Leu Thr Ala Asn Arg Leu Met Gly Arg Thr Leu Thr Val Glu Val
                         85                  90                  95
        Ser Val Glu Thr Ile Arg Asn Pro Gln Gln Gln Glu Ser Leu Lys His
```

```
            100                 105                 110
Ala Thr Arg Ile Ile Asp Glu Val Val Asn Lys Phe Leu Asp Asp Leu
        115                 120                 125
Gly Asn Ala Lys Ser His Leu Met Ser Leu Tyr Ser Ala Cys Ser Ser
    130                 135                 140
Glu Val Pro His Gly Pro Val Asp Gln Lys Phe Gln Ser Ile Val Ile
145                 150                 155                 160
Gly Cys Ala Leu Glu Asp Gln Lys Lys Ile Lys Arg Arg Leu Glu Thr
                165                 170                 175
Leu Leu Arg Asn Ile Glu Asn Ser Asp Lys Ala Ile Lys Leu Leu Glu
            180                 185                 190
His Ser Lys Gly Ala Gly Ser Lys Thr Leu Gln Gln Asn Ala Glu Ser
        195                 200                 205
Arg Phe Asn
    210

<210> SEQ ID NO 5
<211> LENGTH: 2528
<212> TYPE: DNA
<213> ORGANISM: Homo sapiens
<220> FEATURE:
<221> NAME/KEY: CDS
<222> LOCATION: (1)..(2031)
<221> NAME/KEY: misc_feature
<222> LOCATION: (1)..(2528)
<223> OTHER INFORMATION: n= a, c, t or g

<400> SEQUENCE: 5 gcg gag ctc cgc atc caa ccc cgg gcc gcg gcc aac ttc tct gga ctg    48
Ala Glu Leu Arg Ile Gln Pro Arg Ala Ala Ala Asn Phe Ser Gly Leu
  1               5                  10                  15
gac cag aag ttt cta gcc ggc cag ttg cta cct ccc ttt atc tcc tcc    96
Asp Gln Lys Phe Leu Ala Gly Gln Leu Leu Pro Pro Phe Ile Ser Ser
                 20                  25                  30
ttc ccc tct ggc agc gag gag gct att tcc aga cac ttc cac ccc tct   144
Phe Pro Ser Gly Ser Glu Glu Ala Ile Ser Arg His Phe His Pro Ser
             35                  40                  45
ctg gcc acg tca ccc ccg cct tta att cat aaa ggt gcc cgg cgc cgg   192
Leu Ala Thr Ser Pro Pro Pro Leu Ile His Lys Gly Ala Arg Arg Arg
         50                  55                  60
ctt ccc gga cac gtc ggc ggc gga gag ggg ccc acg gcg gcg gcc cgg   240
Leu Pro Gly His Val Gly Gly Gly Glu Gly Pro Thr Ala Ala Ala Arg
 65                  70                  75                  80
cca gag act cgg cgc ccg gag cca gcg ccc cgc acc cgc gcc cca gcg   288
Pro Glu Thr Arg Arg Pro Glu Pro Ala Pro Arg Thr Arg Ala Pro Ala
                 85                  90                  95
ggc aga ccc caa ccc agc atg agc gcc gcc acc cac tcg ccc atg atg   336
Gly Arg Pro Gln Pro Ser Met Ser Ala Ala Thr His Ser Pro Met Met
            100                 105                 110
cag gtg gcg tcc ggc aac ggt gac cgc gac cct ttg ccc ccg gga tgg   384
Gln Val Ala Ser Gly Asn Gly Asp Arg Asp Pro Leu Pro Pro Gly Trp
        115                 120                 125
gag atc aag atc gac ccg cag acc ggc tgg ccc ttc ttc gtg gac cac   432
Glu Ile Lys Ile Asp Pro Gln Thr Gly Trp Pro Phe Phe Val Asp His
    130                 135                 140
aac agc cgc acc act acg tgg aac gac ccg cgc gtg ccc tct gag ggc   480
Asn Ser Arg Thr Thr Thr Trp Asn Asp Pro Arg Val Pro Ser Glu Gly
145                 150                 155                 160
ccc aag gag act cca tcc tct gcc aat ggc cct tcc cgg gag ggc tct   528
Pro Lys Glu Thr Pro Ser Ser Ala Asn Gly Pro Ser Arg Glu Gly Ser
                165                 170                 175
agg ctg ccg cct gct agg gaa ggc cac cct gtg tac ccc cag ctc cga   576
Arg Leu Pro Pro Ala Arg Glu Gly His Pro Val Tyr Pro Gln Leu Arg
            180                 185                 190
cca ggc tac att ccc att cct gtg ctc cat gaa ggc gct gag aac cgg   624
Pro Gly Tyr Ile Pro Ile Pro Val Leu His Glu Gly Ala Glu Asn Arg
        195                 200                 205
cag gtg cac cct ttc cat gtc tat ccc cag cct ggg atg cag cga ttc   672
Gln Val His Pro Phe His Val Tyr Pro Gln Pro Gly Met Gln Arg Phe
    210                 215                 220
cga act gag gcg gca gca gcg gct cct cag agg tcc cag tca cct ctg   720
Arg Thr Glu Ala Ala Ala Ala Ala Pro Gln Arg Ser Gln Ser Pro Leu
225                 230                 235                 240
cgg ggc atg cca gaa acc act cag cca gat aaa cag tgt gga cag gtg   768
Arg Gly Met Pro Glu Thr Thr Gln Pro Asp Lys Gln Cys Gly Gln Val
                245                 250                 255
gca gcg gcg gcg gca gcc cag ccc cca gcc tcc cac gga cct gag cgg   816
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Ala | Ala | Ala | Ala | Ala | Ala | Gln | Pro | Pro | Ala | Ser | His | Gly | Pro | Glu | Arg |     |
|     |     |     |     | 260 |     |     |     |     | 265 |     |     |     |     | 270 |     |     |
| tcc | cag | tct | cca | gct | gcc | tct | gac | tgc | tca | tcc | tca | tcc | tcc | tcg | gcc | 864 |
| Ser | Gln | Ser | Pro | Ala | Ala | Ser | Asp | Cys | Ser | Ser | Ser | Ser | Ser | Ser | Ala |     |
|     |     | 275 |     |     |     |     | 280 |     |     |     |     | 285 |     |     |     |     |
| agc | ctg | cct | tcc | tcc | ggc | agg | agc | agc | ctg | ggc | agt | cac | cag | ctc | ccg | 912 |
| Ser | Leu | Pro | Ser | Ser | Gly | Arg | Ser | Ser | Leu | Gly | Ser | His | Gln | Leu | Pro |     |
|     | 290 |     |     |     |     | 295 |     |     |     |     | 300 |     |     |     |     |     |
| cgg | ggg | tac | atc | tcc | att | ccg | gtg | ata | cac | gag | cag | aac | gtt | acc | cgg | 960 |
| Arg | Gly | Tyr | Ile | Ser | Ile | Pro | Val | Ile | His | Glu | Gln | Asn | Val | Thr | Arg |     |
| 305 |     |     |     |     | 310 |     |     |     |     | 315 |     |     |     |     | 320 |     |
| cca | gca | gcc | cag | ccc | tcc | ttc | cac | aaa | gcc | cag | aag | acg | cac | tac | cca | 1008 |
| Pro | Ala | Ala | Gln | Pro | Ser | Phe | His | Lys | Ala | Gln | Lys | Thr | His | Tyr | Pro |     |
|     |     |     | 325 |     |     |     |     | 330 |     |     |     |     | 335 |     |     |     |
| gcg | cag | agg | ggt | gag | tac | cag | acc | cac | cag | cct | gtg | tac | cac | aag | atc | 1056 |
| Ala | Gln | Arg | Gly | Glu | Tyr | Gln | Thr | His | Gln | Pro | Val | Tyr | His | Lys | Ile |     |
|     |     |     | 340 |     |     |     |     | 345 |     |     |     |     | 350 |     |     |     |
| cag | ggg | gat | gac | tgg | gag | ccc | cgg | ccc | ctg | cgg | gcg | gca | tcc | ccg | ttc | 1104 |
| Gln | Gly | Asp | Asp | Trp | Glu | Pro | Arg | Pro | Leu | Arg | Ala | Ala | Ser | Pro | Phe |     |
|     |     |     | 355 |     |     |     |     | 360 |     |     |     |     | 365 |     |     |     |
| agg | tca | tct | gtc | cag | ggt | gca | tcg | agc | cgg | gag | ggc | tca | cca | gcc | agg | 1152 |
| Arg | Ser | Ser | Val | Gln | Gly | Ala | Ser | Ser | Arg | Glu | Gly | Ser | Pro | Ala | Arg |     |
|     | 370 |     |     |     |     | 375 |     |     |     |     | 380 |     |     |     |     |     |
| agc | agc | acg | cca | ctc | cac | tcc | ccc | tcg | ccc | atc | cgt | gtg | cac | acc | gtg | 1200 |
| Ser | Ser | Thr | Pro | Leu | His | Ser | Pro | Ser | Pro | Ile | Arg | Val | His | Thr | Val |     |
| 385 |     |     |     |     | 390 |     |     |     |     | 395 |     |     |     |     | 400 |     |
| gtc | gac | agg | cct | cag | cag | ccc | atg | acc | cat | cga | gaa | act | gca | cct | gtt | 1248 |
| Val | Asp | Arg | Pro | Gln | Gln | Pro | Met | Thr | His | Arg | Glu | Thr | Ala | Pro | Val |     |
|     |     |     | 405 |     |     |     |     | 410 |     |     |     |     | 415 |     |     |     |
| tcc | cag | cct | gaa | aac | aaa | cca | gaa | agt | aag | cca | ggc | cca | gtt | gga | cca | 1296 |
| Ser | Gln | Pro | Glu | Asn | Lys | Pro | Glu | Ser | Lys | Pro | Gly | Pro | Val | Gly | Pro |     |
|     |     |     | 420 |     |     |     |     | 425 |     |     |     |     | 430 |     |     |     |
| gaa | ctc | cct | cct | gga | cac | atc | cca | att | caa | gtg | atc | cgc | aaa | gag | gtg | 1344 |
| Glu | Leu | Pro | Pro | Gly | His | Ile | Pro | Ile | Gln | Val | Ile | Arg | Lys | Glu | Val |     |
|     |     | 435 |     |     |     |     | 440 |     |     |     |     | 445 |     |     |     |     |
| gat | tct | aaa | cct | gtt | tcc | cag | aag | ccc | cca | cct | ccc | tct | gag | aag | gta | 1392 |
| Asp | Ser | Lys | Pro | Val | Ser | Gln | Lys | Pro | Pro | Pro | Pro | Ser | Glu | Lys | Val |     |
|     |     | 450 |     |     |     |     | 455 |     |     |     |     | 460 |     |     |     |     |
| gag | gtg | aaa | gtt | ccc | cct | gct | cca | gtt | cct | tgt | cct | cct | ccc | agc | cct | 1440 |
| Glu | Val | Lys | Val | Pro | Pro | Ala | Pro | Val | Pro | Cys | Pro | Pro | Pro | Ser | Pro |     |
| 465 |     |     |     |     | 470 |     |     |     |     | 475 |     |     |     |     | 480 |     |
| ggc | cct | tct | gct | gtc | ccc | tct | tcc | ccc | aag | agt | gtg | gct | aca | gaa | gag | 1488 |
| Gly | Pro | Ser | Ala | Val | Pro | Ser | Ser | Pro | Lys | Ser | Val | Ala | Thr | Glu | Glu |     |
|     |     |     |     | 485 |     |     |     |     | 490 |     |     |     |     | 495 |     |     |
| agg | gca | gcc | ccc | agc | act | gcc | cct | gca | gaa | gct | aca | cct | cca | aaa | cca | 1536 |
| Arg | Ala | Ala | Pro | Ser | Thr | Ala | Pro | Ala | Glu | Ala | Thr | Pro | Pro | Lys | Pro |     |
|     |     |     | 500 |     |     |     |     | 505 |     |     |     |     | 510 |     |     |     |
| gga | gaa | gcc | gag | gct | ccc | cca | aaa | cat | cca | gga | gtg | ctg | aaa | gtg | gaa | 1584 |
| Gly | Glu | Ala | Glu | Ala | Pro | Pro | Lys | His | Pro | Gly | Val | Leu | Lys | Val | Glu |     |
|     |     | 515 |     |     |     |     | 520 |     |     |     |     | 525 |     |     |     |     |
| gcc | atc | ctg | gag | aag | gtg | cag | ggg | ctg | gag | cag | gct | gta | gac | aac | ttt | 1632 |
| Ala | Ile | Leu | Glu | Lys | Val | Gln | Gly | Leu | Glu | Gln | Ala | Val | Asp | Asn | Phe |     |
| 530 |     |     |     |     | 535 |     |     |     |     | 540 |     |     |     |     |     |     |
| gaa | ggc | aag | aag | act | gac | aaa | aag | tac | ctg | atg | atc | gaa | gag | tat | ttg | 1680 |
| Glu | Gly | Lys | Lys | Thr | Asp | Lys | Lys | Tyr | Leu | Met | Ile | Glu | Glu | Tyr | Leu |     |
| 545 |     |     |     |     | 550 |     |     |     |     | 555 |     |     |     |     | 560 |     |
| acc | aaa | gag | ctg | ctg | gcc | ctg | gat | tca | gtg | gac | ccc | gag | gga | cga | gca | 1728 |
| Thr | Lys | Glu | Leu | Leu | Ala | Leu | Asp | Ser | Val | Asp | Pro | Glu | Gly | Arg | Ala |     |
|     |     | 565 |     |     |     |     | 570 |     |     |     |     | 575 |     |     |     |     |
| gat | gtg | cgt | cag | gcc | agg | aga | gac | ggt | gtc | agg | aag | gtt | cag | acc | atc | 1776 |
| Asp | Val | Arg | Gln | Ala | Arg | Arg | Asp | Gly | Val | Arg | Lys | Val | Gln | Thr | Ile |     |
|     |     |     | 580 |     |     |     |     | 585 |     |     |     |     | 590 |     |     |     |
| ttg | gaa | aaa | ctt | gaa | cag | aaa | gcc | att | gat | gtc | cca | ggt | caa | gtc | cag | 1824 |
| Leu | Glu | Lys | Leu | Glu | Gln | Lys | Ala | Ile | Asp | Val | Pro | Gly | Gln | Val | Gln |     |
|     |     | 595 |     |     |     |     | 600 |     |     |     |     | 605 |     |     |     |     |
| gtc | tat | gaa | ctc | cag | ccc | agc | aac | ctt | gaa | gca | gat | cag | cca | ctg | cag | 1872 |
| Val | Tyr | Glu | Leu | Gln | Pro | Ser | Asn | Leu | Glu | Ala | Asp | Gln | Pro | Leu | Gln |     |
|     | 610 |     |     |     |     | 615 |     |     |     |     | 620 |     |     |     |     |     |
| gca | atc | atg | gag | atg | ggt | gcc | gtg | gca | gca | gac | aag | ggc | aag | aaa | aat | 1920 |
| Ala | Ile | Met | Glu | Met | Gly | Ala | Val | Ala | Ala | Asp | Lys | Gly | Lys | Lys | Asn |     |
| 625 |     |     |     |     | 630 |     |     |     |     | 635 |     |     |     |     | 640 |     |
| gct | gga | aat | gca | gaa | gat | ccc | cac | aca | gaa | acc | cag | cag | cca | gaa | gcc | 1968 |
| Ala | Gly | Asn | Ala | Glu | Asp | Pro | His | Thr | Glu | Thr | Gln | Gln | Pro | Glu | Ala |     |
|     |     |     | 645 |     |     |     |     | 650 |     |     |     |     | 655 |     |     |     |
| aca | gca | gca | gcg | act | tca | aac | ccc | agc | agc | atg | aca | gac | acc | cct | ggt | 2016 |
| Thr | Ala | Ala | Ala | Thr | Ser | Asn | Pro | Ser | Ser | Met | Thr | Asp | Thr | Pro | Gly |     |
|     |     |     |     | 660 |     |     |     |     | 665 |     |     |     |     | 670 |     |     |
| aac | cca | gca | gca | ccg | tagcctctgc cctgtaaaag tcagactcgg aaccgatgtg | 2071 |
| Asn | Pro | Ala | Ala | Pro |     |

```
                                   675
    tgctttaggg attttagttg catgcatttc agagacttta ggtcagttgg ttttgattag  2131
    ctgcttggta tgcagtactt gggtgaggca aacactataa agggctaaaa gggaaaatga  2191
    tgcttttctt caatattctt actcttgtac aattaangaa gttgcttgtt gtttgagaag  2251
    tttaaccccg ttgcttgttc tgcagccctg tcnacttggg cacccccacc acctgttagc  2311
    tgtggttgtg cactgtcttt tgtagctctg gactggaggg gtagatgggg agtcaattac  2371
    ccatcacata aatatgaaac atttatcaga aatgttgcca ttttaatgag atgatttct   2431
    tcatctcata attaaaatac ctgactttag agagagtaaa aatgtgccagg agccatagga 2491
    atatctgtat gttggatgac tttaatgcta cattttth                         2528
```

<210> SEQ ID NO 6
<211> LENGTH: 677
<212> TYPE: PRT
<213> ORGANISM: Homo sapiens

<400> SEQUENCE: 6

```
Ala Glu Leu Arg Ile Gln Pro Arg Ala Ala Asn Phe Ser Gly Leu
 1               5                  10                  15
Asp Gln Lys Phe Leu Ala Gly Gln Leu Leu Pro Phe Ile Ser Ser
                20                  25                  30
Phe Pro Ser Gly Ser Glu Glu Ala Ile Ser Arg His Phe His Pro Ser
            35                  40                  45
Leu Ala Thr Ser Pro Pro Leu Ile His Lys Gly Ala Arg Arg Arg
        50                  55                  60
Leu Pro Gly His Val Gly Gly Glu Gly Pro Thr Ala Ala Arg
 65                 70                  75                  80
Pro Glu Thr Arg Arg Pro Glu Pro Ala Pro Arg Thr Arg Ala Pro Ala
                85                  90                  95
Gly Arg Pro Gln Pro Ser Met Ser Ala Ala Thr His Ser Pro Met Met
            100                 105                 110
Gln Val Ala Ser Gly Asn Gly Asp Arg Asp Pro Leu Pro Pro Gly Trp
        115                 120                 125
Glu Ile Lys Ile Asp Pro Gln Thr Gly Trp Pro Phe Phe Val Asp His
    130                 135                 140
Asn Ser Arg Thr Thr Thr Trp Asn Asp Pro Arg Val Pro Ser Glu Gly
145                 150                 155                 160
Pro Lys Glu Thr Pro Ser Ser Ala Asn Gly Pro Ser Arg Glu Gly Ser
                165                 170                 175
Arg Leu Pro Pro Ala Arg Glu Gly His Pro Val Tyr Pro Gln Leu Arg
            180                 185                 190
Pro Gly Tyr Ile Pro Ile Pro Val Leu His Glu Gly Ala Glu Asn Arg
        195                 200                 205
Gln Val His Pro Phe His Val Tyr Pro Gln Pro Gly Met Gln Arg Phe
    210                 215                 220
Arg Thr Glu Ala Ala Ala Ala Pro Gln Arg Ser Gln Ser Pro Leu
225                 230                 235                 240
Arg Gly Met Pro Glu Thr Thr Gln Pro Asp Lys Gln Cys Gly Gln Val
                245                 250                 255
Ala Ala Ala Ala Ala Gln Pro Pro Ala Ser His Gly Pro Glu Arg
            260                 265                 270
Ser Gln Ser Pro Ala Ala Ser Asp Cys Ser Ser Ser Ser Ser Ala
        275                 280                 285
Ser Leu Pro Ser Ser Gly Arg Ser Ser Leu Gly Ser His Gln Leu Pro
    290                 295                 300
Arg Gly Tyr Ile Ser Ile Pro Val Ile His Glu Gln Asn Val Thr Arg
305                 310                 315                 320
Pro Ala Ala Gln Pro Ser Phe His Lys Ala Gln Lys Thr His Tyr Pro
                325                 330                 335
Ala Gln Arg Gly Glu Tyr Gln Thr His His Gln Pro Val Tyr His Lys Ile
            340                 345                 350
Gln Gly Asp Asp Trp Glu Pro Arg Pro Leu Arg Ala Ser Pro Phe
        355                 360                 365
Arg Ser Ser Val Gln Gly Ala Ser Ser Arg Glu Gly Ser Pro Ala Arg
    370                 375                 380
Ser Ser Thr Pro Leu His Ser Pro Ser Pro Ile Arg Val His Thr Val
385                 390                 395                 400
Val Asp Arg Pro Gln Gln Pro Met Thr His Arg Glu Thr Ala Pro Val
                405                 410                 415
Ser Gln Pro Glu Asn Lys Pro Glu Ser Lys Pro Gly Pro Val Gly Pro
            420                 425                 430
Glu Leu Pro Pro Gly His Ile Pro Ile Gln Val Ile Arg Lys Glu Val
        435                 440                 445
Asp Ser Lys Pro Val Ser Gln Lys Pro Pro Pro Ser Glu Lys Val
    450                 455                 460
Glu Val Lys Val Pro Pro Ala Pro Val Pro Cys Pro Pro Ser Pro
465                 470                 475                 480
Gly Pro Ser Ala Val Pro Ser Ser Pro Lys Ser Val Ala Thr Glu Glu
```

```
            485                 490                 495
    Arg Ala Ala Pro Ser Thr Ala Pro Ala Glu Ala Thr Pro Pro Lys Pro
            500                 505                 510
    Gly Glu Ala Glu Ala Pro Pro Lys His Pro Gly Val Leu Lys Val Glu
            515                 520                 525
    Ala Ile Leu Glu Lys Val Gln Gly Leu Glu Gln Ala Val Asp Asn Phe
            530                 535                 540
    Glu Gly Lys Lys Thr Asp Lys Lys Tyr Leu Met Ile Glu Glu Tyr Leu
545                 550                 555                 560
    Thr Lys Glu Leu Leu Ala Leu Asp Ser Val Asp Pro Glu Gly Arg Ala
                565                 570                 575
    Asp Val Arg Gln Ala Arg Arg Asp Gly Val Arg Lys Val Gln Thr Ile
            580                 585                 590
    Leu Glu Lys Leu Glu Gln Lys Ala Ile Asp Val Pro Gly Gln Val Gln
            595                 600                 605
    Val Tyr Glu Leu Gln Pro Ser Asn Leu Glu Ala Asp Gln Pro Leu Gln
            610                 615                 620
    Ala Ile Met Glu Met Gly Ala Val Ala Ala Asp Lys Gly Lys Lys Asn
625                 630                 635                 640
    Ala Gly Asn Ala Glu Asp Pro His Thr Glu Thr Gln Gln Pro Glu Ala
                645                 650                 655
    Thr Ala Ala Ala Thr Ser Asn Pro Ser Ser Met Thr Asp Thr Pro Gly
                660                 665                 670
    Asn Pro Ala Ala Pro
                675

<210> SEQ ID NO 7
<211> LENGTH: 1010
<212> TYPE: DNA
<213> ORGANISM: Homo sapiens
<220> FEATURE:
<221> NAME/KEY: CDS
<222> LOCATION: (323)..(1009)

<400> SEQUENCE: 7
acgatatcct gtaagaccaa gaattgcaag gccagagttt gaattcttat acaaatggag    60
    cgtatggtcc aacataccce ccaggccctg gggcaaatac tgcctcatac tcaggggctt   120
    attatgcacc tggttatact cagaccagtt actccacaga agttccaagt acttaccgtt   180
    catctggcaa cagcccaact ccagtctctc gttggatcta tccccagcag gactgtcaag   240
    actgaagcac ccctcttaa ggggcaggtt ccaggatatc cgccttcaca gaaccctgga   300
    atgaccctgc cccattatcc tt atg gag atg gta atc gta gtg ttc cac aat   352
                             Met Glu Met Val Ile Val Val Phe His Asn
                              1               5                  10
    cac ggc cga ctg tac gac cac aag aaa gat gcg tgg gct tct cct ggt    400
    His Gly Arg Leu Tyr Asp His Lys Lys Asp Ala Trp Ala Ser Pro Gly
                    15                  20                  25
    gct tat gga atg ggt ggc cgt tat ccc tgg cct tca tca gcg ccc tca    448
    Ala Tyr Gly Met Gly Gly Arg Tyr Pro Trp Pro Ser Ser Ala Pro Ser
            30                  35                  40
    gca cca ccc ggc aat ctc tac atg act gaa agt act tca cca tgg cct    496
    Ala Pro Pro Gly Asn Leu Tyr Met Thr Glu Ser Thr Ser Pro Trp Pro
        45                  50                  55
    agc agt ggt tct ccc cag tca ccc cct tca ccc cca gtc cag cag ccc    544
    Ser Ser Gly Ser Pro Gln Ser Pro Pro Ser Pro Pro Val Gln Gln Pro
    60                  65                  70
    aag gat tct tca tac ccc tat agc caa tca gat caa agc atg aac cgg    592
    Lys Asp Ser Ser Tyr Pro Tyr Ser Gln Ser Asp Gln Ser Met Asn Arg
75                  80                  85                  90
    cac aac ttt cct tgc agt gtc cat cag tac gaa tcc tcg ggg aca gtg    640
    His Asn Phe Pro Cys Ser Val His Gln Tyr Glu Ser Ser Gly Thr Val
                    95                 100                 105
    aac aat gat gat tca gat ctt ttg gat tcc caa gtc cag tat agt gct    688
    Asn Asn Asp Asp Ser Asp Leu Leu Asp Ser Gln Val Gln Tyr Ser Ala
                110                 115                 120
    gag cct cag ctg tat ggt aat gcc acc agt gac cat ccc aac aat caa    736
    Glu Pro Gln Leu Tyr Gly Asn Ala Thr Ser Asp His Pro Asn Asn Gln
            125                 130                 135
    gat caa agt agc agt ctt cct gaa gaa tgt gta cct tca gat gaa agt    784
    Asp Gln Ser Ser Ser Leu Pro Glu Glu Cys Val Pro Ser Asp Glu Ser
        140                 145                 150
    act cct ccg agt att aaa aaa atc ata cat gtg ctg gag aag gtc cag    832
    Thr Pro Pro Ser Ile Lys Lys Ile Ile His Val Leu Glu Lys Val Gln
    155                 160                 165                 170
    tat ctt gaa caa gaa gta gaa gaa ttt gta gga aaa aag aca gac aaa    880
    Tyr Leu Glu Gln Glu Val Glu Glu Phe Val Gly Lys Lys Thr Asp Lys
                    175                 180                 185
    gca tac tgg ctt ctg gaa gaa atg cta acc aag gaa ctt ttg gaa ctg    928
```

```
              Ala Tyr Trp Leu Leu Glu Glu Met Leu Thr Lys Glu Leu Leu Glu Leu
                      190                 195                 200
              gat tca gtt gaa act ggg ggc cag gac tct gta cgg cag gcc aga aaa        976
              Asp Ser Val Glu Thr Gly Gly Gln Asp Ser Val Arg Gln Ala Arg Lys
                      205                 210                 215
              gag gct gtt tgt aag att cag gcc ata ttg gaa a                         1010
              Glu Ala Val Cys Lys Ile Gln Ala Ile Leu Glu
                      220                 225

<210> SEQ ID NO 8
<211> LENGTH: 229
<212> TYPE: PRT
<213> ORGANISM: Homo sapiens

<400> SEQUENCE: 8

Met Glu Met Val Ile Val Val Phe His Asn His Gly Arg Leu Tyr Asp
       1               5                  10                  15
      His Lys Lys Asp Ala Trp Ala Ser Pro Gly Ala Tyr Gly Met Gly Gly
                      20                  25                  30
      Arg Tyr Pro Trp Pro Ser Ser Ala Pro Ser Ala Pro Pro Gly Asn Leu
                      35                  40                  45
      Tyr Met Thr Glu Ser Thr Ser Pro Trp Pro Ser Ser Gly Ser Pro Gln
              50                  55                  60
      Ser Pro Pro Ser Pro Val Gln Gln Pro Lys Asp Ser Ser Tyr Pro
       65                  70                  75                  80
      Tyr Ser Gln Ser Asp Gln Ser Met Asn Arg His Asn Phe Pro Cys Ser
                      85                  90                  95
      Val His Gln Tyr Glu Ser Ser Gly Thr Val Asn Asn Asp Ser Asp
                      100                 105                 110
      Leu Leu Asp Ser Gln Val Gln Tyr Ser Ala Glu Pro Gln Leu Tyr Gly
                      115                 120                 125
      Asn Ala Thr Ser Asp His Pro Asn Asn Gln Asp Gln Ser Ser Ser Leu
                      130                 135                 140
      Pro Glu Glu Cys Val Pro Ser Asp Gly Ser Thr Pro Pro Ser Ile Lys
      145                 150                 155                 160
      Lys Ile Ile His Val Leu Glu Lys Val Gln Tyr Leu Glu Gln Glu Val
                      165                 170                 175
      Glu Glu Phe Val Gly Lys Lys Thr Asp Lys Ala Tyr Trp Leu Leu Glu
                      180                 185                 190
      Glu Met Leu Thr Lys Glu Leu Leu Glu Leu Asp Ser Val Glu Thr Gly
                      195                 200                 205
      Gly Gln Asp Ser Val Arg Gln Ala Arg Lys Glu Ala Val Cys Lys Ile
                      210                 215                 220
      Gln Ala Ile Leu Glu
      225

<210> SEQ ID NO 9
<211> LENGTH: 689
<212> TYPE: DNA
<213> ORGANISM: Homo sapiens
<220> FEATURE:
<221> NAME/KEY: CDS
<222> LOCATION: (3)..(482)
<221> NAME/KEY: unsure
<222> LOCATION: (105)
<223> OTHER INFORMATION: any amino acid
<221> NAME/KEY: misc_feature
<222> LOCATION: (1)..(659)
<223> OTHER INFORMATION: n= a, c, to or g

<400> SEQUENCE: 9 ga gaa ata aaa aat gaa ctt ctc caa gca caa aac cct tct gaa ttg          47
         Glu Ile Lys Asn Glu Leu Leu Gln Ala Gln Asn Pro Ser Glu Leu
          1               5                  10                  15
      tac ctg agc tcc aaa aca gaa ttg cag ggt tta att gga cag ttg gat        95
      Tyr Leu Ser Ser Lys Thr Glu Leu Gln Gly Leu Ile Gly Gln Leu Asp
                      20                  25                  30
      gag gta agt ntt gaa aaa aac ccc tgc atc cgg gaa gcc agg aga aga       143
      Glu Val Ser Xaa Glu Lys Asn Pro Cys Ile Arg Glu Ala Arg Arg Arg
                      35                  40                  45
      gca gtg atc gag gtg caa act ctg atc aca tat att gac ttg aag gag       191
      Ala Val Ile Glu Val Gln Thr Leu Ile Thr Tyr Ile Asp Leu Lys Glu
              50                  55                  60
      gcc ctt gag aaa aga aag ctg ttt gct tgt gag gag cac cca tcc cat       239
      Ala Leu Glu Lys Arg Lys Leu Phe Ala Cys Glu Glu His Pro Ser His
```

```
                65                  70                  75
    aaa gcc gtc tgg aac gtc ctt gga aac ttg tct gag atc cag gga gaa    287
    Lys Ala Val Trp Asn Val Leu Gly Asn Leu Ser Glu Ile Gln Gly Glu
         80                  85                  90                  95
    gtt ctt tca ttt gat gga aat cga acc gat aag aac tac atc cgg ctg    335
    Val Leu Ser Phe Asp Gly Asn Arg Thr Asp Lys Asn Tyr Ile Arg Leu
                    100                 105                 110
    gaa gag ctg ctc acc aag cag ctg cta gcc ctg gat gct gtt gat ccg    383
    Glu Glu Leu Leu Thr Lys Gln Leu Leu Ala Leu Asp Ala Val Asp Pro
                115                 120                 125
    cag gga gaa gag aag tgt aag gct gcc agg aaa caa gct gtg agg ctt    431
    Gln Gly Glu Glu Lys Cys Lys Ala Ala Arg Lys Gln Ala Val Arg Leu
            130                 135                 140
    gcg cag aat att ctc agc tat ctc gac ctg aaa tct gat gaa tgg gag    479
    Ala Gln Asn Ile Leu Ser Tyr Leu Asp Leu Lys Ser Asp Glu Trp Glu
        145                 150                 155
    tac tgaaatacca gagatctcac ttttgatact gttttgcact tcatatgtgc         532
    Tyr
    160
    ttctatgtat agagagcttt cagttcattg atttatacgt gcatatttca gtctcagtat  592
    ttatgattga agcaaattct attcagtatc tgctgctttt gatgttgcaa gacaaatatc  652
    attacagcac gttaactttt ccattcggat caaaaaa                           689
```

<210> SEQ ID NO 10
<211> LENGTH: 160
<212> TYPE: PRT
<213> ORGANISM: Homo sapiens
<220> FEATURE:
<221> NAME/KEY: unsure
<222> LOCATION: 1..160
<223> OTHER INFORMATION: Xaa=any amino acid

<400> SEQUENCE: 10

```
    Glu Ile Lys Asn Glu Leu Leu Gln Ala Gln Asn Pro Ser Glu Leu Tyr
    1               5                   10                  15
    Leu Ser Ser Lys Thr Glu Leu Gln Gly Leu Ile Gly Gln Leu Asp Glu
                20                  25                  30
    Val Ser Xaa Glu Lys Asn Pro Cys Ile Arg Glu Ala Arg Arg Ala
                35                  40                  45
    Val Ile Glu Val Gln Thr Leu Ile Thr Tyr Ile Asp Leu Lys Glu Ala
        50                  55                  60
    Leu Glu Lys Arg Lys Leu Phe Ala Cys Glu Glu His Pro Ser His Lys
    65                  70                  75                  80
    Ala Val Trp Asn Val Leu Gly Asn Leu Ser Glu Ile Gln Gly Glu Val
                    85                  90                  95
    Leu Ser Phe Asp Gly Asn Arg Thr Asp Lys Asn Tyr Ile Arg Leu Glu
                100                 105                 110
    Glu Leu Leu Thr Lys Gln Leu Leu Ala Leu Asp Ala Val Asp Pro Gln
            115                 120                 125
    Gly Glu Glu Lys Cys Lys Ala Ala Arg Lys Gln Ala Val Arg Leu Ala
        130                 135                 140
    Gln Asn Ile Leu Ser Tyr Leu Asp Leu Lys Ser Asp Glu Trp Glu Tyr
    145                 150                 155                 160
```

<210> SEQ ID NO 11
<211> LENGTH: 246
<212> TYPE: DNA
<213> ORGANISM: Caenorhabditis elegans

<400> SEQUENCE: 11

```
    atgtctttcc gcctcttcgt tgaaatattt cactttcttt tccagctttt tccccatctc   60
    gacctgcttt ggttttttcga gaaaaccacg ttccaaatca gcgacatctc tcaaattgag  120
    atcataggct ttttgaagat tgctcaaatt atgcttctca tattgcatga gcattttgaa  180
    gcccgcgtca tcaaccaaag cattttttcc acccatcaca atgatttat cattttcttt   240
    aaaatt                                                              246
```

<210> SEQ ID NO 12
<211> LENGTH: 210
<212> TYPE: PRT
<213> ORGANISM: Caenorhabditis elegans

<400> SEQUENCE: 12

```
    Met Lys Val Asn Val Ser Cys Ser Ser Val Gln Thr Thr Ile Asp Ile
```

```
          1               5                   10                  15
        Leu Glu Glu Asn Gln Gly Glu Asp Glu Ser Ile Leu Thr Leu Gly Gln
                        20                  25                  30
        Leu Arg Asp Arg Ile Ala Thr Asp Asn Asp Val Asp Val Glu Thr Met
                    35                  40                  45
        Lys Leu Leu His Arg Gly Lys Phe Leu Gln Gly Ala Asp Asp Val Ser
                50                  55                  60
        Leu Ser Thr Leu Asn Phe Lys Glu Asn Asp Lys Ile Ile Val Met Gly
            65                  70                  75                  80
        Gly Lys Asn Ala Leu Val Asp Asp Ala Gly Phe Lys Met Leu Met Gln
                        85                  90                  95
        Tyr Glu Lys His Asn Leu Ser Asn Leu Gln Lys Ala Tyr Asp Leu Asn
                        100                 105                 110
        Leu Arg Asp Val Ala Asp Leu Glu Arg Gly Phe Leu Glu Lys Pro Lys
                    115                 120                 125
        Gln Val Glu Met Gly Lys Lys Leu Glu Lys Lys Val Lys Tyr Phe Asn
                    130                 135                 140
        Glu Glu Ala Glu Arg His Leu Glu Thr Leu Asp Gly Met Asn Ile Ile
            145                 150                 155                 160
        Thr Glu Thr Thr Pro Glu Asn Gln Ala Lys Arg Asn Arg Glu Lys Arg
                        165                 170                 175
        Lys Thr Leu Val Asn Gly Ile Gln Thr Leu Leu Asn Gln Asn Asp Ala
                        180                 185                 190
        Leu Leu Arg Arg Leu Gln Glu Tyr Gln Ser Val Leu Asn Gly Asp Ile
                    195                 200                 205
        Pro Glu
            210

<210> SEQ ID NO 13
<211> LENGTH: 1377
<212> TYPE: DNA
<213> ORGANISM: Caenorhabditis elegans
<220> FEATURE:
<221> NAME/KEY: CDS
<222> LOCATION: (1)..(1377)

<400> SEQUENCE: 13 atg cca gtc gtg aac ata cca atc aaa ata ctt ggt cag aat caa tca      48
        Met Pro Val Val Asn Ile Pro Ile Lys Ile Leu Gly Gln Asn Gln Ser
          1               5                   10                  15
        cat agt cga agt aac tcc tcg tct tct gtt gac aac gat cga aat caa      96
        His Ser Arg Ser Asn Ser Ser Ser Ser Val Asp Asn Asp Arg Asn Gln
                        20                  25                  30
        cca cca cag cag cca cct caa ccg caa cca caa cag caa tct cag caa     144
        Pro Pro Gln Gln Pro Pro Gln Pro Gln Pro Gln Gln Gln Ser Gln Gln
                    35                  40                  45
        caa tac cag cag gct cca aac gtg aat acc aat atg cat cat tcc aac     192
        Gln Tyr Gln Gln Ala Pro Asn Val Asn Thr Asn Met His His Ser Asn
                50                  55                  60
        gga ttc tca cct aac ttc cca tct cgt agt cct att ccg gac ttt ccc     240
        Gly Phe Ser Pro Asn Phe Pro Ser Arg Ser Pro Ile Pro Asp Phe Pro
            65                  70                  75                  80
        agt ttt tca tct ggg ttc cca aac gat tct gaa tgg tct tcg aat ttc     288
        Ser Phe Ser Ser Gly Phe Pro Asn Asp Ser Glu Trp Ser Ser Asn Phe
                        85                  90                  95
        ccg tcg ttt cca aat ttc cca agt gga ttc tca aat gga agt tct aat     336
        Pro Ser Phe Pro Asn Phe Pro Ser Gly Phe Ser Asn Gly Ser Ser Asn
                        100                 105                 110
        ttc cct gat ttt cca aga ttc gga aga gat gga gga cta tcg cca aac     384
        Phe Pro Asp Phe Pro Arg Phe Gly Arg Asp Gly Gly Leu Ser Pro Asn
                    115                 120                 125
        cca ccg atg caa gga tac agg aga agt cca aca cca aca tca act caa     432
        Pro Pro Met Gln Gly Tyr Arg Arg Ser Pro Thr Pro Thr Ser Thr Gln
                    130                 135                 140
        tct cca act tct aca tta aga cgc aac tct cag cag aat caa gct cct     480
        Ser Pro Thr Ser Thr Leu Arg Arg Asn Ser Gln Gln Asn Gln Ala Pro
        145                 150                 155                 160
        cca caa tat tct cag caa caa cca caa caa gct caa caa cgt cag aca     528
        Pro Gln Tyr Ser Gln Gln Gln Pro Gln Gln Ala Gln Gln Arg Gln Thr
                        165                 170                 175
        act cct ccg tca aca aaa gct tca tct cga cca cca tct cgt act cgt     576
        Thr Pro Pro Ser Thr Lys Ala Ser Ser Arg Pro Pro Ser Arg Thr Arg
                        180                 185                 190
        gaa cca aag gaa cct gag gta ccc gag aga cca gca gtt att cca ttg     624
        Glu Pro Lys Glu Pro Glu Val Pro Glu Arg Pro Ala Val Ile Pro Leu
                    195                 200                 205
        cca tat gag aag aag gag aaa cca ctg gag aag aaa ggt agt cgt gat     672
```

|     |     |     |     |     |     |     |     |     |     |     |     |      |
| --- | --- | --- | --- | --- | --- | --- | --- | --- | --- | --- | --- | ---- |
| Pro | Tyr | Glu | Lys | Lys | Glu | Lys | Pro | Leu | Glu | Lys | Lys | Gly Arg Asp |
|     | 210 |     |     |     | 215 |     |     |     |     | 220 |     |      |

```
tct gga aag ggt gat gag aac ctt gaa gag aac att gcc aag atc acg   720
Ser Gly Lys Gly Asp Glu Asn Leu Glu Glu Asn Ile Ala Lys Ile Thr
225                 230                 235                 240
atc gga aag aat aat tgc gag tta tgt ccg gaa caa gaa acg gac ggc   768
Ile Gly Lys Asn Asn Cys Glu Leu Cys Pro Glu Gln Glu Thr Asp Gly
                245                 250                 255
gac cca tct cca cta acc tcc cca atc acc gaa gga aag cca aag aga   816
Asp Pro Ser Pro Leu Thr Ser Pro Ile Thr Glu Gly Lys Pro Lys Arg
            260                 265                 270
gga aag aaa ctt caa cgt aat caa agt gtt gtt gat ttc aat gcc aag   864
Gly Lys Lys Leu Gln Arg Asn Gln Ser Val Val Asp Phe Asn Ala Lys
        275                 280                 285
aca att gtt act ttg gat aaa att gaa tta caa gtt gag cag ttg aga   912
Thr Ile Val Thr Leu Asp Lys Ile Glu Leu Gln Val Glu Gln Leu Arg
    290                 295                 300
aaa aaa gct gct gaa ctc gaa atg gaa aaa gag caa att ctt cgt tct   960
Lys Lys Ala Ala Glu Leu Glu Met Glu Lys Glu Gln Ile Leu Arg Ser
305                 310                 315                 320
cta gga gaa atc agt gtt cat aac tgc atg ttc aaa ctg gaa gaa tgt  1008
Leu Gly Glu Ile Ser Val His Asn Cys Met Phe Lys Leu Glu Glu Cys
                325                 330                 335
gat cgt gaa gag att gaa gca atc act gac cga ttg aca aaa aga aca  1056
Asp Arg Glu Glu Ile Glu Ala Ile Thr Asp Arg Leu Thr Lys Arg Thr
            340                 345                 350
aag aca gtt caa gtt gtt gtc gaa act cca cga aat gaa gaa cag aaa  1104
Lys Thr Val Gln Val Val Val Glu Thr Pro Arg Asn Glu Glu Gln Lys
        355                 360                 365
aaa gca ctg gaa gat gca act ttg atg atc gat gaa gtc gga gaa atg  1152
Lys Ala Leu Glu Asp Ala Thr Leu Met Ile Asp Glu Val Gly Glu Met
    370                 375                 380
atg cat tcg aat att gaa aag gct aag ctg tgc cta caa acc tac atg  1200
Met His Ser Asn Ile Glu Lys Ala Lys Leu Cys Leu Gln Thr Tyr Met
385                 390                 395                 400
aac gcc tgt tcg tac gaa gaa act gct gga gcc acc tgc caa aac ttc  1248
Asn Ala Cys Ser Tyr Glu Glu Thr Ala Gly Ala Thr Cys Gln Asn Phe
                405                 410                 415
ttg aag atc ata att cag tgc gct gct gat gat cag aaa cgc atc aag  1296
Leu Lys Ile Ile Ile Gln Cys Ala Ala Asp Asp Gln Lys Arg Ile Lys
            420                 425                 430
cgt cgt ctg gaa aat ctg atg tct caa att gag aat gct gag aga acg  1344
Arg Arg Leu Glu Asn Leu Met Ser Gln Ile Glu Asn Ala Glu Arg Thr
        435                 440                 445
aaa gca gat ttg atg gat gat caa agc gaa tag                      1377
Lys Ala Asp Leu Met Asp Asp Gln Ser Glu
    450                 455
```

<210> SEQ ID NO 14
<211> LENGTH: 458
<212> TYPE: PRT
<213> ORGANISM: Caenorhabditis elegans

<400> SEQUENCE: 14

```
Met Pro Val Val Asn Ile Pro Ile Lys Ile Leu Gly Gln Asn Gln Ser
  1               5                  10                  15
His Ser Arg Ser Asn Ser Ser Ser Val Asp Asn Asp Arg Asn Gln
             20                  25                  30
Pro Pro Gln Pro Pro Gln Pro Gln Pro Gln Gln Gln Ser Gln Gln
         35                  40                  45
Gln Tyr Gln Gln Ala Pro Asn Val Asn Thr Asn Met His His Ser Asn
     50                  55                  60
Gly Phe Ser Pro Asn Phe Pro Ser Arg Ser Pro Ile Pro Asp Phe Pro
 65                  70                  75                  80
Ser Phe Ser Ser Gly Phe Pro Asn Asp Ser Glu Trp Ser Ser Asn Phe
                 85                  90                  95
Pro Ser Phe Pro Asn Phe Pro Ser Gly Phe Ser Asn Gly Ser Ser Asn
            100                 105                 110
Phe Pro Asp Phe Pro Arg Phe Gly Arg Asp Gly Leu Ser Pro Asn
        115                 120                 125
Pro Pro Met Gln Gly Tyr Arg Arg Ser Pro Thr Pro Thr Ser Thr Gln
    130                 135                 140
Ser Pro Thr Ser Thr Leu Arg Arg Asn Ser Gln Gln Asn Gln Ala Pro
145                 150                 155                 160
Pro Gln Tyr Ser Gln Gln Pro Gln Ala Gln Gln Arg Gln Thr
                165                 170                 175
Thr Pro Pro Ser Thr Lys Ala Ser Ser Arg Pro Pro Ser Arg Thr Arg
```

-continued

```
            180                 185                 190
    Glu Pro Lys Glu Pro Glu Val Pro Glu Arg Pro Ala Val Ile Pro Leu
        195                 200                 205
    Pro Tyr Glu Lys Lys Glu Lys Pro Leu Glu Lys Lys Gly Ser Arg Asp
    210                 215                 220
    Ser Gly Lys Gly Asp Glu Asn Leu Glu Glu Asn Ile Ala Lys Ile Thr
225                 230                 235                 240
    Ile Gly Lys Asn Asn Cys Glu Leu Cys Pro Glu Gln Glu Thr Asp Gly
                245                 250                 255
    Asp Pro Ser Pro Leu Thr Ser Pro Ile Thr Glu Gly Lys Pro Lys Arg
            260                 265                 270
    Gly Lys Lys Leu Gln Arg Asn Gln Ser Val Val Asp Phe Asn Ala Lys
        275                 280                 285
    Thr Ile Val Thr Leu Asp Lys Ile Glu Leu Gln Val Glu Gln Leu Arg
    290                 295                 300
    Lys Lys Ala Ala Glu Leu Glu Met Glu Lys Glu Gln Ile Leu Arg Ser
305                 310                 315                 320
    Leu Gly Glu Ile Ser Val His Asn Cys Met Phe Lys Leu Glu Glu Cys
                325                 330                 335
    Asp Arg Glu Glu Ile Glu Ala Ile Thr Asp Arg Leu Thr Lys Arg Thr
            340                 345                 350
    Lys Thr Val Gln Val Val Glu Thr Pro Arg Asn Glu Glu Gln Lys
        355                 360                 365
    Lys Ala Leu Glu Asp Ala Thr Leu Met Ile Asp Glu Val Gly Glu Met
    370                 375                 380
    Met His Ser Asn Ile Glu Lys Ala Lys Leu Cys Leu Gln Thr Tyr Met
385                 390                 395                 400
    Asn Ala Cys Ser Tyr Glu Glu Thr Ala Gly Ala Thr Cys Gln Asn Phe
                405                 410                 415
    Leu Lys Ile Ile Ile Gln Cys Ala Ala Asp Asp Gln Lys Arg Ile Lys
            420                 425                 430
    Arg Arg Leu Glu Asn Leu Met Ser Gln Ile Glu Asn Ala Glu Arg Thr
        435                 440                 445
    Lys Ala Asp Leu Met Asp Asp Gln Ser Glu
    450                 455
```

<210> SEQ ID NO 15
<211> LENGTH: 588
<212> TYPE: DNA
<213> ORGANISM: Schizosaccharomyces pombe
<220> FEATURE:
<221> NAME/KEY: CDS
<222> LOCATION: (1)..(588)

<400> SEQUENCE: 15

```
atg tca gaa aag act agc aca gtt aca ata cac tat gga aat cag cga    48
Met Ser Glu Lys Thr Ser Thr Val Thr Ile His Tyr Gly Asn Gln Arg
  1               5                  10                  15
ttt ccg gta gca gtc aat cta aat gag acg tta agt gaa ctg att gat    96
Phe Pro Val Ala Val Asn Leu Asn Glu Thr Leu Ser Glu Leu Ile Asp
             20                  25                  30
gat tta ctt gaa acg act gag att tct gag aag aaa gtc aag ctt ttt   144
Asp Leu Leu Glu Thr Thr Glu Ile Ser Glu Lys Lys Val Lys Leu Phe
         35                  40                  45
tac gct ggc aag cgt tta aaa gac aaa aaa gcc tcg tta tca aaa ttg   192
Tyr Ala Gly Lys Arg Leu Lys Asp Lys Lys Ala Ser Leu Ser Lys Leu
     50                  55                  60
ggt tta aaa aat cat agt aaa att cta tgt ata aga cca cat aag caa   240
Gly Leu Lys Asn His Ser Lys Ile Leu Cys Ile Arg Pro His Lys Gln
 65                  70                  75                  80
caa cga ggt tcc aag gaa aaa gac acg gtt gag ccc gct ccg aaa gcg   288
Gln Arg Gly Ser Lys Glu Lys Asp Thr Val Glu Pro Ala Pro Lys Ala
                 85                  90                  95
gaa gcg gag aat cct gta ttt tcg cgt att tct gga gaa ata aaa gcc   336
Glu Ala Glu Asn Pro Val Phe Ser Arg Ile Ser Gly Glu Ile Lys Ala
            100                 105                 110
atc gat cag tat gtt gac aaa gaa ctt tcc ccc atg tac gac aat tac   384
Ile Asp Gln Tyr Val Asp Lys Glu Leu Ser Pro Met Tyr Asp Asn Tyr
        115                 120                 125
gta aat aaa ccg tcg aac gat cca aag cag aaa aac aaa cag aaa cta   432
Val Asn Lys Pro Ser Asn Asp Pro Lys Gln Lys Asn Lys Gln Lys Leu
    130                 135                 140
atg ata agt gaa cta ctt tta caa cag ctt tta aaa ttg gat gga gtt   480
Met Ile Ser Glu Leu Leu Leu Gln Gln Leu Leu Lys Leu Asp Gly Val
145                 150                 155                 160
gac gta ctg ggc agc gag aaa ttg cgt ttt gaa cgg aag caa ctt gtt   528
Asp Val Leu Gly Ser Glu Lys Leu Arg Phe Glu Arg Lys Gln Leu Val
```

```
        165                 170                 175
tct aag atc caa aaa atg ttg gat cac gtt gac caa aca agc caa gaa    576
Ser Lys Ile Gln Lys Met Leu Asp His Val Asp Gln Thr Ser Gln Glu
            180                 185                 190
gtg gcc gca tag                                                    588
Val Ala Ala
        195

<210> SEQ ID NO 16
<211> LENGTH: 195
<212> TYPE: PRT
<213> ORGANISM: Schizosaccharomyces pombe

<400> SEQUENCE: 16

Met Ser Glu Lys Thr Ser Thr Val Thr Ile His Tyr Gly Asn Gln Arg
 1               5                  10                  15
Phe Pro Val Ala Val Asn Leu Asn Glu Thr Leu Ser Glu Leu Ile Asp
            20                  25                  30
Asp Leu Leu Glu Thr Thr Glu Ile Ser Glu Lys Lys Val Lys Leu Phe
        35                  40                  45
Tyr Ala Gly Lys Arg Leu Lys Asp Lys Lys Ala Ser Leu Ser Lys Leu
    50                  55                  60
Gly Leu Lys Asn His Ser Lys Ile Leu Cys Ile Arg Pro His Lys Gln
65                  70                  75                  80
Gln Arg Gly Ser Lys Glu Lys Asp Thr Val Glu Pro Ala Pro Lys Ala
                85                  90                  95
Glu Ala Glu Asn Pro Val Phe Ser Arg Ile Ser Gly Glu Ile Lys Ala
            100                 105                 110
Ile Asp Gln Tyr Val Asp Lys Glu Leu Ser Pro Met Tyr Asp Asn Tyr
        115                 120                 125
Val Asn Lys Pro Ser Asn Asp Pro Lys Gln Lys Asn Lys Gln Lys Leu
    130                 135                 140
Met Ile Ser Glu Leu Leu Leu Gln Gln Leu Leu Lys Leu Asp Gly Val
145                 150                 155                 160
Asp Val Leu Gly Ser Glu Lys Leu Arg Phe Glu Arg Lys Gln Leu Val
                165                 170                 175
Ser Lys Ile Gln Lys Met Leu Asp His Val Asp Gln Thr Ser Gln Glu
            180                 185                 190
Val Ala Ala
        195

<210> SEQ ID NO 17
<211> LENGTH: 621
<212> TYPE: DNA
<213> ORGANISM: Schizosaccharomyces pombe
<220> FEATURE:
<221> NAME/KEY: CDS
<222> LOCATION: (1)..(621)

<400> SEQUENCE: 17 atg tct ttt ttt acc cag ttg tgt tct atg gat aaa aaa tat tgg atc    48
Met Ser Phe Phe Thr Gln Leu Cys Ser Met Asp Lys Lys Tyr Trp Ile
 1               5                  10                  15
tct cta gct gta ttg tca gtt act gtt ttg att agc gca tta ttg aaa    96
Ser Leu Ala Val Leu Ser Val Thr Val Leu Ile Ser Ala Leu Leu Lys
            20                  25                  30
aag aga gct act gaa acc gaa gat att gtc gtt gtt cat tac gat ggc   144
Lys Arg Ala Thr Glu Thr Glu Asp Ile Val Val Val His Tyr Asp Gly
        35                  40                  45
gaa aag ttg aat ttt gtg ttg cga caa cca agg ctg aat atg gtt tct   192
Glu Lys Leu Asn Phe Val Leu Arg Gln Pro Arg Leu Asn Met Val Ser
    50                  55                  60
tac act agt ttt ctt cgt cgc gtg tgc aac gca ttt tca gta atg ccc   240
Tyr Thr Ser Phe Leu Arg Arg Val Cys Asn Ala Phe Ser Val Met Pro
65                  70                  75                  80
gac aaa gcg tct ctc aag tta aac ggg gtg acc ctc aag gat ggt tca   288
Asp Lys Ala Ser Leu Lys Leu Asn Gly Val Thr Leu Lys Asp Gly Ser
                85                  90                  95
ctt tcc gac caa aat gtg caa aat gga agt gaa tta gag ctc gaa tta   336
Leu Ser Asp Gln Asn Val Gln Asn Gly Ser Glu Leu Glu Leu Glu Leu
            100                 105                 110
ccc aaa ctg agc ccg gca atg caa caa att gaa gca tat ata gat gag   384
Pro Lys Leu Ser Pro Ala Met Gln Gln Ile Glu Ala Tyr Ile Asp Glu
        115                 120                 125
ctt caa cag gat ctc gtc cct aaa att gaa gcc ttc tgc caa tcg tct   432
```

```
        Leu Gln Gln Asp Leu Val Pro Lys Ile Glu Ala Phe Cys Gln Ser Ser
            130                 135                 140
        ccc gct tcg gca caa gat gtt caa gat ttg cat aca cgc ctt agt gaa     480
        Pro Ala Ser Ala Gln Asp Val Gln Asp Leu His Thr Arg Leu Ser Glu
        145                 150                 155                 160
        aca ttg ttg gct agg atg ata aaa tta gat gct gtt aat gtt gaa gac     528
        Thr Leu Leu Ala Arg Met Ile Lys Leu Asp Ala Val Asn Val Glu Asp
                        165                 170                 175
        gac cca gaa gct cgt ctt aaa aga aaa gaa gct att cgt tta tct caa     576
        Asp Pro Glu Ala Arg Leu Lys Arg Lys Glu Ala Ile Arg Leu Ser Gln
                    180                 185                 190
        caa tat ttg agt aaa cta gat tcc acc aag aat caa aac aaa tga         621
        Gln Tyr Leu Ser Lys Leu Asp Ser Thr Lys Asn Gln Asn Lys
                195                 200                 205
```

<210> SEQ ID NO 18
<211> LENGTH: 206
<212> TYPE: PRT
<213> ORGANISM: Schizosaccharomyces pombe

<400> SEQUENCE: 18

```
        Met Ser Phe Phe Thr Gln Leu Cys Ser Met Asp Lys Lys Tyr Trp Ile
        1               5                   10                  15
        Ser Leu Ala Val Leu Ser Val Thr Val Leu Ile Ser Ala Leu Leu Lys
                    20                  25                  30
        Lys Arg Ala Thr Glu Thr Glu Asp Ile Val Val Val His Tyr Asp Gly
                        35                  40                  45
        Glu Lys Leu Asn Phe Val Leu Arg Gln Pro Arg Leu Asn Met Val Ser
                    50                  55                  60
        Tyr Thr Ser Phe Leu Arg Arg Val Cys Asn Ala Phe Ser Val Met Pro
        65                  70                  75                  80
        Asp Lys Ala Ser Leu Lys Leu Asn Gly Val Thr Leu Lys Asp Gly Ser
                        85                  90                  95
        Leu Ser Asp Gln Asn Val Gln Asn Gly Ser Glu Leu Glu Leu Glu Leu
                    100                 105                 110
        Pro Lys Leu Ser Pro Ala Met Gln Gln Ile Glu Ala Tyr Ile Asp Glu
                115                 120                 125
        Leu Gln Gln Asp Leu Val Pro Lys Ile Glu Ala Phe Cys Gln Ser Ser
            130                 135                 140
        Pro Ala Ser Ala Gln Asp Val Gln Asp Leu His Thr Arg Leu Ser Glu
        145                 150                 155                 160
        Thr Leu Leu Ala Arg Met Ile Lys Leu Asp Ala Val Asn Val Glu Asp
                        165                 170                 175
        Asp Pro Glu Ala Arg Leu Lys Arg Lys Glu Ala Ile Arg Leu Ser Gln
                    180                 185                 190
        Gln Tyr Leu Ser Lys Leu Asp Ser Thr Lys Asn Gln Asn Lys
                195                 200                 205
```

<210> SEQ ID NO 19
<211> LENGTH: 2534
<212> TYPE: DNA
<213> ORGANISM: Homo sapiens
<220> FEATURE:
<221> NAME/KEY: CDS
<222> LOCATION: (307)..(2034)

<400> SEQUENCE: 19

```
        gcggagctcc gcatccaacc ccgggccgcg gccaacttct ctggactgga ccagaagttt      60
        ctagccggcc agttgctacc tcccttatc tcctccttcc cctctggcag cgaggaggct     120
        atttccagac acttccaccc ctctctggcc acgtcacccc cgcctttaat tcataaaggt     180
        gcccggcgcc ggcttcccgg acacgtcggc ggcggagagg ggcccacggc ggcggcccgg     240
        ccagagactc ggcgcccgga gccagcgccc cgcacccgcg ccccagcggg cagacccaa      300
        cccagc atg agc gcc gcc acc cac tcg ccc atg atg cag gtg gcg tcc        348
               Met Ser Ala Ala Thr His Ser Pro Met Met Gln Val Ala Ser
               1               5                   10
        ggc aac ggt gac cgc gac cct ttg ccc ccc gga tgg gag atc aag atc     396
        Gly Asn Gly Asp Arg Asp Pro Leu Pro Pro Gly Trp Glu Ile Lys Ile
        15                  20                  25                  30
        gac ccg cag acc ggc tgg ccc ttc ttc gtg gac cac aac agc cgc acc     444
        Asp Pro Gln Thr Gly Trp Pro Phe Phe Val Asp His Asn Ser Arg Thr
                        35                  40                  45
        act acg tgg aac gac ccg cgc gtg ccc tct gag ggc ccc aag gag act     492
        Thr Thr Trp Asn Asp Pro Arg Val Pro Ser Glu Gly Pro Lys Glu Thr
                    50                  55                  60
        cca tcc tct gcc aat ggc cct tcc cgg gag ggc tct agg ctg ccg cct     540
```

```
                Pro Ser Ser Ala Asn Gly Pro Ser Arg Glu Gly Ser Arg Leu Pro Pro
                     65                  70                  75
gct agg gaa ggc cac cct gtg tac ccc cag ctc cga cca ggc tac att         588
Ala Arg Glu Gly His Pro Val Tyr Pro Gln Leu Arg Pro Gly Tyr Ile
         80                  85                  90
ccc att cct gtg ctc cat gaa ggc gct gag aac cgg cag gtg cac cct         636
Pro Ile Pro Val Leu His Glu Gly Ala Glu Asn Arg Gln Val His Pro
 95                 100                 105                 110
ttc cat gtc tat ccc cag cct ggg atg cag cga ttc cga act gag gcg         684
Phe His Val Tyr Pro Gln Pro Gly Met Gln Arg Phe Arg Thr Glu Ala
                115                 120                 125
gca gca gcg gct cct cag agg tca cag tca cct ctg cgg ggc atg cca         732
Ala Ala Ala Ala Pro Gln Arg Ser Gln Ser Pro Leu Arg Gly Met Pro
            130                 135                 140
gaa acc act cag cca gat aaa cag tgt gga cag gtg gca gcg gcg gcg         780
Glu Thr Thr Gln Pro Asp Lys Gln Cys Gly Gln Val Ala Ala Ala
        145                 150                 155
gca gcc cag ccc cca gcc tcc cac gga cct gag cgg tcc cag tct cca         828
Ala Ala Gln Pro Pro Ala Ser His Gly Pro Glu Arg Ser Gln Ser Pro
    160                 165                 170
gct gcc tct gac tgc tca tcc tca tcc tcc tcg gcc agc ctg cct tcc         876
Ala Ala Ser Asp Cys Ser Ser Ser Ser Ser Ala Ser Leu Pro Ser
175                 180                 185                 190
tcc ggc agg agc agc ctg ggc agt cac cag ctc ccg cgg ggg tac atc         924
Ser Gly Arg Ser Ser Leu Gly Ser His Gln Leu Pro Arg Gly Tyr Ile
                195                 200                 205
tcc att ccg gtg ata cac gag cag aac gtt acc cgg cca gca gcc cag         972
Ser Ile Pro Val Ile His Glu Gln Asn Val Thr Arg Pro Ala Ala Gln
            210                 215                 220
ccc tcc ttc cac aaa gcc cag aag acg cac tac cca gcg cag agg ggt         1020
Pro Ser Phe His Lys Ala Gln Lys Thr His Tyr Pro Ala Gln Arg Gly
        225                 230                 235
gag tac cag acc cac cag cct gtg tac cac aag atc cag ggg gat gac         1068
Glu Tyr Gln Thr His Gln Pro Val Tyr His Lys Ile Gln Gly Asp Asp
    240                 245                 250
tgg gag ccc cgg ccc ctg cgg gcg gca tcc ccg ttc agg tca tct gtc         1116
Trp Glu Pro Arg Pro Leu Arg Ala Ala Ser Pro Phe Arg Ser Ser Val
255                 260                 265                 270
cag ggt gca tcg agc cgg gag ggc tca cca gcc agg agc agc acg cca         1164
Gln Gly Ala Ser Ser Arg Glu Gly Ser Pro Ala Arg Ser Ser Thr Pro
                275                 280                 285
ctc cac tcc ccc tcg ccc atc cgt gtg cac acc gtg gtc gac agg cct         1212
Leu His Ser Pro Ser Pro Ile Arg Val His Thr Val Val Asp Arg Pro
            290                 295                 300
cag cag ccc atg acc cat cga gaa act gca cct gtt tcc cag cct gaa         1260
Gln Gln Pro Met Thr His Arg Glu Thr Ala Pro Val Ser Gln Pro Glu
        305                 310                 315
aac aaa cca gaa agt aag cca ggc cca gtt gga cca gaa ctc cct cct         1308
Asn Lys Pro Glu Ser Lys Pro Gly Pro Val Gly Pro Glu Leu Pro Pro
    320                 325                 330
gga cac atc cca att caa gtg atc cgc aaa gag gtg gat tct aaa cct         1356
Gly His Ile Pro Ile Gln Val Ile Arg Lys Glu Val Asp Ser Lys Pro
335                 340                 345                 350
gtt tcc cag aag ccc cca cct ccc tct gag aag gta gag gtg aaa gtt         1404
Val Ser Gln Lys Pro Pro Pro Pro Ser Glu Lys Val Glu Val Lys Val
                355                 360                 365
ccc cct gct cca gtt cct tgt cct cct ccc agc cct ggc cct tct gct         1452
Pro Pro Ala Pro Val Pro Cys Pro Pro Pro Ser Pro Gly Pro Ser Ala
            370                 375                 380
gtc ccc tct tcc ccc aag agt gtg gct aca gaa gag agg gca gcc ccc         1500
Val Pro Ser Ser Pro Lys Ser Val Ala Thr Glu Glu Arg Ala Ala Pro
        385                 390                 395
agc act gcc cct gca gaa gct aca cct cca aaa cca gga gaa gcc gag         1548
Ser Thr Ala Pro Ala Glu Ala Thr Pro Pro Lys Pro Gly Glu Ala Glu
    400                 405                 410
gct ccc cca aaa cat cca gga gtg ctg aaa gtg gaa gcc atc ctg gag         1596
Ala Pro Pro Lys His Pro Gly Val Leu Lys Val Glu Ala Ile Leu Glu
415                 420                 425                 430
aag gtg cag ggg ctg gag cag gct gta gac aac ttt gaa ggc aag aag         1644
Lys Val Gln Gly Leu Glu Gln Ala Val Asp Asn Phe Glu Gly Lys Lys
                435                 440                 445
act gac aaa aag tac ctg atg atc gaa gag tat ttg acc aaa gag ctg         1692
Thr Asp Lys Lys Tyr Leu Met Ile Glu Glu Tyr Leu Thr Lys Glu Leu
            450                 455                 460
ctg gcc ctg gat tca gtg gac ccc gag gga cga gcc gat gtg cgt cag         1740
Leu Ala Leu Asp Ser Val Asp Pro Glu Gly Arg Ala Asp Val Arg Gln
        465                 470                 475
gcc agg aga gac ggt gtc agg aag gtt cag acc atc ttg gaa aaa ctt         1788
Ala Arg Arg Asp Gly Val Arg Lys Val Gln Thr Ile Leu Glu Lys Leu
```

```
                480             485             490
         gaa cag aaa gcc att gat gtc cca ggt caa gtc cag gtc tat gaa ctc    1836
         Glu Gln Lys Ala Ile Asp Val Pro Gly Gln Val Gln Val Tyr Glu Leu
         495             500             505             510
         cag ccc agc aac ctt gaa gca gat cag cca ctg cag gca atc atg gag    1884
         Gln Pro Ser Asn Leu Glu Ala Asp Gln Pro Leu Gln Ala Ile Met Glu
                     515             520             525
         atg ggt gcc gtg gca gca gac aag ggc aag aaa aat gct gga aat gca    1932
         Met Gly Ala Val Ala Ala Asp Lys Gly Lys Lys Asn Ala Gly Asn Ala
                 530             535             540
         gaa gat ccc cac aca gaa acc cag cag cca gaa gcc aca gca gca gcg    1980
         Glu Asp Pro His Thr Glu Thr Gln Gln Pro Glu Ala Thr Ala Ala Ala
             545             550             555
         act tca aac ccc agc agc atg aca gac acc cct ggt aac cca gca gca    2028
         Thr Ser Asn Pro Ser Ser Met Thr Asp Thr Pro Gly Asn Pro Ala Ala
         560             565             570
         ccg tag cctctgccct gtaaaaatca gactcggaac cgatgtgtgc tttagggaat    2084
         Pro
         575
         tttaagttgc atgcatttca gagactttaa gtcagttggt tttattagc tgcttggtat   2144
         gcagtaactt gggtggaggc aaaacactaa taaaagggct aaaaaggaaa atgatgcttt   2204
         tcttctatat tcttactctg tacaaataaa gaagttgctt gttgtttgag aagtttaacc   2264
         ccgttgcttg ttctgcagcc ctgtctactt gggcaccccc accacctgtt agctgtggtt   2324
         gtgcactgtc ttttgtagct ctggactgga ggggtagatg gggagtcaat tacccatcac   2384
         ataaatatga aacatttatc agaaatgttg ccattttaat gagatgattt tcttcatctc   2444
         ataattaaaa tacctgactt tagagagagt aaaatgtgcc aggagccata ggaatatctg   2504
         tatgttggat gactttaatg ctacattttc                                    2534

<210> SEQ ID NO 20
<211> LENGTH: 575
<212> TYPE: PRT
<213> ORGANISM: Homo sapiens

<400> SEQUENCE: 20

Met Ser Ala Ala Thr His Ser Pro Met Met Gln Val Ala Ser Gly Asn
    1               5                   10                  15
    Gly Asp Arg Asp Pro Leu Pro Pro Gly Trp Glu Ile Lys Ile Asp Pro
                    20                  25                  30
    Gln Thr Gly Trp Pro Phe Phe Val Asp His Asn Ser Arg Thr Thr Thr
                35                  40                  45
    Trp Asn Asp Pro Arg Val Pro Ser Glu Gly Pro Lys Glu Thr Pro Ser
        50                  55                  60
    Ser Ala Asn Gly Pro Ser Arg Gly Ser Arg Leu Pro Pro Ala Arg
    65                  70                  75                  80
    Glu Gly His Pro Val Tyr Pro Gln Leu Arg Pro Gly Tyr Ile Pro Ile
                    85                  90                  95
    Pro Val Leu His Glu Gly Ala Glu Asn Arg Gln Val His Pro Phe His
                    100                 105                 110
    Val Tyr Pro Gln Pro Gly Met Gln Arg Phe Arg Thr Glu Ala Ala Ala
                115                 120                 125
    Ala Ala Pro Gln Arg Ser Gln Ser Pro Leu Arg Gly Met Pro Glu Thr
        130                 135                 140
    Thr Gln Pro Asp Lys Gln Cys Gly Gln Val Ala Ala Ala Ala Ala
    145                 150                 155                 160
    Gln Pro Pro Ala Ser His Gly Pro Glu Arg Ser Gln Ser Pro Ala Ala
                    165                 170                 175
    Ser Asp Cys Ser Ser Ser Ser Ser Ala Ser Leu Pro Ser Ser Gly
                    180                 185                 190
    Arg Ser Ser Leu Gly Ser His Gln Leu Pro Arg Gly Tyr Ile Ser Ile
                195                 200                 205
    Pro Val Ile His Glu Gln Asn Val Thr Arg Pro Ala Ala Gln Pro Ser
        210                 215                 220
    Phe His Lys Ala Gln Lys Thr His Tyr Pro Ala Gln Arg Gly Glu Tyr
    225                 230                 235                 240
    Gln Thr His Gln Pro Val Tyr His Lys Ile Gln Gly Asp Asp Trp Glu
                    245                 250                 255
    Pro Arg Pro Leu Arg Ala Ala Ser Pro Phe Arg Ser Ser Val Gln Gly
                260                 265                 270
    Ala Ser Ser Arg Glu Gly Ser Pro Ala Arg Ser Ser Thr Pro Leu His
                275                 280                 285
    Ser Pro Ser Pro Ile Arg Val His Thr Val Val Asp Arg Pro Gln Gln
        290                 295                 300
    Pro Met Thr His Arg Glu Thr Ala Pro Val Ser Gln Pro Glu Asn Lys
    305                 310                 315                 320
    Pro Glu Ser Lys Pro Gly Pro Val Gly Pro Glu Leu Pro Pro Gly His
                    325                 330                 335
    Ile Pro Ile Gln Val Ile Arg Lys Glu Val Asp Ser Lys Pro Val Ser
```

-continued

```
            340                 345                 350
    Gln Lys Pro Pro Pro Ser Glu Lys Val Glu Val Lys Val Pro Pro
                355                 360                 365
    Ala Pro Val Pro Cys Pro Pro Ser Pro Gly Pro Ser Ala Val Pro
        370                 375                 380
    Ser Ser Pro Lys Ser Val Ala Thr Glu Glu Arg Ala Ala Pro Ser Thr
    385                 390                 395                 400
    Ala Pro Ala Glu Ala Thr Pro Pro Lys Pro Gly Glu Ala Glu Ala Pro
                    405                 410                 415
    Pro Lys His Pro Gly Val Leu Lys Val Glu Ala Ile Leu Glu Lys Val
                420                 425                 430
    Gln Gly Leu Glu Gln Ala Val Asp Asn Phe Glu Gly Lys Lys Thr Asp
                435                 440                 445
    Lys Lys Tyr Leu Met Ile Glu Glu Tyr Leu Thr Lys Glu Leu Leu Ala
    450                 455                 460
    Leu Asp Ser Val Asp Pro Glu Gly Arg Ala Asp Val Arg Gln Ala Arg
    465                 470                 475                 480
    Arg Asp Gly Val Arg Lys Val Gln Thr Ile Leu Glu Lys Leu Glu Gln
                        485                 490                 495
    Lys Ala Ile Asp Val Pro Gly Gln Val Gln Val Tyr Glu Leu Gln Pro
                    500                 505                 510
    Ser Asn Leu Glu Ala Asp Gln Pro Leu Gln Ala Ile Met Glu Met Gly
                515                 520                 525
    Ala Val Ala Ala Asp Lys Gly Lys Lys Asn Ala Gly Asn Ala Glu Asp
            530                 535                 540
    Pro His Thr Glu Thr Gln Gln Pro Glu Ala Thr Ala Ala Thr Ser
    545                 550                 555                 560
    Asn Pro Ser Ser Met Thr Asp Thr Pro Gly Asn Pro Ala Ala Pro
                        565                 570                 575
```

<210> SEQ ID NO 21
<211> LENGTH: 1966
<212> TYPE: DNA
<213> ORGANISM: Homo sapiens
<220> FEATURE:
<221> NAME/KEY: CDS
<222> LOCATION: (43)..(1416)

<400> SEQUENCE: 21

```
    cggtgggagc ggggcgggaa gcgcttcagg gcagcggatc cc atg tcg gcc ctg      54
                                                   Met Ser Ala Leu
                                                     1
    agg cgc tcg ggc tac ggc ccc agt gac ggt ccg tcc tac ggc cgc tac    102
    Arg Arg Ser Gly Tyr Gly Pro Ser Asp Gly Pro Ser Tyr Gly Arg Tyr
      5                  10                  15                  20
    tac ggg cct ggg ggt gga gat gtg ccg gta cac cca cct cca ccc tta    150
    Tyr Gly Pro Gly Gly Gly Asp Val Pro Val His Pro Pro Pro Pro Leu
                     25                  30                  35
    tat cct ctt cgc cct gaa cct ccc cag cct ccc att tcc tgg cgg gtg    198
    Tyr Pro Leu Arg Pro Glu Pro Pro Gln Pro Pro Ile Ser Trp Arg Val
                 40                  45                  50
    cgc ggg ggc ggc ccg gcg gag acc acc tgg ctg gga gaa ggc gga gga    246
    Arg Gly Gly Gly Pro Ala Glu Thr Thr Trp Leu Gly Glu Gly Gly Gly
             55                  60                  65
    ggc gat ggc tac tat ccc tcg gga ggc gcc tgg cca gag cct ggt cga    294
    Gly Asp Gly Tyr Tyr Pro Ser Gly Gly Ala Trp Pro Glu Pro Gly Arg
         70                  75                  80
    gcc gga gga agc cac cag gag cag cca cca tat cct agc tac aat tct    342
    Ala Gly Gly Ser His Gln Glu Gln Pro Pro Tyr Pro Ser Tyr Asn Ser
     85                  90                  95                 100
    aac tat tgg aat tct act gcg aga tct agg gct cct tac cca agt aca    390
    Asn Tyr Trp Asn Ser Thr Ala Arg Ser Arg Ala Pro Tyr Pro Ser Thr
                    105                 110                 115
    tat cct gta aga cca gaa ttg caa ggc cag agt ttg aat tct tat aca    438
    Tyr Pro Val Arg Pro Glu Leu Gln Gly Gln Ser Leu Asn Ser Tyr Thr
                120                 125                 130
    aat gga gcg tat ggt cca aca tac ccc cca ggc cct ggg gca aat act    486
    Asn Gly Ala Tyr Gly Pro Thr Tyr Pro Pro Gly Pro Gly Ala Asn Thr
             135                 140                 145
    gcc tca tac tca ggg gct tat tat gca cct ggt tat act cag acc agt    534
    Ala Ser Tyr Ser Gly Ala Tyr Tyr Ala Pro Gly Tyr Thr Gln Thr Ser
         150                 155                 160
    tac tcc aca gaa gtt cca agt act tac cgt tca tct ggc aac agc cca    582
    Tyr Ser Thr Glu Val Pro Ser Thr Tyr Arg Ser Ser Gly Asn Ser Pro
    165                 170                 175                 180
    act cca gtc tct cgt tgg atc tat ccc cag cag gac tgt cag act gaa    630
    Thr Pro Val Ser Arg Trp Ile Tyr Pro Gln Gln Asp Cys Gln Thr Glu
```

```
                    185                 190                 195
         gca ccc cct ctt agg ggg cag gtt cca gga tat ccg cct tca cag aac    678
         Ala Pro Pro Leu Arg Gly Gln Val Pro Gly Tyr Pro Pro Ser Gln Asn
                 200                 205                 210
         cct gga atg acc ctg ccc cat tat cct tat gga gat ggt aat cgt agt    726
         Pro Gly Met Thr Leu Pro His Tyr Pro Tyr Gly Asp Gly Asn Arg Ser
             215                 220                 225
         gtt cca caa tca gga ccg act gta cga cca caa gaa gat gcg tgg gct    774
         Val Pro Gln Ser Gly Pro Thr Val Arg Pro Gln Glu Asp Ala Trp Ala
         230                 235                 240
         tct cct ggt gct tat gga atg ggt ggc cgt tat ccc tgg cct tca tca    822
         Ser Pro Gly Ala Tyr Gly Met Gly Gly Arg Tyr Pro Trp Pro Ser Ser
         245                 250                 255                 260
         gcg ccc tca gca cca ccc ggc aat ctc tac atg act gaa agt act tca    870
         Ala Pro Ser Ala Pro Pro Gly Asn Leu Tyr Met Thr Glu Ser Thr Ser
                         265                 270                 275
         cca tgg cct agc agt ggc tct ccc cag tca ccc cct tca ccc cca gtc    918
         Pro Trp Pro Ser Ser Gly Ser Pro Gln Ser Pro Pro Ser Pro Pro Val
                     280                 285                 290
         cag cag ccc aag gat tct tca tac ccc tat agc caa tca gat caa agc    966
         Gln Gln Pro Lys Asp Ser Ser Tyr Pro Tyr Ser Gln Ser Asp Gln Ser
                 295                 300                 305
         atg aac cgg cac aac ttt cct tgc agt gtc cat cag tac gaa tcc tcg    1014
         Met Asn Arg His Asn Phe Pro Cys Ser Val His Gln Tyr Glu Ser Ser
             310                 315                 320
         ggg aca gtg atc aat gaa gat tca gat ctt ttg gat tcc caa gtc cag    1062
         Gly Thr Val Ile Asn Glu Asp Ser Asp Leu Leu Asp Ser Gln Val Gln
         325                 330                 335                 340
         tat agt gct gag cct cag ctg tat ggt aat gcc acc agt gac cat ccc    1110
         Tyr Ser Ala Glu Pro Gln Leu Tyr Gly Asn Ala Thr Ser Asp His Pro
                         345                 350                 355
         aac aat caa gat caa agt agc agt ctt cct gaa gaa tgt gta ccc tca    1158
         Asn Asn Gln Asp Gln Ser Ser Ser Leu Pro Glu Glu Cys Val Pro Ser
                     360                 365                 370
         gat gaa agt act cct ccg agt att aaa aaa atc ata cat gtg ctg gag    1206
         Asp Glu Ser Thr Pro Pro Ser Ile Lys Lys Ile Ile His Val Leu Glu
                 375                 380                 385
         aag gtc cag tat ctt gaa caa gaa gta gaa gaa ttt gta gga aaa aag    1254
         Lys Val Gln Tyr Leu Glu Gln Glu Val Glu Glu Phe Val Gly Lys Lys
             390                 395                 400
         aca gac aaa gca tac tgg ctt ctg gaa gaa atg cta acc aag gaa ctt    1302
         Thr Asp Lys Ala Tyr Trp Leu Leu Glu Glu Met Leu Thr Lys Glu Leu
         405                 410                 415                 420
         ttg gaa ctg gat tca gtt gaa act ggg ggc cag gac tct gta cgg cag    1350
         Leu Glu Leu Asp Ser Val Glu Thr Gly Gly Gln Asp Ser Val Arg Gln
                         425                 430                 435
         gcc aga aaa gag gct gtt tgt aag att cag gcc ata ctg gaa aaa tta    1398
         Ala Arg Lys Glu Ala Val Cys Lys Ile Gln Ala Ile Leu Glu Lys Leu
                     440                 445                 450
         gaa aaa aaa gga tta tga aaggatttag aacaaagtgg aagcctgtta            1446
         Glu Lys Lys Gly Leu
                     455
         ctaacttgac caaagaacac ttgattaggt taattaccct ctttttgaaa tgcctgttga   1506
         tgacaagaag caatacattc cagcttttcc tttgatttta tacttgaaaa actggcaaag   1566
         gaatggaaga atattttagt catgaagttg ttttcagttt tcagacgaat gaatgtaata   1626
         ggaaactatg gagttaccaa tattgccaag tagactcact ccttaaaaaa tttatggata   1686
         tctacaagct gcttattacc agcaggaggc aaacacactt cacacaacag gcttatcaga   1746
         aacctaccag atgaaactgg atataatttg agacaaacag gatgtgtttt tttaaacatc   1806
         tggatatctt gtcacatttt tgtacattgt gactgctttc aacatatact tcatgtgtaa   1866
         ttatagctta gactttagcc ttcttggact tctgttttgt tttgttattt gcagtttaca   1926
         aatatagtat tattctctaa aaaaaaaaaa aaaaaaaaa                          1966

<210> SEQ ID NO 22
<211> LENGTH: 457
<212> TYPE: PRT
<213> ORGANISM: Homo sapiens

<400> SEQUENCE: 22

Met Ser Ala Leu Arg Arg Ser Gly Tyr Gly Pro Ser Asp Gly Pro Ser
     1               5                  10                  15
    Tyr Gly Arg Tyr Tyr Gly Pro Gly Gly Gly Asp Val Pro Val His Pro
                 20                  25                  30
    Pro Pro Pro Leu Tyr Pro Leu Arg Pro Glu Pro Gln Pro Pro Ile
             35                  40                  45
    Ser Trp Arg Val Arg Gly Gly Gly Pro Ala Glu Thr Thr Trp Leu Gly
         50                  55                  60
    Glu Gly Gly Gly Gly Asp Gly Tyr Tyr Pro Ser Gly Gly Ala Trp Pro
```

```
            65                  70                  75                  80
        Glu Pro Gly Arg Ala Gly Gly Ser His Gln Glu Gln Pro Pro Tyr Pro
                        85                  90                  95
        Ser Tyr Asn Ser Asn Tyr Trp Asn Ser Thr Ala Arg Ser Arg Ala Pro
                    100                 105                 110
        Tyr Pro Ser Thr Tyr Pro Val Arg Pro Glu Leu Gln Gly Gln Ser Leu
                115                 120                 125
        Asn Ser Tyr Thr Asn Gly Ala Tyr Gly Pro Thr Tyr Pro Pro Gly Pro
            130                 135                 140
        Gly Ala Asn Thr Ala Ser Tyr Ser Gly Ala Tyr Tyr Ala Pro Gly Tyr
        145                 150                 155                 160
        Thr Gln Thr Ser Tyr Ser Thr Glu Val Pro Ser Thr Tyr Arg Ser Ser
                        165                 170                 175
        Gly Asn Ser Pro Thr Pro Val Ser Arg Trp Ile Tyr Pro Gln Gln Asp
                    180                 185                 190
        Cys Gln Thr Glu Ala Pro Pro Leu Arg Gly Gln Val Pro Gly Tyr Pro
                195                 200                 205
        Pro Ser Gln Asn Pro Gly Met Thr Leu Pro His Tyr Pro Tyr Gly Asp
            210                 215                 220
        Gly Asn Arg Ser Val Pro Gln Ser Gly Pro Thr Val Arg Pro Gln Glu
        225                 230                 235                 240
        Asp Ala Trp Ala Ser Pro Gly Ala Tyr Gly Met Gly Gly Arg Tyr Pro
                        245                 250                 255
        Trp Pro Ser Ser Ala Pro Ser Ala Pro Pro Gly Asn Leu Tyr Met Thr
                    260                 265                 270
        Glu Ser Thr Ser Pro Trp Pro Ser Ser Gly Ser Pro Gln Ser Pro Pro
                275                 280                 285
        Ser Pro Pro Val Gln Gln Pro Lys Asp Ser Ser Tyr Pro Tyr Ser Gln
            290                 295                 300
        Ser Asp Gln Ser Met Asn Arg His Asn Phe Pro Cys Ser Val His Gln
        305                 310                 315                 320
        Tyr Glu Ser Ser Gly Thr Val Ile Asn Glu Asp Ser Asp Leu Leu Asp
                        325                 330                 335
        Ser Gln Val Gln Tyr Ser Ala Glu Pro Gln Leu Tyr Gly Asn Ala Thr
                    340                 345                 350
        Ser Asp His Pro Asn Asn Gln Asp Gln Ser Ser Ser Leu Pro Glu Glu
                355                 360                 365
        Cys Val Pro Ser Asp Glu Ser Thr Pro Pro Ser Ile Lys Lys Ile Ile
            370                 375                 380
        His Val Leu Glu Lys Val Gln Tyr Leu Glu Gln Glu Val Glu Glu Phe
        385                 390                 395                 400
        Val Gly Lys Lys Thr Asp Lys Ala Tyr Trp Leu Leu Glu Glu Met Leu
                        405                 410                 415
        Thr Lys Glu Leu Leu Glu Leu Asp Ser Val Glu Thr Gly Gly Gln Asp
                    420                 425                 430
        Ser Val Arg Gln Ala Arg Lys Glu Ala Val Cys Lys Ile Gln Ala Ile
                435                 440                 445
        Leu Glu Lys Leu Glu Lys Lys Gly Leu
            450                 455
```

<210> SEQ ID NO 23
<211> LENGTH: 4308
<212> TYPE: DNA
<213> ORGANISM: Homo sapiens
<220> FEATURE:
<221> NAME/KEY: CDS
<222> LOCATION: (247)..(1590)
<221> NAME/KEY: misc_feature
<222> LOCATION: (1)..(4308)
<223> OTHER INFORMATION: n=a,c,t or g

<400> SEQUENCE: 23

```
    cccccccccc cccccccccc ccngaagacg cccggagcgg ctgctgcagc cagtagcggc   60
    cccttcaccg gctgccccgc tcagacctag tcgggagggg tgcgaggcat gcagctgggg  120
    gcccagctcc ggtgccgcac cccgtaaagg gctgatcttc cacctcgcca cctcagccac  180
    gggacgccaa gaccgcatcc aattcagact tcttttggtg cttgtgaaac tgaacacaac  240
    aaaagt atg gat atg gga aac caa cat cct tct att agt agg ctt cag      288
           Met Asp Met Gly Asn Gln His Pro Ser Ile Ser Arg Leu Gln
             1               5                  10
    gaa atc caa aag gaa gta aaa agt gta gaa cag caa gtt atc ggc ttc     336
    Glu Ile Gln Lys Glu Val Lys Ser Val Glu Gln Gln Val Ile Gly Phe
    15                  20                  25                  30
    agt ggt ctg tca gat gac aag aat tac aag aaa ctg gag agg att cta     384
    Ser Gly Leu Ser Asp Asp Lys Asn Tyr Lys Lys Leu Glu Arg Ile Leu
                    35                  40                  45
    aca aaa cag ctt ttt gaa ata gac tct gta gat act gaa gga aaa gga     432
    Thr Lys Gln Leu Phe Glu Ile Asp Ser Val Asp Thr Glu Gly Lys Gly
```

-continued

```
                    50                     55                      60
gat att cag caa gct agg aag cgg gca gca cag gag aca gaa cgt ctt      480
Asp Ile Gln Gln Ala Arg Lys Arg Ala Ala Gln Glu Thr Glu Arg Leu
                    65                      70                  75
ctc aaa gag ttg gag cag aat gca aac cac cca cac cgg att gaa ata      528
Leu Lys Glu Leu Glu Gln Asn Ala Asn His Pro His Arg Ile Glu Ile
        80                      85                      90
cag aac att ttt gag gaa gcc cag tcc ctc gtg aga gag aaa att gtg      576
Gln Asn Ile Phe Glu Glu Ala Gln Ser Leu Val Arg Glu Lys Ile Val
 95                     100                     105                     110
cca ttt tat aat gga ggc aac tgc gta act gat gag ttt gaa gaa ggc      624
Pro Phe Tyr Asn Gly Gly Asn Cys Val Thr Asp Glu Phe Glu Glu Gly
                    115                     120                     125
atc caa gat atc att ctg agg ctg aca cat gtt aaa act gga gga aaa      672
Ile Gln Asp Ile Ile Leu Arg Leu Thr His Val Lys Thr Gly Gly Lys
            130                     135                     140
atc tcc ttg cgg aaa gca agg tat cac act tta acc aaa atc tgt gcg      720
Ile Ser Leu Arg Lys Ala Arg Tyr His Thr Leu Thr Lys Ile Cys Ala
        145                     150                     155
gtg caa gag ata atc gaa gac tgc atg aaa aag cag cct tcc ctg ccg      768
Val Gln Glu Ile Ile Glu Asp Cys Met Lys Lys Gln Pro Ser Leu Pro
    160                     165                     170
ctt tcc gag gat gca cat cct tcc gtt gcc aaa atc aac ttc gtg atg      816
Leu Ser Glu Asp Ala His Pro Ser Val Ala Lys Ile Asn Phe Val Met
175                     180                     185                     190
tgt gag gtg aac aag gcc cga ggg gtc ctg att gca ctt ctg atg ggt      864
Cys Glu Val Asn Lys Ala Arg Gly Val Leu Ile Ala Leu Leu Met Gly
                    195                     200                     205
gtg aac aac aat gag acc tgc agg cac tta tcc tgt gtg ctc tcg ggg      912
Val Asn Asn Asn Glu Thr Cys Arg His Leu Ser Cys Val Leu Ser Gly
                    210                     215                     220
ctg atc gct gac ctg gat gct cta gat gtg tgc ggc cgg aca gaa atc      960
Leu Ile Ala Asp Leu Asp Ala Leu Asp Val Cys Gly Arg Thr Glu Ile
            225                     230                     235
aga aat tat cgg agg gag gta gta gaa gat atc aac aaa tta ttg aaa     1008
Arg Asn Tyr Arg Arg Glu Val Val Glu Asp Ile Asn Lys Leu Leu Lys
        240                     245                     250
tat ctg gat ttg gaa gag gaa gca gac aca act aaa gca ttt gac ctg     1056
Tyr Leu Asp Leu Glu Glu Glu Ala Asp Thr Thr Lys Ala Phe Asp Leu
255                     260                     265                     270
aga cag aat cat tcc att tta aaa ata gaa aag gtc ctc aag aga atg     1104
Arg Gln Asn His Ser Ile Leu Lys Ile Glu Lys Val Leu Lys Arg Met
                    275                     280                     285
aga gaa ata aaa aat gaa ctt ctc caa gca caa aac cct tct gaa ttg     1152
Arg Glu Ile Lys Asn Glu Leu Leu Gln Ala Gln Asn Pro Ser Glu Leu
                    290                     295                     300
tac ctg agc tcc aaa aca gaa ttg cag ggt tta att gga cag ttg gat     1200
Tyr Leu Ser Ser Lys Thr Glu Leu Gln Gly Leu Ile Gly Gln Leu Asp
            305                     310                     315
gag gta agt ctt gaa aaa aac ccc tgc atc cgg gaa gcc agg aga aga     1248
Glu Val Ser Leu Glu Lys Asn Pro Cys Ile Arg Glu Ala Arg Arg Arg
        320                     325                     330
gca gtg atc gag gtg caa act ctg atc aca tat att gac ttg aag gag     1296
Ala Val Ile Glu Val Gln Thr Leu Ile Thr Tyr Ile Asp Leu Lys Glu
335                     340                     345                     350
gcc ctt gag aaa aga aag ctg ttt gct tgt gag gag cac cca tcc cat     1344
Ala Leu Glu Lys Arg Lys Leu Phe Ala Cys Glu Glu His Pro Ser His
                    355                     360                     365
aaa gcc gtc tgg aac gtc ctt gga aac ttg tct gag atc cag gga gaa     1392
Lys Ala Val Trp Asn Val Leu Gly Asn Leu Ser Glu Ile Gln Gly Glu
                    370                     375                     380
gtt ctt tca ttt gat gga aat cga acc gat aag aac tac atc cgg ctg     1440
Val Leu Ser Phe Asp Gly Asn Arg Thr Asp Lys Asn Tyr Ile Arg Leu
            385                     390                     395
gaa gag ctc acc aag cag ctg cta gcc ctg gat gct gtt gat ccg         1488
Glu Glu Leu Thr Lys Gln Leu Leu Ala Leu Asp Ala Val Asp Pro
        400                     405                     410
cag gga gaa gag aag tgt aag gct gcc agg aaa caa gct gtg agg ctt     1536
Gln Gly Glu Glu Lys Cys Lys Ala Ala Arg Lys Gln Ala Val Arg Leu
415                     420                     425                     430
gcg cag aat att ctc agc tat ctc gac ctg aaa tct gat gaa tgg gag     1584
Ala Gln Asn Ile Leu Ser Tyr Leu Asp Leu Lys Ser Asp Glu Trp Glu
                    435                     440                     445
tac tga aataccagag atctcacttt tgatactgtt ttgcacttca tatgtgcttc     1640
Tyr
tatgtataga gagctttcag ttcattgatt tatacgtgca tatttcagtc tcagtattta  1700
tgattgaagc aaattctatt cagtatctgc tgcttttgat gttgcaagac aaatatcatt  1760
acagcacgtt aacttttcca ttcggatcat tatctgtatg atgtggtgtg gtttgtttgg  1820
tttgtccttt tttttgcgtt tttaatcaga aaacaaaata gaggcagctt ttgtagattt  1880
```

-continued

```
taaatgggtt gtgcaagcat taaaatgcag gtctttcaga atctagaact aggcataacc 1940
ttacataata ctaggaaaat tatgagaaag gggaaatttt tggttaaata agagtaaggt 2000
tcaaacacaa gcagtacatg ttctgtttca ttatgctcga tagaaggctt tttttttcact 2060
tataaggcct gattggtcct acccagctta acgggtgggg gttttttttgt ttgttcagac 2120
agtctgttct tttgtaaaca tttttagttg gaaaaacagc atctgcattt tccccatcct 2180
ctacgtttta gagaggaatc ttgtttttgt gtgcaacata agaaaattat gaaaactaat 2240
agccaaaaaa cctttgagat tgcattaaag agaagggata aaggaccagc aataataacct 2300
tgtaagttgc ttttgtttgt aaaatctgag cttatagttt tccttagtga gtaaattcat 2360
aaggatggga acatttaaat taagttaatg ggcctttaaa aaaaaaaag gaaacactca 2420
tacctgtagt tggaggatga atactgagga cgggttacca atgtcaggtt atactaaaac 2480
taaatcagaa agtctgaatg tagcacataa tggttctctt ctgttgtcca aggctgtaaa 2540
atggacagcc ttgtcacacc tccccggtgc tgttttacaa cgtgagggta gacgctgtca 2600
gtaacccaga gggaccaggc cttcctaggt tttctaggca gtcagctgtt aaccactcac 2660
ttagtaaatg tcataactac acctgctcca ggaccaatca gtgaaacctg ctcggaatta 2720
aaggcttcct ctgggtgcct gctgaacaac tgagctcatg tcatgggcat gtggtggttt 2780
ctctgttgcc tgaaagagcc attaaagtca gtcgtgcgtg aagcatctct cttctaaagg 2840
atgtgtattt ccataaaatgc tttctgagga tccggtacaa aatgatttcc caagtttctg 2900
aagtgccttg agaacatgtg ggtccgagtg ttataacaga ctcctccccc gggtcacctt 2960
ttgcctggtc atcctgttag agtacatctt tggaaatcca gggtaatatt ctctttcaga 3020
gatgctcatt gtgtaactct gtgtagggag atagtcactt taaacagctc aaagtagcta 3080
gctaaaggag tagccttaaa tacctaaaag atgacagaag catagccctt aacaaatctt 3140
cagcttgtct ctcagtattt cccaatcatg aaaatccctt gctatgtctt tcctactaga 3200
aatgttctag aatcgctgga cggtggggtc agagggcagt cggtatttag gccgtgagct 3260
tcccatacta ctgcaggtcc aactcctggc aaccgcaggc tcaaggcagg tcattggaat 3320
ccacgttttg gccacagtag ttgtaggatt gcttttctgt atcataattt tagaatgctc 3380
ttaaaatctt gaggaagagt tttttatttttt tatttatttt tgagatggag tctctgttgc 3440
ccaggctgca gtgcagtggt gccatctcag ctcactgcaa cctccacctc ccaggttcaa 3500
gcgattctcc tgcctcagcc acctgagtag ctgggagtac aggcatgtgg caccatgcct 3560
ggctaatttt tgtatttttta atagagttga gatttcacca tgatggtcag gctggtctcg 3620
aactcctgac ctcgtgatcc gcccgcctcg gcccccaaa gtgctgggat taacgggtgt 3680
gagccacggc gcccagccca ggaagagttt taaattaga gctctgttta attataccac 3740
tgggaaatca tggttacgct tcaggcatat tcttccccag agtactactt acattttaaa 3800
tttcattttg taaagttaaa tgtcagcatt ccctttaaaa gtgtccattg ttcttttgaaa 3860
gtagacgttt cagtcattct tttcaaacaa gtgtttgtgt acctttttgcc aagctgtggg 3920
catcgtgtgt gagtacaggg tgctcagctc ttccaccgtc attttgaatt gttcacatgg 3980
gtaattggtc atggaaatga tcagattgac cttgattgac tgtcaggcat ggcttttgttt 4040
ctagttttcaa tctgttctcg ttccttgtac cggattattc tactcctgca atgaaccctg 4100
ttgacaccgg atttagctct tgtcggccett cgtggggagc tgtttgtgtt aaatatgagct 4160
actgcatgta attcttaaac tgggcttgtc acattgtatt gtattttgt gatctgtaat 4220
gaaaagaatc tgtactgcaa gtaaaaccta ctccccaaaa atgtgtggct ttgggtctgc 4280
attaaacgct gtagtccatg ttcatgcc                                    4308
```

<210> SEQ ID NO 24
<211> LENGTH: 447
<212> TYPE: PRT
<213> ORGANISM: Homo sapiens

<400> SEQUENCE: 24

```
Met Asp Met Gly Asn Gln His Pro Ser Ile Ser Arg Leu Gln Glu Ile
  1               5                  10                  15
Gln Lys Glu Val Lys Ser Val Glu Gln Val Ile Gly Phe Ser Gly
                 20                  25                  30
Leu Ser Asp Asp Lys Asn Tyr Lys Lys Leu Glu Arg Ile Leu Thr Lys
             35                  40                  45
Gln Leu Phe Glu Ile Asp Ser Val Asp Thr Glu Gly Lys Gly Asp Ile
         50                  55                  60
Gln Gln Ala Arg Lys Arg Ala Ala Gln Glu Thr Glu Arg Leu Leu Lys
     65                  70                  75              80
Glu Leu Glu Gln Asn Ala Asn His Pro Arg Ile Glu Ile Gln Asn
                 85                  90                  95
Ile Phe Glu Glu Ala Gln Ser Leu Val Arg Glu Lys Ile Val Pro Phe
                100                 105                 110
Tyr Asn Gly Gly Asn Cys Val Thr Asp Glu Phe Glu Gly Ile Gln
             115                 120                 125
Asp Ile Ile Leu Arg Leu Thr His Val Lys Thr Gly Gly Lys Ile Ser
         130                 135                 140
Leu Arg Lys Ala Arg Tyr His Thr Leu Thr Lys Ile Cys Ala Val Gln
    145                 150                 155                160
Glu Ile Ile Glu Asp Cys Met Lys Lys Gln Pro Ser Leu Pro Leu Ser
                165                 170                 175
Glu Asp Ala His Pro Ser Val Ala Lys Ile Asn Phe Val Met Cys Glu
            180                 185                 190
Val Asn Lys Ala Arg Gly Val Leu Ile Ala Leu Met Gly Val Asn
        195                 200                 205
Asn Asn Glu Thr Cys Arg His Leu Ser Cys Val Leu Ser Gly Leu Ile
    210                 215                 220
Ala Asp Leu Asp Ala Leu Asp Val Cys Gly Arg Thr Glu Ile Arg Asn
```

```
                    225                 230                 235                 240
        Tyr Arg Arg Glu Val Val Glu Asp Ile Asn Lys Leu Leu Lys Tyr Leu
                            245                 250                 255
        Asp Leu Glu Glu Glu Ala Asp Thr Thr Lys Ala Phe Asp Leu Arg Gln
                        260                 265                 270
        Asn His Ser Ile Leu Lys Ile Glu Lys Val Leu Lys Arg Met Arg Glu
                    275                 280                 285
        Ile Lys Asn Glu Leu Leu Gln Ala Gln Asn Pro Ser Glu Leu Tyr Leu
                290                 295                 300
        Ser Ser Lys Thr Glu Leu Gln Gly Leu Ile Gly Gln Leu Asp Glu Val
        305                 310                 315                 320
        Ser Leu Glu Lys Asn Pro Cys Ile Arg Glu Ala Arg Arg Ala Val
                        325                 330                 335
        Ile Glu Val Gln Thr Leu Ile Thr Tyr Ile Asp Leu Lys Glu Ala Leu
                    340                 345                 350
        Glu Lys Arg Lys Leu Phe Ala Cys Glu Glu His Pro Ser His Lys Ala
                355                 360                 365
        Val Trp Asn Val Leu Gly Asn Leu Ser Glu Ile Gln Gly Glu Val Leu
            370                 375                 380
        Ser Phe Asp Gly Asn Arg Thr Asp Lys Asn Tyr Ile Arg Leu Glu Glu
        385                 390                 395                 400
        Leu Leu Thr Lys Gln Leu Leu Ala Leu Asp Ala Val Asp Pro Gln Gly
                        405                 410                 415
        Glu Glu Lys Cys Lys Ala Ala Arg Lys Gln Ala Val Arg Leu Ala Gln
                    420                 425                 430
        Asn Ile Leu Ser Tyr Leu Asp Leu Lys Ser Asp Glu Trp Glu Tyr
                        435                 440                 445
```